United States Patent
Conway et al.

(10) Patent No.: US 10,960,085 B2
(45) Date of Patent: Mar. 30, 2021

(54) MODULATION OF LIVER GENES

(71) Applicant: Sangamo Therapeutics, Inc., Richmond, CA (US)

(72) Inventors: Anthony Conway, Richmond, CA (US); Gary K. Lee, Richmond, CA (US); David Paschon, Richmond, CA (US); Lei Zhang, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 702 days.

(21) Appl. No.: 15/697,917

(22) Filed: Sep. 7, 2017

(65) Prior Publication Data

US 2018/0064827 A1    Mar. 8, 2018

Related U.S. Application Data

(60) Provisional application No. 62/384,428, filed on Sep. 7, 2016.

(51) Int. Cl.
| | |
|---|---|
| C07K 14/00 | (2006.01) |
| A61K 48/00 | (2006.01) |
| C12N 5/00 | (2006.01) |
| C12N 9/64 | (2006.01) |
| C12N 9/22 | (2006.01) |
| C07K 14/81 | (2006.01) |
| C12N 9/04 | (2006.01) |
| C07K 14/47 | (2006.01) |
| C12N 15/861 | (2006.01) |
| C12N 15/867 | (2006.01) |
| A61K 39/00 | (2006.01) |

(52) U.S. Cl.
CPC .......... *A61K 48/0058* (2013.01); *C07K 14/47* (2013.01); *C07K 14/8125* (2013.01); *C12N 9/0006* (2013.01); *C12N 9/22* (2013.01); *C12N 9/6424* (2013.01); *C12N 9/6445* (2013.01); *C12N 15/8616* (2013.01); *C12N 15/8676* (2013.01); *A61K 2039/505* (2013.01); *C07K 2319/80* (2013.01); *C12N 2310/10* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas, III et al. | |
| 6,200,759 B1 | 3/2001 | Dove et al. | |
| 6,242,568 B1 | 6/2001 | Barbas, III et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,511,808 B2 | 1/2003 | Wolffe et al. | |
| 6,534,261 B1 | 3/2003 | Cox, III et al. | |
| 6,599,692 B1 | 7/2003 | Case et al. | |
| 6,689,558 B2 | 2/2004 | Case | |
| 6,733,970 B2 | 5/2004 | Choo et al. | |
| 6,746,838 B1 | 6/2004 | Choo et al. | |
| 6,794,136 B1 | 9/2004 | Eisenberg et al. | |
| 6,866,997 B1 | 3/2005 | Choo et al. | |
| 6,903,185 B2 | 6/2005 | Kim et al. | |
| 6,919,204 B2 | 7/2005 | Wolffe et al. | |
| 7,030,215 B2 | 4/2006 | Liu et al. | |
| 7,053,264 B2 | 5/2006 | Wolffe | |
| 7,067,317 B2 | 6/2006 | Rebar et al. | |
| 7,070,934 B2 | 7/2006 | Cox, III et al. | |
| 7,153,949 B2 | 12/2006 | Kim et al. | |
| 7,241,573 B2 | 7/2007 | Choo et al. | |
| 7,241,574 B2 | 7/2007 | Choo et al. | |
| 7,253,273 B2 | 8/2007 | Collingwood | |
| 7,262,054 B2 | 8/2007 | Jamieson et al. | |
| 7,297,491 B2 | 11/2007 | Joung et al. | |
| 7,361,635 B2 | 4/2008 | Miller et al. | |
| 7,888,121 B2 | 2/2011 | Urnov et al. | |
| 7,914,796 B2 | 3/2011 | Miller et al. | |
| 7,951,925 B2 | 5/2011 | Ando et al. | |
| 7,972,854 B2 | 7/2011 | Miller et al. | |
| 8,034,598 B2 | 10/2011 | Miller | |
| 8,110,379 B2 | 2/2012 | DeKelver et al. | |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Ding et al. "Permanent Alteration of PCSK9 With In Vivo CRISPR-Cas9 Genome Editing", Circ Res. Jun. 2014, 115: 488-492. (Year: 2014).*

Rieder et al. "*Homo sapiens* proprotein convertase subtilisin/kexin type 9 (PCSK9) gene, complete cds", NCBI, Accession: AY829011, submitted: Nov. 2004 (search tool: https://www.ncbi.nlm.nih.gov/nuccore/AY829011.1?report=graph). (Year: 2004).*

Wilson et al. "Design and Development of Artificial Zinc Finger Transcription Factors and Zinc Finger Nucleases to the hTERT Locus", Molecular Therapy—Nucleic Acids (2013) 2, e87, pp. 1-10. (Year: 2013).*

Abifadel et al. "Mutations and Polymorphisms in the Proprotein Convertase Subtilisin Kexin 9 (PCSK9) Gene in Cholesterol Metabolism and Disease", Human Mutation, vol. 30, No. 4, 520-529, 2009. (Year: 2009).*

(Continued)

*Primary Examiner* — Kevin K Hill
*Assistant Examiner* — James Joseph Graber
(74) *Attorney, Agent, or Firm* — Dahna S. Pasternak; Pasternak Patent Law

(57) ABSTRACT

Described herein are compositions and methods for modulation of gene expression in the liver including modulation of PCSK9, TTR, SERPINA1, KLKB1 and/or HAO1.

19 Claims, 9 Drawing Sheets

Specification includes a Sequence Listing.

(56) References Cited

U.S. PATENT DOCUMENTS

| | | | |
|---|---|---|---|
| 8,409,861 | B2 | 4/2013 | Guschin et al. |
| 8,420,782 | B2 | 4/2013 | Bonas et al. |
| 8,440,431 | B2 | 5/2013 | Voytas et al. |
| 8,563,314 | B2 | 10/2013 | Gregory et al. |
| 8,586,526 | B2 | 11/2013 | Gregory et al. |
| 8,623,618 | B2 | 1/2014 | Doyon et al. |
| 8,697,359 | B1 | 4/2014 | Zhang |
| 8,703,489 | B2 | 4/2014 | Wang |
| 8,771,985 | B2 | 7/2014 | Cui et al. |
| 8,841,260 | B2 | 9/2014 | Miller et al. |
| 8,945,868 | B2 | 2/2015 | Collingwood et al. |
| 8,956,828 | B2 | 2/2015 | Bonini et al. |
| 9,005,973 | B2 | 4/2015 | Cost et al. |
| 9,045,763 | B2 | 6/2015 | DeKelver et al. |
| 9,150,847 | B2 | 10/2015 | Rebar |
| 9,175,280 | B2 | 11/2015 | Gregory et al. |
| 9,200,266 | B2 | 12/2015 | Wang |
| 9,234,016 | B2 | 1/2016 | Gregory et al. |
| 9,255,250 | B2 | 2/2016 | Gregory et al. |
| 9,267,135 | B2 | 2/2016 | Church et al. |
| 9,567,609 | B2 | 2/2017 | Paschon et al. |
| 2003/0232410 | A1 | 12/2003 | Liljedahl et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2006/0063231 | A1 | 3/2006 | Li et al. |
| 2008/0159996 | A1 | 7/2008 | Ando et al. |
| 2010/0113575 | A1 | 5/2010 | Sitlani et al. |
| 2010/0218264 | A1* | 8/2010 | Cui et al. ............ A01K 67/027 800/14 |
| 2011/0082093 | A1* | 4/2011 | Gregory et al. ....... A61K 38/16 514/21.2 |
| 2011/0201055 | A1 | 8/2011 | Doyon et al. |
| 2011/0265198 | A1* | 10/2011 | Gregory et al. ....... C12N 15/01 800/21 |
| 2011/0301073 | A1 | 12/2011 | Gregory et al. |
| 2012/0017290 | A1 | 1/2012 | Cui et al. |
| 2013/0122591 | A1 | 5/2013 | Cost et al. |
| 2013/0137104 | A1 | 5/2013 | Cost et al. |
| 2013/0177960 | A1 | 7/2013 | Regar |
| 2013/0177983 | A1 | 7/2013 | Rebar |
| 2013/0196373 | A1 | 8/2013 | Gregory et al. |
| 2013/0253040 | A1* | 9/2013 | Miller et al. ........... C07K 14/47 514/44 R |
| 2013/0326645 | A1* | 12/2013 | Cost et al. ............ C12N 15/85 800/14 |
| 2014/0017212 | A1 | 1/2014 | Rebar et al. |
| 2014/0093913 | A1 | 4/2014 | Cost et al. |
| 2014/0304853 | A1* | 10/2014 | Ainley et al. ......... C12N 15/82 800/278 |
| 2014/0356958 | A1 | 12/2014 | Mali et al. |
| 2015/0031134 | A1 | 1/2015 | Zhang et al. |
| 2015/0056705 | A1 | 2/2015 | Conway et al. |
| 2015/0128307 | A1* | 5/2015 | Sastry-Dent et al. . C12N 15/11 |
| 2015/0128309 | A1* | 5/2015 | Sastry-Dent et al. . C12N 15/82 |
| 2015/0132269 | A1* | 5/2015 | Orkin et al. ............ C12N 9/22 |
| 2015/0159172 | A1 | 6/2015 | Miller et al. |
| 2015/0329875 | A1 | 11/2015 | Gregory et al. |
| 2015/0335708 | A1 | 11/2015 | Froelich et al. |
| 2016/0153005 | A1 | 6/2016 | Zhang et al. |
| 2017/0119906 | A1 | 5/2017 | Riley et al. |
| 2017/0211075 | A1 | 7/2017 | Lee et al. |
| 2017/0218349 | A1 | 8/2017 | Miller et al. |
| 2018/0087072 | A1 | 3/2018 | Miller et al. |

FOREIGN PATENT DOCUMENTS

| | | |
|---|---|---|
| WO | WO 96/06166 A1 | 2/1996 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/83793 A2 | 11/2001 |
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 2009/130208 A1 | 10/2009 |
| WO | WO 2014/064277 A1 | 5/2014 |
| WO | 2014207232 A1 | 12/2014 |
| WO | WO 2017/074526 A1 | 5/2017 |

OTHER PUBLICATIONS

Gaj et al. "ZFN, TALEN and CRISPR/Cas-based methods for genome engineering", Trends Biotechnol. Jul. 2013 ; 31(7): 397-405. (Year: 2013).*

Bloom, et al., "Inactivation of Hepatitis B Virus Replication in Cultured Cells and In Vivo With Engineered Transcription Activator-Like Effector Nucleases," Molecular Therapy 21(10): 1889-1897 (2013).

Chen, et al., "A TALEN-Based Specific Transcript Knock-Down of PIWIL2 Supresses Cell Growth in HEPG2 Tumor Cell," Cell Proliferation 47(5): 448-456 (2014).

Choi, et al., "Efficient Drug Screening and Gene Correction for Treating Liver Disease Using Patient-Specific Stem Cells," Hepatology 57(6): 2458-3468 (2013).

Conway, et al., "Non-viral Delivery of Zinc Finger Nuclease MRNA Enables Highly Efficient In Vivo Genome Editing of Multiple Therapeutic Gene Targets," Molecular Therapy 27(4):866-877 (2019).

Li, et al., "In Vivo ZFN-Mediated Editing of the Mutant SERPINA1 Gene Results in Spontaneous Liver Repopulation by Gene-Edited Hepatocytes and Greatly Decreased Fibrosis in the PIZ Mouse Model of Alpha-1 Antitrypsin Deficiency Liver Diseases," 20th Annual Meeting of the ASGCT (Apr. 24, 2017).

Porro, et al., "Generation of UGT1-Deficient Murine Liver Cell Lines Using TALEN Technology," PloS One 9(8): e104816 (2014).

Yusa, et al., "Targeted Gene Correction of α1-Antitrypsin Deficiency in Induced Pluripotent Stem Cells," Nature 478(7369): 391-394 (2011).

Abifadel, et al., "Mutations in PCSK9 Cause Autosomal Dominant Hypercholesterolemia," Nature Genetics 34(2):154-156 (2003).

Beerli, et al., "Engineering Polydactyl Zinc-Finger Transcription Factors," Nature Biotechnology 20:135-141 (2002).

Boch, et al., "Breaking the Code of DNA Binding Specificity of TAL-Type III Effectors," Science 326:1509-1512 (2009).

Bonas, et al., "Genetic and Structural Characterization of the A Virulence Gene AVRBS3 From Xanthomonas Campestris PV. Vesicatoria," Mol Gen Genet 218:127-136 (1989).

Carlson, et al., "Accumulation of PIZ $\alpha_1$-Antitrypsin Causes Liver Damage in Transgenic Mice," J. Clin Invest 83:1183-1190 (1989).

Choo, et al., "Advances in Zinc Finger Engineering," Current Opinion in Structural Biology 10:411-416 (2000).

Christofidou-Solomidou, et al., "Immunotargeting of Glocose Oxidase to Endothelium In Vivo Cause Oxidative Vascular Injury in the Lungs," Am J Physiol Lung Cell Mol Physiol 278: L794-L805 (2000).

Chuah, et al., "Liver-Specific Transcriptional Modules Identified by Genome-Wide in Silico Analysis Enable Efficient Gene Therapy in Mice and Non-human Primates," Molecular Therapy 22:1605-1613 (2014).

Cohen, et al., "Sequence Variations in PCSK9, Low LDL, and Protection Against Coronary Heart Disease," The New England Journal of Medicine 354(12):1264-1272 (2006).

Cong, et al., "Multiplex Genome Engineering Using CRISPR/CAS Systems," Science 339(6121): 819-823 (2013).

Ding, et al., "Permanent Alteration of PCSK9 With In Vivo CRISPR-CAS9 Genome Editing," Circ Res 115:488-492 (2014).

Durai, et al., "Zinc Finger Nucleases: Custom-Designed Molecular Scissors for Genome Engineering of Plant and Mammalian Cells," Nucleic Acids Research 33(18):5978-5990 (2005).

(56) References Cited

OTHER PUBLICATIONS

Esvelt, et al., "Orthogonal CAS9 Proteins for RNA-Guided Gene Regulation and Editing," *Nature Methods* 10(11):1116 (2013).
Eytan, et al., "Current Treatment for Primary Hyperoxaluria Type 1: When Should Liver/Kidney Transplantation Be Considered," *Pediatr Transplant* 13(7): 805-807 (2009).
Fagerlund, et al., "The CPF1 CRISPR-CAS Protein Expands Genome-Editing Tools," *Genom Bio* 16:251 (2015).
Fonfara, et al., "Phylogeny of CAS9 Determines Functional Exchangeability of Dual-RNA and CAS9 Among Orthologous Type II CRISPR-CAS Systems," *Nucleic Acids Research* 42(4):2377-2590 (2013).
Guillinger, et al., "Fusion of Catalytically Inactive CAS9 to FOKL Nuclease Improves the Specificity of Genome Modification," *Nature Biotech*. 32(6):577-582 (2014).
Guo, et al., "Antisense Oligonucleotide Treatment Ameliorates Alpha-1 Antitrypsin-Related Liver Disease in Mice," *J Clin Invest* 124(1):251-261 (2014).
Haft, et al., "A Guild of 45 CRISPR-Associated (CAS) Protein Families and Multiple CRISPR/CAS Subtypes Exist in Prokaryotic Genomes," *PLoS Computational Biology* 1(6):e60 (2005).
Haut, et al., "Intron Definition Is Required for Excision of the Minute Virus of Mice Small Intron and Definition of the Upstream Exon," *Journal of Virology* 72:1834-1843 (1998).
Haut, et al., "Inclusion of the NS2-Specific Exon in Minute Virus of Mice MRNA Is Facilitated by an Intronic Splicing Enhancer That Affects Definition of the Downstream Small Intron," *Virology* 258:84-94 (1999).
Heuer, et al., "Repeat Domain Diversity of AVRBS3-Like Genes in Ralstonia Solanacearum Strains and Association With Host Preferences in the Field," *Applied and Environmental Microbiology* 73(13):4379-4384 (2007).
Hsu, et al., "DNA Targeting Specificity of RNA-Guided CAS9 Nucleases," *Nature Biotech*. 31(9):827-832 (2013).
Hwang, et al., "Efficient In Vivo Genome Editing Using RNA-Guided Nucleases," *Nat Biotechnol* 31(3):227-229 (2013).
Isalan, et al., "A Rapid, Generally Applicable Method to Engineer Zinc Fingers Illustrated by Targeting the HIV-1 Promoter," *Nat Biotechnol.* 19(7):656-660 (2001).
Jansen, et al., "Identification of Genes That Are Associated With DNA Repeats in Prokaryotes," *Molecular Microbiology* 43(6):1565-1575 (2002).
Jinek, et al., "A Programmable Dual-RNA—Guided DNA Endonuclease in Adaptive Bacterial Immunity," *Science* 337:816-821 (2012).
Johnson, et al., "The Transthyretin Amyloidoses: From Delineating the Molecular Mechanism of Aggregation Linked to Pathology to a Regulatory Agency Approved Drug," *J. Mol. Biol.* 421(2-3):185-203 (2012) doi:10.1016/j.jmb.2011.12.060.
Kay, et al., "A Bacterial Effector Acts as a Plant Transcription Factor and Induces a Cell Size Regulator," *Science* 318:648-651 (2007).
Koepke, et al., "Therapy with Plasma Purified Alpha1-Antitrypsin (Prolastin®) Induces Time-Dependent Changes in Plasma Levels of MMP-9 and MPO," *PLoS One* 10(1):e0117497 (2015).
Lewis, "Expanding the Clinical Indications for A1-Antitrypsin Therapy," *Molecular Medicine* 18:957-970 (2012).
Makarova, et al., "A DNA Repair System Specific for Thermophilic Archaea and Bacteria Predicted by Genomic Context Analysis," *Nucleic Acids Research* 30(2):482-496 (2002).
Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biology Direct* 1:7 (2006).
McCaffrey, et al., "CRISPR-CAS9 D10A Nickase Target-Specific Fluorescent Labeling of Double Strand DNA for Whole Genome Mapping and Structural Variation Analysis," *Nucleic Acids Res.* 44(2):e11.doi: 10.1093/nar/gkv878 (2015).
Moscou, et al., "A Simple Cipher Governs DNA Recognition by TAL Effectors," *Science* 326:1501 (2009).
Nair, et al., "Computationally Designed Liver-Specific Transcriptional Modules and Hyperactive Factor IX Improve Hepatic Gene Therapy," *Blood* 123:3195-3199 (2014).
Nolkemper, et al., "Long-Term Results of Pre-emptive Liver Transplantation in Primary Hyperoxaluria Type 1," *Pediatr Transplant* 4(3): 177-181 (2000).
Pabo, et al., "Design and Selection of Novel CYS2-HIS2 Zinc Finger Proteins," *Ann. Rev. Biochem*. 70:313-340 (2001).
Perez, et al., "Establishment of HIV-1 Resistance in CD4[+] T Cells by Genome Editing Using Zinc-Finger Nucleases," *Nature Biotechnology* 26(7):808-816 (2008).
Perez-Pinera, et al., "RNA-Guided Gene Activation by CRISPR-CAS9-Based Transcription Factors," *Nature Methods* 10(10):973-976 (2013).
Piatek, et al., "RNA-Guided Transcriptional Regulation in Planta via Synthetic DCAS9-Based Transcription Factors," *Plant Biotechnology J.* 13(4): 578-589 (2015).
Prieto, et al., "Missense Mutation THR309LYS in the Coagulation Factor XII Gene in a Spanish Family With Hereditary Angioedema Type III," Allergy 64(2): 284-286 (2009).
Rijavec, et al., "Hereditary Angioedema Nationwide Study in Slovenia Reveals Four Novel Mutations in SERPING1 Gene," PLOS One 8(2):e56712 (2013).
Sander, et al., "CRISPR-CAS Systems for Genome Editing, Regulation and Targeting," *Nature Biotechnol* 32(4):347-355 (2014).
Schornack, et al., "Gene-for-Gene-Mediated Recognition of Nuclear-Targeted AVRBS3-Like Bacterial Effector Proteins," *Journal of Plant Physiology* 163(3):256-272 (2006).
Segal, et al., "Custom DNA-Binding Proteins Come of Age: Polydactyl Zinc-Finger Proteins," *Current Opinion Biotechnology* 12:632-637 (2001).
Sheng, et al., "Structure-Based Cleavage Mechanism of Thermus Thermophilus Argonaute DNA Guide Strand-Mediated DNA Target Cleavage," *Proc. Natl. Aca. Sci. U.S.A.* 111(2):652-657 (2014).
Siegal, et al., "Liver-Kidney Transplantation in Primary Hyperoxaluria Type-1: Case Report and Literature Review," *Int J Organ Transpl Med* 2(3):126-132 (2011).
Sternberg, et al., "DNA Interrogation by the CRISPR RNA-Guided Endonuclease CAS9," *Nature* 507(7490):62-67 (2014).
Swarts, et al., "DNA-Guided DNA Interference by a Prokaryotic Argonaute," *Nature* 507(7491):258-261 doi:10.1038/nature12971 (2014).
Tsai, et al., "Guide-SEQ Enables Genome-Wide Profiling of Off-Target Cleavage by CRISPR-CAS Nucleases," *Nat Biotech* 33(2): 187-198 (2015).
Tse, et al., "Recognizing and Managing Hereditary Angioedema," *Abstract Cleveland Clinic Journal of Medicine* 80(5):297-308 (2013).
Tuder, et al., "Lung Disease Associated With A1-Antitrypsin Deficiency," *Proc. Am. Thorac. Soc.* 7:381-386 (2010).
Urnov, et al., "Highly Efficient Endogenous Human Gene Correction Using Designed Zinc-Finger Nucleases," *Nature* 435(7042):646-651 (2005).
Wu, et al., "Genome-Wide Binding of the CRISPR Endonuclease CAS9 in Mammalian Cells," *Nature Biotechnology* 32(7): 670-676 (2014).
Yu, et al., "An Engineered VEGF-Activating Zinc Finger Protein Transcription Factor Improves Blood Flow and Limb Salvage in Advanced-Age Mice," *FASEB J.* 20(3):479-481 (2006).
Yusa, et al, "Targeted Gene Correction of A1-Antitrypsin Deficiency in Induced Pluripotent Stem Cells," *Nature* 478:391-396 (2011).
Zhang, et al., "Synthetic Zinc Finger Transcription Factor Action at an Endogenous Chromosomal Site," *Journal of Biological Chemistry* 275(43):33850-33860 (2000).
Li, et al., "Metabolism of 13C5-Hydroxyproline in Mouse Models of Primary Hyperoxaluria and Its Inhibition by RNAI Therapeutics Targeting Liver Glycolate Oxidase and Hydroxyproline Dehydrogenase," Biochim Biophys Acta 1862(2):233-239 (2016) (Published online Dec. 2, 2015. doi: 10.1016/j.bbadis.2015.12.001).
Wang, et al., "CRISPR-CAS9 Targeting of PCSK9 in Human Hepatocytes In Vivo—Brief Report," Aterioscler Thromb Vasc Biol 36(5):783-786 (2016) (Published online Epub Mar. 3, 2016. doi: 10.1161/ATVBAHA.116.307227).

\* cited by examiner

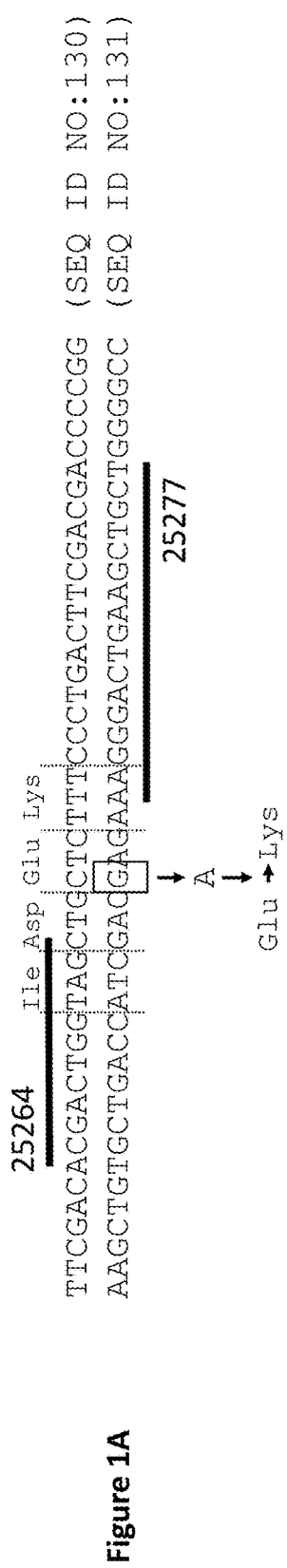

Figure 4A

Exon 1
(69-bp)

gacaggaATGGCTTCCCTTCGACTCTTCCTCCTTTGCCTCGCTGGACTGGTATTTGTGTCTGAAGCTGGCCCGCGgtgagtgatcctgtgagcga ctgtccTACCGAAGGGAAGCTGAGAAGGAGGAAACGGAGCGACCTGACCATAAACACAGACTTCGACCGGGGCGCcactcactaggacactcgct

Exon 1
(69-bp)

gacaggaATGGCTTCCCTTCGACTCTTCCTCCTTTGCCTCGCTGGACTGGTATTTGTGTCTGAAGCTGGCCCGCGgtgagtgatcctgtgagcga ctgtccTACCGAAGGGAAGCTGAGAAGGAGGAAACGGAGCGACCTGACCATAAACACAGACTTCGACCGGGGCGCcactcactaggacactcgct

Exon 1
(69-bp)

gacaggaATGGCTTCCCTTCGACTCTTCCTCCTTTGCCTCGCTGGACTGGTATTTGTGTCTGAAGCTGGCCCGCGgtgagtgatcctgtgagcga ctgtccTACCGAAGGGAAGCTGAGAAGGAGGAAACGGAGCGACCTGACCATAAACACAGACTTCGACCGGGGCGCcactcactaggacactcgct

Exon 2
(131-bp)

gtgcccagGGTGCTGGAGAATCCAAATGTCCTCTGATGGTCAAAGTCCTGAGGCAGCCCTGCTGTCCGAGGCTGTCTAGACGTGGCTGTAAAGTGTT
cacggtcCCACGACCTCTTAGGTTTACAGGAGACTACCAGTTTCAGGACTACGAGACCTCCGTCGGGACGACATCTGCACCGACATTTCACAA CAAAAAGACCTCTGAGGGATCCTGGGAGCCCTTTGCCCTCGGtaagctt
GTTTTTCTCGGAGACTCCCTAGGACCCTCGGGAAACGAGACCcattcgaa

Exon 3
(136-bp)

ccctccagGAAGAGACCGGGAGCTGGAGAGCTGCACGGCTGCACCACAGATGAGAAGTTTGTAGAAGGAGTGTACAGAGTAGAACTGACACCAAAT
gggaggtcCTTCTGGCCCTCGACCTCTCGACGTGCCCGAGTGGGTGTCTACTCTTCCTCACATGTCTCATCTTGACCTGTGTTTA

L  M

K (2 bottom sites)

CGTACTGGAAGAGACACTTGGCATTTCCCCGTTCCATGAATTCGCGGATgtaagtgg
GCATGACCTTCTGTGAACCGTAAAGGGCAAGTACTAAGCGCCTAcattcacc

SEQUENCE LISTING

```
<160> NUMBER OF SEQ ID NOS: 274

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tacgtggtgg tgctgaagga ggagaccc                                              28

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aggatccgtg gaggttgcct ggcaccta                                              28

<210> SEQ ID NO 3
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ttaccggggg gctggtattc atccgccc                                        28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccgcccggta ccgtggaggg gtaatccg                                        28

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 agatggggt cttaccgggg ggctggta                                         28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggtaccgggc ggatgaatac cagccccc                                        28

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gaggctgggg agtagaggca ggcatcgt                                        28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cgctgccggc aacttccggg acgatgcc                                        28

<210> SEQ ID NO 9
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
agagaagtgg atcagtctct gcctcaac                                           28

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cggagctcac cctggccgag ttgaggca                                           28

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tatccccggc gggcagcctg ggcctgca                                           28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tgcaggcggc gggcagtgcg ctctgact                                           28

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Ser Ser His Leu Thr Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ser Gly Asn Leu Ala Arg
1               5

<210> SEQ ID NO 15
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Ser Ser Asp Leu Ser Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp His Ser Ser Leu His Gln
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Arg His His Leu Thr Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

His Lys Gln His Arg Asp Ala
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ser Asp Val Leu Ser Glu
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20
```

Thr Arg Asn Gly Leu Lys Tyr
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Ser Gly His Leu Ser Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Ser Gly His Leu Ser Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asn Asn Arg Asp Leu Ile Asn
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Ser Ser Asn Leu Ser Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Ser Gly Ala Leu Ala Arg
1               5

<210> SEQ ID NO 26
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 26

Arg Ser Ala His Leu Ser Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ser Asp His Leu Ser Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Arg Ser Val Leu Ala Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Asn Ser Asn Arg Ile Lys
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ser Asp His Leu Ser Glu
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

His Ser Arg Thr Arg Thr Lys
1               5

```
<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gln Trp Asp Arg Lys Gln
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Pro Ser Tyr Leu Pro Thr
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Arg Ser Ala Leu Ala Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Lys Asp Ala Arg Ile Thr
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Ser Gly Asn Leu Thr Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37
```

```
Arg Ser Asp Leu Thr Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Lys Ser Asn Arg Lys Lys
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ser Gly Asp Leu Thr Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Ser Asp Asn Leu Thr Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ser Asp His Leu Ser Gln
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Ser Ser His Arg Thr Arg
1               5

<210> SEQ ID NO 43
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 43

Asp Ser Ser Asp Arg Lys Lys
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln His Gln Val Leu Val Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Asn Ala Thr Arg Thr Lys
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ser Asp Thr Leu Ser Glu
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ser Pro Gly Arg Met Gly
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Gly Tyr Tyr Leu Pro Thr
1               5
```

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Glu Arg Gln Thr Leu Ile Lys
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

His Arg Trp His Leu Gln Thr
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Gln Cys Cys Leu Phe His
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ser Asp Asn Leu Ala Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Arg Ser Val Leu His Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 54

Arg Ser Asp Thr Leu Ser Ala
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Lys Ser Thr Arg Thr Lys
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Pro Cys Arg Tyr Arg Leu Asp
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ser Ala Asn Leu Thr Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Lys Cys Cys Leu Arg Ser
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Arg Ser His Leu Thr Arg
1               5

<210> SEQ ID NO 60
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 60

Arg Ser Asp Thr Leu Ser Asn
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Asn Ser Asp Arg Thr Lys
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

His Arg Gln Arg Leu Glu Glu
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Asn Ala Ser Arg Thr Arg
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Lys Pro Tyr Asn Leu Gln Gln
1               5

<210> SEQ ID NO 65
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gtcgatggtc agcacagcct tatgcacg                                         28
```

<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gaaagggact gaagctgctg gggccatg                                      28

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Ser Gly Ser Leu Thr Arg
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Ser Ala Asp Arg Thr Lys
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Ser Asp His Leu Ser Thr
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Ser Ala His Arg Ile Thr
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

-continued

Gln Ser Ser Asp Leu Arg Arg
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Ser Gly His Leu Ala Arg
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Leu Asp Asn Arg Thr Ala
1               5

<210> SEQ ID NO 74
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ctttgcctcg ctggactggt atttgtgt                                        28

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ccgcggggcc agcttcagac acaaatac                                        28

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gtgcccaggg tgctggagaa tccaaatg                                        28

<210> SEQ ID NO 77
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 77
aggactttga ccatcagagg acatttgg                                              28

<210> SEQ ID NO 78
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
aaaaagacct ctgagggatc ctgggagc                                              28

<210> SEQ ID NO 79
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cttacccaga ggcaaagggc tcccagga                                              28

<210> SEQ ID NO 80
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gcagaggagg agcagacgat gagaagcc                                              28

<210> SEQ ID NO 81
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
attcttggca ggatggcttc tcatcgtc                                              28

<210> SEQ ID NO 82
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gaggaggagc agacgatgag aagccatc                                              28

<210> SEQ ID NO 83
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 83
ccttgctgga ctggtatttg tgtctgag                                              28

<210> SEQ ID NO 84
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
cacatgcacg gccacattga tggcagga                                              28

<210> SEQ ID NO 85
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
tagatgctgt ccgaggcagt cctgccat                                              28

<210> SEQ ID NO 86
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tgcatgctca tggaatgggg agatgcca                                              28

<210> SEQ ID NO 87
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cttactggaa ggcacttggc atctcccc                                              28

<210> SEQ ID NO 88
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gctcatggaa tggggagatg ccaagtgc                                              28

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
```
gcagaggtga gtatacagac cttcgagg                                        28

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Leu Tyr Thr Leu His Lys
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asp Arg Ser Asn Leu Ser Arg
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Arg Ser Thr Leu Lys Ser
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Leu Ser Gln Asp Leu Asn Arg
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Ser Ser Asn Leu Ala Arg
1               5

<210> SEQ ID NO 95
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 95

Arg Ser Asp Asn Leu Ser Glu
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Ser Lys Thr Arg Lys Asn
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Leu Thr His Leu Asn Ser
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Lys Leu Tyr Leu Asn Asn
1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asp Arg Ser Asn Leu Thr Arg
1               5

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Tyr Arg Trp Leu Arg Asn Ser
1               5

```
<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Asp Ser Gly Gly Leu Ser Lys
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Trp Arg Gly Asp Arg Val Lys
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gln Arg Gln Asn Leu Val Asn
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Ser Asp Asn Leu Ser Val
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Ser Ala Asp Leu Ser Arg
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106
```

Gln Gly Gln Asp Arg His Lys
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Tyr Cys Cys Leu Thr Asn
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Ser Asp Asn Leu Ser Thr
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Phe His Ser Cys Leu Ser Ala
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Asn Ser Asp Arg Thr Lys
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Ser Ala Asn Leu Ala Arg
1               5

<210> SEQ ID NO 112
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 112

Asp Arg Ser His Leu Ala Arg
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Arg Pro Tyr Thr Leu Arg Leu
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

His Arg Ser Asn Leu Asn Lys
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Val Ser Asn Asn Leu Ala Cys
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Arg Asn Phe Ser Leu Thr Met
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

His Lys Ser Ala Arg Ala Ala
1               5
```

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Tyr Asp Tyr Gly Arg Tyr Thr
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Thr Ser His Asn Arg Asn Ala
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Arg Ser Asp Ala Leu Thr Gln
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ile Arg Ser Asn Leu Leu Ala
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Leu Arg His Asn Leu Arg Ala
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 123

Ala Arg Ser Thr Arg Ile Thr
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Asn Ala His Arg Ile Asn
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Ser Asp Ser Leu Ser Val
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Thr Ser Ser Asn Arg Lys Thr
1               5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gln Lys Val Thr Leu Ala Ala
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Arg Ser Asp Asp Leu Ser Arg
1               5

<210> SEQ ID NO 129
<211> LENGTH: 7
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 129

Gln Ser Ala His Leu Lys Ala
1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Thr Gln Gly Leu Gly Ile
1               5

<210> SEQ ID NO 131
<211> LENGTH: 47
<212> TYPE: DNA
<213> ORGANISM: Homo sapiens

<400> SEQUENCE: 131
aagctgtgct gaccatcgac gagaaaggga ctgaagctgc tggggcc                  47

<210> SEQ ID NO 132
<211> LENGTH: 245
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
gcttcctggg aggtgtccac gtgagccttg ctcgaggcct gggatcagcc ttacaacgtg    60
tctctgcttc tctccctcc aggccgtgca taaggctgtg ctcaccattg acgagaaagg    120
gactgaagct gctggggcca tgttttaga ggccataccc atgtctatcc ccccgaggt     180 caagttcaac aaaccctttg tcttcttaat gattgaacaa ataccaagt ctcccctctt    240 catgg                                                              245

<210> SEQ ID NO 133
<211> LENGTH: 95
<212> TYPE: DNA
<213> ORGANISM: Unknown
<220> FEATURE:
<223> OTHER INFORMATION: Description of Unknown:
      Partial sequence of TTR gene

<400> SEQUENCE: 133
gacaggatgg cttcccttcg actcttcctc ctttgcctcg ctggactggt atttgtgtct    60
gaagctggcc ccgcggtgag tgatcctgtg agcga                              95

<210> SEQ ID NO 134
<211> LENGTH: 95
<212> TYPE: DNA
<213> ORGANISM: Unknown
<220> FEATURE:
<223> OTHER INFORMATION: Description of Unknown:
      Partial sequence of TTR gene
```

<400> SEQUENCE: 134
tcgctcacag gatcactcac cgcggggcca gcttcagaca caaataccag tccagcgagg    60
caaaggagga agagtcgaag ggaagccatc ctgtc    95

<210> SEQ ID NO 135
<211> LENGTH: 147
<212> TYPE: DNA
<213> ORGANISM: Unknown
<220> FEATURE:
<223> OTHER INFORMATION: Description of Unknown:
      Partial sequence of TTR gene

<400> SEQUENCE: 135
gtgcccaggg tgctggagaa tccaaatgtc ctctgatggt caaagtcctg gatgctgtcc    60
gaggcagccc tgctgtagac gtggctgtaa aagtgttcaa aaagacctct gagggatcct   120
gggagccctt tgcctctggg taagctt    147

<210> SEQ ID NO 136
<211> LENGTH: 147
<212> TYPE: DNA
<213> ORGANISM: Unknown
<220> FEATURE:
<223> OTHER INFORMATION: Description of Unknown:
      Partial sequence of TTR gene

<400> SEQUENCE: 136
aagcttaccc agaggcaaag ggctcccagg atccctcaga ggtcttttg aacactttta    60 cagccacgtc tacagcaggg ctgcctcgga cagcatccag gactttgacc atcagaggac   120
atttggattc tccagcaccc tgggcac    147

<210> SEQ ID NO 137
<211> LENGTH: 152
<212> TYPE: DNA
<213> ORGANISM: Unknown
<220> FEATURE:
<223> OTHER INFORMATION: Description of Unknown:
      Partial sequence of TTR gene

<400> SEQUENCE: 137
ccctccagga agaccgcgga gtctggagag ctgcacgggc tcaccacaga tgagaagttt    60
gtagaaggag tgtacagagt agaactggac accaaatcgt actggaagac acttggcatt   120
tccccgttcc atgaattcgc ggatgtaagt gg    152

<210> SEQ ID NO 138
<211> LENGTH: 152
<212> TYPE: DNA
<213> ORGANISM: Unknown
<220> FEATURE:
<223> OTHER INFORMATION: Description of Unknown:
      Partial sequence of TTR gene

<400> SEQUENCE: 138
ccacttacat ccgcgaattc atggaacggg gaaatgccaa gtgtcttcca gtacgatttg    60
gtgtccagtt ctactctgta cactccttct acaaacttct catctgtggt gagcccgtgc   120
agctctccag actccgcggt cttcctggag gg    152

<210> SEQ ID NO 139
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 139

Leu Arg Gly Ser Gln Leu Val Lys Ser
1               5

<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ser Gly Thr Pro His Glu Val Gly Val Tyr Thr Leu
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ser Gly Ala Gln Gly Ser Thr Leu Asp Phe
1               5                   10

<210> SEQ ID NO 142
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Leu Arg Gly Ser Tyr Ala Pro Met Pro Pro Leu Ala Leu Ala Ser Pro
1               5                   10                  15

<210> SEQ ID NO 143
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gtggaggctg cccggcacct acgtggtg                                         28

<210> SEQ ID NO 144
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gtggtgctga aggaggagac ccaccgct                                         28

<210> SEQ ID NO 145
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gtgggacatc gcaggctgct gcccacgt                                           28

<210> SEQ ID NO 146
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ggggtggtga cttaccagcc acgtgggc                                           28

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Thr Gly Gln Thr Leu Arg Gly
1               5

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Lys Gln Tyr Leu Ile Lys
1               5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gln Ser Gly His Leu Gln Arg
1               5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Tyr Lys Trp Asp Leu Asn Asn
1               5
```

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gln Lys Arg Asn Arg Thr Lys
1               5

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Arg Ser Asp Asn Leu Ser Ala
1               5

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Arg Asn Asn Asp Arg Lys Thr
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Asp Arg Ser Asp Leu Ser Arg
1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Arg Ser His His Leu Lys Ala
1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 156

Asp Arg Ser Thr Arg Thr Lys
1               5

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Arg Arg Asp Thr Leu Leu Asp
1               5

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gln Ser Ala Val Leu Pro Gly
1               5

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Leu Lys Gln Asn Leu Asp Ala
1               5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Glu Arg Gly Thr Leu Ala Arg
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ser His Leu Gly Leu Thr Ile
1               5

<210> SEQ ID NO 162
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Arg Ser Asn Asp Arg Lys Lys
1               5

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gln Asn Ala Thr Arg Ile Asn
1               5

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Arg Ser Asn Asp Arg Ile Lys
1               5

<210> SEQ ID NO 165
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
tcgggagatt gagggcaggg tcaccatc                                      28

<210> SEQ ID NO 166
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ggcacgctgt tgaagtcggt gatggtga                                      28

<210> SEQ ID NO 167
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
cagagcatcc catggaacct ggagcgaa                                      28
```

```
<210> SEQ ID NO 168
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
ctggtgccat gctgggataa ttcgctcc                                       28

<210> SEQ ID NO 169
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gagctgcggc agaggctgat ccacttct                                       28

<210> SEQ ID NO 170
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ttgatgacgt ctttggtaga gaagtgga                                       28

<210> SEQ ID NO 171
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gctaagtgca tggctgtctg gttctgta                                       28

<210> SEQ ID NO 172
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
cacatggggc aacttcaggg cctacaga                                       28

<210> SEQ ID NO 173
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
gtgggacctc acaggctgct gcccacgt                                       28

<210> SEQ ID NO 174
```

<211> LENGTH: 47
<212> TYPE: DNA
<213> ORGANISM: Homo sapiens

<400> SEQUENCE: 174
ggccccagca gcttcagtcc ctttctcgtc gatggtcagc acagctt         47

<210> SEQ ID NO 175
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ggggtggtga ctcaccggcc acgtgggc         28

<210> SEQ ID NO 176
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
aggatggaga ttatgaagag ctgatgct         28

<210> SEQ ID NO 177
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
tcctcctggg acgggagggc gagcatca         28

<210> SEQ ID NO 178
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
gtggtgctga tggaggagac ccagaggc         28

<210> SEQ ID NO 179
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ctggaggctg ccaggaacct acattgtg         28

<210> SEQ ID NO 180
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 180

Arg Ser Asp His Leu Ser Ala
1               5

<210> SEQ ID NO 181
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ser Tyr Trp Ser Arg Thr Val
1               5

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gln Asn Ala His Arg Lys Thr
1               5

<210> SEQ ID NO 183
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gln Ser Ala His Arg Lys Asn
1               5

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gln Ser Ser Asp Leu Thr Arg
1               5

<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Thr Ser Gly Ser Leu Thr Arg
1               5

```
<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Asp Arg Ser Asn Arg Asn Gln
1               5

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

His Gly Gln Thr Leu Asn Glu
1               5

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Arg Ser Asp Val Leu Ser Asn
1               5

<210> SEQ ID NO 189
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Asp Arg Ser Thr Arg Ile Thr
1               5

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Leu Ser Trp Asn Leu Leu Thr
1               5

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191
```

Leu Gln Gln Thr Leu Ala Asp
1               5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gln Ser Ala Asn Arg Thr Lys
1               5

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Arg Ser Asp Ala Leu Ser Glu
1               5

<210> SEQ ID NO 194
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Arg Ser Ser Thr Arg Lys Thr
1               5

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Arg Lys Tyr Ser Leu Arg Val
1               5

<210> SEQ ID NO 196
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Leu Ser Gln Asp Leu Asn Arg
1               5

<210> SEQ ID NO 197
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 197

Gln Asn Val Ser Arg Pro Arg
1               5

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ser Leu Thr Tyr Leu Pro Thr
1               5

<210> SEQ ID NO 199
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Thr Ser Ala Asn Leu Ser Arg
1               5

<210> SEQ ID NO 200
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Arg Trp Gln Tyr Leu Pro Thr
1               5

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Arg Lys Asp Ala Leu Val Ala
1               5

<210> SEQ ID NO 202
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Arg Ser His Ser Leu Leu Arg
1               5
```

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Arg Arg Asp Ala Leu Leu Met
1               5

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ala Lys Trp Asn Leu Asp Ala
1               5

<210> SEQ ID NO 205
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

His Ala Ser Thr Leu Gln Asn
1               5

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Arg Ser Asp Asn Leu Arg Glu
1               5

<210> SEQ ID NO 207
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

His Arg Ser Thr Arg Asn Arg
1               5

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 208

Arg Ser Asp Asn Leu Ser Gln
1               5

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ala Ser Asn Asp Arg Lys Lys
1               5

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ala Ser Lys Thr Arg Thr Asn
1               5

<210> SEQ ID NO 211
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Leu Lys Gln His Leu Thr Arg
1               5

<210> SEQ ID NO 212
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Asp Arg Ser His Leu Ser Arg
1               5

<210> SEQ ID NO 213
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Arg Ser Ala Asp Leu Thr Arg
1               5

<210> SEQ ID NO 214
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 214

Arg Ser Asp His Leu Thr Gln
1               5

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gln Ser His His Arg Lys Thr
1               5

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ser Pro Ser Ser Arg Arg Thr
1               5

<210> SEQ ID NO 217
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Asn Ser Ser Ser Arg Ile Lys
1               5

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

His Arg His His Leu Ile Arg
1               5

<210> SEQ ID NO 219
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Arg Gly Asp Arg Arg Asn Lys
1               5
```

<210> SEQ ID NO 220
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
ctgccttgct ggactggtat ttgtgtct                                        28

<210> SEQ ID NO 221
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
gagcagacga tgagaagcca tcctgcca                                        28

<210> SEQ ID NO 222
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
tcttactgga aggcacttgg catctccc                                        28

<210> SEQ ID NO 223
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

His Arg Lys Ser Leu Ser Arg
1               5

<210> SEQ ID NO 224
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ala His Gly Ala Arg Trp Asn
1               5

<210> SEQ ID NO 225
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

```
Arg Arg Trp Ser Leu Ser Val
1               5

<210> SEQ ID NO 226
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Arg Ser Asp Ala Arg Thr Asn
1               5

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Leu Lys Trp Asn Leu Arg Thr
1               5

<210> SEQ ID NO 228
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Tyr Thr Tyr Ser Leu Ser Glu
1               5

<210> SEQ ID NO 229
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Arg Lys Asp Gln Leu Val Ala
1               5

<210> SEQ ID NO 230
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Gln Arg Thr Pro Arg Ala Lys
1               5

<210> SEQ ID NO 231
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 231

Arg Ser Asp Ala Leu Thr Gln
1               5

<210> SEQ ID NO 232
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
acttgctgca tatgtggcta aagcaata                                              28

<210> SEQ ID NO 233
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
tcccagctga tagatgggtc tattgctt                                              28

<210> SEQ ID NO 234
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gln Leu Gly Asn Leu His Thr
1               5

<210> SEQ ID NO 235
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Arg Ser Asp Val Leu Ser Thr
1               5

<210> SEQ ID NO 236
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ala Ser Gly Asn Leu Leu Asn
1               5

<210> SEQ ID NO 237
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Arg Lys Tyr Tyr Leu Ala Lys
1               5

<210> SEQ ID NO 238
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gln Ser Ala His Leu Val Cys
1               5

<210> SEQ ID NO 239
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ctgctccttg cacgaaggtc acattcag                                      28

<210> SEQ ID NO 240
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
ttgactttga agggaagaa ctgaatgt                                       28

<210> SEQ ID NO 241
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
gcagagtgct ggaaaatatc catggggc                                      28

<210> SEQ ID NO 242
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ccgctgagtt cacaggttgc cccatgga                                      28

<210> SEQ ID NO 243
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
ttgtcggtct tagagatatt aaagttgg                                          28

<210> SEQ ID NO 244
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
aaggacttga tatgagaggg tccaactt                                          28

<210> SEQ ID NO 245
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ttcacttgca ggctgacctg ccatggcc                                          28

<210> SEQ ID NO 246
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
tctttagggg agtggccatg gcaggtca                                          28

<210> SEQ ID NO 247
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
tgcatgccat aggtgatcct agttgggg                                          28

<210> SEQ ID NO 248
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
gggagccatc tgtggataac cttaagga                                          28

<210> SEQ ID NO 249
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
acggcgagaa agctgaacag caggcacc                                           28

<210> SEQ ID NO 250
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
ggcacctggg gtgaaaagtg cacatctt                                           28

<210> SEQ ID NO 251
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Asp Arg Ser Ala Leu Ser Arg
1               5

<210> SEQ ID NO 252
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ile Arg Ser Thr Leu Arg Asp
1               5

<210> SEQ ID NO 253
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

His Arg Ser Ser Leu Arg Arg
1               5

<210> SEQ ID NO 254
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Arg Leu Tyr Thr Leu His Lys
1               5
```

<210> SEQ ID NO 255
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Tyr Ser Trp Thr Leu Arg Asp
1               5

<210> SEQ ID NO 256
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Ser Thr Ala Ala Leu Ser Tyr
1               5

<210> SEQ ID NO 257
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Arg Ser Asp Thr Leu Ser Gln
1               5

<210> SEQ ID NO 258
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Ala Ser Ala Asn Arg Thr Lys
1               5

<210> SEQ ID NO 259
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Leu Arg Gln Asp Leu Lys Arg
1               5

<210> SEQ ID NO 260
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 260

Arg Gln Trp Ser Leu Arg Ile
1               5

<210> SEQ ID NO 261
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Asp Arg Ser Asn Arg Thr Thr
1               5

<210> SEQ ID NO 262
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Arg Ser Asp Ser Leu Leu Arg
1               5

<210> SEQ ID NO 263
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Gln Arg Cys His Leu Thr Lys
1               5

<210> SEQ ID NO 264
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

His Asn His Asp Leu Arg Asn
1               5

<210> SEQ ID NO 265
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gln Lys Trp Pro Arg Asp Ser
1               5

<210> SEQ ID NO 266
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 266

Leu Arg Phe Asn Leu Arg Asn
1               5

<210> SEQ ID NO 267
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Thr Asn Ser Asn Arg Lys Arg
1               5

<210> SEQ ID NO 268
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Leu Lys Gln Asp Arg Arg Lys
1               5

<210> SEQ ID NO 269
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Ile Lys His Asp Leu His Arg
1               5

<210> SEQ ID NO 270
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gln Ser Gly Asn Arg Thr Thr
1               5

<210> SEQ ID NO 271
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Leu Arg His Gln Leu Lys Ser
1               5
```

```
<210> SEQ ID NO 272
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Gln Arg Ser Asn Leu Val Arg
1               5

<210> SEQ ID NO 273
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Asp Thr Arg Asn Leu Arg Ala
1               5

<210> SEQ ID NO 274
<211> LENGTH: 4
<212> TYPE: PRT
<213> ORGANISM: Homo sapiens

<400> SEQUENCE: 274

Ile Asp Glu Lys
1
```

US 10,960,085 B2

MODULATION OF LIVER GENES

CROSS-REFERENCE TO RELATED APPLICATIONS

The present application claims the benefit of U.S. Provisional Application No. 62/384,428 filed Sep. 7, 2016, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Nov. 14, 2017, is named 83250157SL.txt and is 60,819 bytes in size.

TECHNICAL FIELD

The present disclosure is in the field of gene therapy, particularly knock-out of disease related endogenous genes and targeted delivery of transgene-encoding constructs to the liver for expression of inhibitory proteins.

BACKGROUND

Gene therapy can be used to genetically engineer a cell to have one or more inactivated genes and/or to cause that cell to express a product not previously being produced in that cell (e.g., via transgene insertion and/or via correction of an endogenous sequence). Examples of uses of transgene insertion include the insertion of one or more genes encoding one or more novel therapeutic proteins, insertion of a coding sequence encoding a protein that is lacking or dysfunctional in the cell or in the individual, insertion of a wild type gene or fragment thereof in a cell containing a mutated gene sequence, and/or insertion of a sequence that encodes a structural nucleic acid such as a microRNA or siRNA. Examples of useful applications of 'correction' of an endogenous gene sequence include alterations of disease-associated gene mutations, alterations in sequences encoding splice sites, alterations in regulatory sequences and/or targeted alterations of sequences encoding structural characteristics of a protein.

Hepatic gene transfer provides an effective means of delivering transgenes to a subject for treatment and/or prevention of various disorders, including hemophilias and lysosomal storage disorders. See, e.g., U.S. Pat. No. 9,150,847 and U.S. Publication Nos. 20170119906, 20130177983 and 20140017212. Vectors specific for liver-directed gene therapy have also been described. See, e.g., WO 2014064277; WO 2009130208; PCT Publication No. WO 2017/074526; EP 2451474B1, Chuah et al., (2014) *Molecular Therapy,* 22, 1605-1613; and Nair et al. (2014) *Blood* 123:3195-3199. These vectors can include the wild-type mouse minute virus (MVM) intron sequence. See, e.g., Haut and Pintel (1998) *J. Virol.* 72:1834-1843; Haut and Pintel (1998) *Virol.* 258:84-94. Thus, liver-directed gene therapy holds promise for treatment or prevention of a number of diseases.

Artificial transcription factors and nucleases, such as engineered zinc finger protein transcription factors (ZFP-TFs), transcription-activator like effector transcription factors (TALE-TFs), CRISPR/Cas transcription factors (CRISPR-TFs), zinc finger nucleases (ZFN), transcription-activator like effector nucleases (TALENs), the CRISPR/Cas system with an engineered crRNA/tracr RNA ('single guide RNA'), also referred to as RNA guided nucleases, and/or nucleases based on the Argonaute system (e.g., from *T. thermophilus*, known as 'TtAgo', (Swarts et al (2014) *Nature* 507(7491): 258-261), comprise DNA binding domains (nucleotide or polypeptide) associated with or operably linked to transcriptional regulatory domains (for transcription factors) or cleavage domains (for nucleases), and have been used for modulation of gene expression and targeted alteration of genomic sequences. For example, artificial nucleases have been used to insert exogenous sequences, inactivate one or more endogenous genes, create organisms (e.g., crops) and cell lines with altered gene expression patterns, and the like. See, e.g., U.S. Pat. Nos. 9,255,250; 9,200,266; 9,045,763; 9,005,973; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983 and 20130177960 and 20150056705. Similarly, artificial transcription factors targeted to particular sequences have been used to activate or repress endogenous gene expression. See, e.g., U.S. Pat. Nos. 9,234,016; 8,563,314 and 8,841,260; Perez-Pinera et al. (2013) *Nature Methods* 10:973-976. Clinical trials using these engineered transcription factors containing zinc finger proteins have shown that these novel transcription factors are capable of treating various conditions. (see, e.g., Yu et al. (2006) *FASEB J.* 20:479-481).

However, there remains a need for the treatment or prevention of a number of diseases that can be addressed through liver-directed gene therapy. Such diseases include TTR-Mediated Amyloidosis, A1AT Deficiency, Hereditary Angioedema, Familial Hypercholesterolemia/Static resistant hypercholesterolemia and Hyperxoaluria.

SUMMARY

The present invention describes compositions and methods for modulating the expression of the PCSK9, TTR, SERPINA1, KLKB1 and/or HAO1 genes in the liver and/or for modulating the amount and/or activity of their gene products in the serum following expression of a specific inhibitor of the gene product from a liver cell. Modulation of the gene expression for these genes can be accomplished via genetic modification (e.g., cleavage which results in sequence modifications to the gene resulting in gene knock-out) of the PCSK9, TTR, SERPINA1, KLKB1 and/or HAO1 genes using one or more engineered nucleases and/or via introduction of a modulator (activator or inhibitor) of PCSK9, TTR, SERPINA1, KLKB1 and/or HAO1 gene expression such as a transcription factor that regulates (turns off or downregulates, or turns on or up-regulates) expression of the PCSK9, TTR, SERPINA1, KLKB1 and/or HAO1 genes. The modulator of gene expression may either act by direct action on the PCSK9, TTR, SERPINA1, KLKB1 and HAO1 genes and/or by indirect action (e.g., activation of PCSK9, TTR, SERPINA1, KLKB1 and/or HAO1 inhibitors).

Additionally, provided herein are methods and compositions for deleting (inactivating) or repressing the PCSK9, TTR, SERPINA1, KLKB1 and/or HAO1 genes to produce a PCSK9, TTR, SERPINA1, KLKB1 or HAO1 null cell, stem cell, tissue or whole organism. Modulation of PCSK9, TTR, SERPINA1, KLKB1 and/or HAO1 genes can also be achieved by inhibition of the PCSK9, TTR, SERPINA1, KLKB1 and/or HAO1 gene products, for example by introduction of a transgene into a liver cell that encodes the inhibitor, which may be expressed extra-chromosomally (episomally) or may be integrated into the genome of the liver cell (e.g., via nuclease-mediated targeted integration, for example into an albumin locus). In some embodiments, the transgene encodes an antibody or polypeptide capable of inhibiting the PCSK9, TTR, SERPINA1, KLKB1 and/or HAO1 gene products. In some aspects, the inhibitor is an inhibitory nucleic acid such as an RNAi.

Thus, in one aspect, described herein are cells in which the expression of a PCSK9, TTR, SERPINA1, KLKB1 and/or HAO1 gene is modulated. In some embodiments, the cells comprise a knock-out of a PCSK9, TTR, SERPINA1, KLKB1 and/or HAO1 gene, for example a cell in which PCSK9, TTR, SERPINA1, KLKB1 or HAO1 is inactivated (partially or fully) using one or more engineered nucleases to knockout a PCSK9, TTR, SERPINA1, KLKB1 and/or HAO1 gene. In other embodiments, cells are described that comprise an engineered transcription factor (TF) such that the expression of a PCSK9, TTR, SERPINA1, KLKB1 and/or HAO1 gene is modulated. In some embodiments, the cells are liver cells. Further described are cells in which the expression of a PCSK9, TTR, SERPINA1, KLKB1 and/or HAO1 gene is modulated (e.g., via nuclease-mediated inactivation and/or using one or more engineered TFs) and wherein the cells are further engineered to comprise a least one exogenous transgene or an additional knock out of at least one endogenous gene or combinations thereof. The exogenous transgene may be integrated into a PCSK9, TTR, SERPINA1, KLKB1 or HAO1 gene and/or may be integrated into a safe harbor locus. In some cases, the exogenous transgene encodes a PCSK9, TTR, SERPINA1, KLKB1 and/or HAO1 inhibitor (e.g., a PCSK9, TTR, SERPINA1, KLKB1 and/or HAO1 polypeptide inhibitors such as an antibody and/or a PCSK9, TTR, SERPINA1, KLKB1 and/or HAO1 inhibitor RNA molecule).

In certain embodiments, the cells described herein comprise a modification (e.g., deletion and/or insertion) to a PCSK9, TTR, SERPINA1, KLKB1 and/or HAO1 gene sequence in which the modification is made using a nuclease that binds to a sequence within the selected target gene. In certain embodiments, the DNA-binding domain (e.g., ZFP, TALE, single guide RNA, etc.) of the nuclease used for modification of the indicated target gene binds to a target site of 9, 10, 11, 12, 13, 14, 15, 16, 17, 18, 19, 20, 21 or even more base pairs) as shown in herein (e.g., Tables 1, 3, 5, 7, 11, 13, 14, and 16). The nuclease target sites may be contiguous or non-contiguous sequences. In certain embodiments, paired nucleases used. Nuclease-mediated modification as described herein can result in modifications (insertions and/or deletions) that are within or near nuclease(s) binding and/or cleavage site(s), including but not limited to, modifications to sequences within 1-300 (or any number of base pairs therebetween) base pairs upstream, downstream and/or including 1 or more base pairs of the site(s) of cleavage and/or binding site; modifications within 1-100 base pairs (or any number of base pairs therebetween) of including and/or on either side of the binding and/or cleavage site(s); modifications within 1 to 50 base pairs (or any number of base pairs therebetween) including and/or on either side of the binding and/or cleavage site(s); and/or modifications to one or more base pairs within the nuclease binding site and/or cleavage site. In certain embodiments, the modification is within or near to the target sites shown herein, including but not limited to modifications in the genome of the cell within, between (e.g., for paired target sites) or near (e.g., 1-50 nucleotides or more (or any number of nucleotides)) the target sites shown herein (e.g., Tables 1, 3, 5, 7, 11, 13, 14, and 16).

In another aspect, the compositions (modified cells) and methods described herein can be used, for example, in the treatment and/or prevention or amelioration of a disorder. The methods typically comprise (a) cleaving or down regulating expression of an endogenous PCSK9, TTR, SERPINA1, KLKB1 or HAO1 gene in a cell (e.g. a hepatocyte) using a nuclease (e.g., ZFN or TALEN) or RNA-guided nuclease system such as CRISPR/Cas with an engineered crRNA/tracr RNA, or using an engineered transcription factor (e.g. ZFP-TF, TALE-TF or Cas9-TF) such that the PCSK9, TTR, SERPINA1, KLKB1 and/or HAO1 gene is inactivated or down modulated; thereby treating or preventing the disorder.

Also described herein are artificial nucleases and/or transcription factors comprising a DNA-binding domain (e.g., ZFP, TALE, sgRNA, etc.) that binds to a target site within a liver-specific gene (e.g., PCSK9, TTR, SERPINA1, KLKB1 and/or HAO1) and a functional domain (e.g., nuclease/cleavage domain in the case of nuclease and transcriptional activation or repression domain in the case of transcription factors). The DNA-binding domain may bind to any sequence within the target sequence to effect modulation of the gene. In certain embodiments, the DNA-binding domain binds to a target site of 12 or more (12, 13, 14, 15, 16, 17, 18, 19, 20, 21, 22 or more) nucleotides of the target sites as shown in the appended Tables. The bound nucleotides may be contiguous or non-contiguous. Binding of the DNA-binding domain of an artificial transcription factor as described herein to its target site then modulates expression of the target gene via up-regulation or down-regulation. Similarly, binding of the DNA-binding domain of an artificial nuclease as described herein (e.g., a DNA-binding domain in association with a cleavage/nuclease domain) causes a break (single- or double-stranded) in the target gene that results in modification via NHEJ mediated repair (insertions and/or deletions known as "indels"), NHEJ-mediated integration of a donor (e.g., via end capture) and/or homology-directed repair (e.g., integration of a donor with homology arms into the break). The site of cleavage and/or modification may be within or adjacent to (e.g., 1-50 nucleotides, including, 1, 2, 3, 4, 5, 6, 7, 8, 9, 10 or more) the nuclease target site or may be between paired target sites.

The nuclease(s), transcription factor(s) and/or transgenes can be introduced as mRNA, in protein form and/or as a DNA sequence encoding one or more components of the nuclease(s), TFs and/or transgenes. In one aspect, provided herein are zinc finger nucleases (ZFNs), TALENs and/or CRISPR/Cas systems that cleave a PCSK9, TTR, SERPINA1, KLKB1 and/or HAO1 gene. In other embodiments, provided herein are ZFP-TFs, TALE-TFs and Cas9-TFs that modulate expression of a PCSK9, TTR, SERPINA1, KLKB1 or HAO1 gene. In certain embodiments, the ZFPs, TALEs or single guide RNAs (sgRNA) of a CRISPR/Cas system of the nucleases or transcription factors bind to target sites in a human PCSK9, TTR, SERPINA1, KLKB1 or HAO1 gene. The zinc finger proteins may include 1, 2, 3, 4, 5, 6 or more zinc fingers, each zinc finger having a recognition helix that specifically contacts a target subsite in the target gene. In certain embodiments, the zinc finger proteins comprise 4 or 5 or 6 fingers (designated F1, F2, F3, F4, F5 and F6 and ordered F1 to F4 or F5 or F6 from N-terminus to C-terminus). In other embodiments, the single guide RNAs may bind to a target site in the PCSK9, TTR, SERPINA1, KLKB1 and/or HAO1 gene.

Any of the nucleases described herein may further comprise a cleavage domain and/or a cleavage half-domain (e.g., a wild-type or engineered FokI cleavage half-domain). Thus, in any of the ZFNs and/or TALENs described herein, the nuclease domain may comprise a wild-type nuclease domain or nuclease half-domain (e.g., a FokI cleavage half domain). In other embodiments, the ZFNs and/or TALENs comprise engineered nuclease domains or half-domains, for example engineered FokI cleavage half domains that form obligate heterodimers. See, e.g., U.S. Patent Publication No. 20080131962. In some embodiments, the ZFNs may further comprise modification to the ZFP backbone to decrease non-specific DNA interactions. In further embodiments, the FokI domains in the engineered ZFNs, TALENs, or dCas-FokI fusions comprise mutations to disrupt non-specific interactions between the FokI domain and the DNA molecule (see U.S. application Ser. No. 15/685,580). In still further embodiments, the ZFNs, TALENs and/or RNA-guided CRISPR/Cas systems act as nickases. In some instances, double strand cleavage is achieved using two pairs of nickases (e.g. U.S. Pat. No. 9,200,266). Any of the transcription factors described herein may further comprise a transcriptional activation or repression domain.

In another aspect, described herein are methods of inactivating a PCSK9, TTR, SERPINA1, KLKB1 and/or HAO1 gene in a cell by introducing one or more proteins, polynucleotides, systems and/or vectors into the cell as described herein. In any of the methods described herein the nucleases may induce targeted mutagenesis, deletions of cellular DNA sequences, and/or facilitate targeted recombination at a predetermined chromosomal locus. Thus, in certain embodiments, the nucleases delete or insert one or more nucleotides of the target gene. In some embodiments the PCSK9, TTR, SERPINA1, KLKB1 and/or HAO1 gene is inactivated by nuclease cleavage followed by non-homologous end joining. In other embodiments, a genomic sequence in the target gene is replaced, for example using a nuclease (or vector encoding said nuclease) as described herein and a "donor" sequence that is inserted into the gene following targeted cleavage with the nuclease. The donor sequence may be present in the nuclease vector, present in a separate vector (e.g., AAV, Ad or LV vector) or, alternatively, may be introduced into the cell using a different nucleic acid delivery mechanism.

In certain embodiments, the cell comprising the PCSK9, TTR, SERPINA1, KLKB1 and/or HAO1 modulations described herein (e.g., down-regulation via a PCSK9, TTR, SERPINA1, KLKB1 or HAO1 targeted nuclease and/or transcription factor) further comprises one or more additional genomic modification, for example, an integrated exogenous sequence (into a cleaved PCSK9, TTR, SERPINA1, KLKB1 or HAO1, or other gene, for example a safe harbor gene or locus). The exogenous sequence may be introduced via a vector (e.g. Ad, AAV, LV), or by using a technique such as electroporation. In further embodiments, the additional modification comprises introducing a wild-type cDNA copy of PCSK9, TTR, SERPINA1, KLKB1 and/or HAO1 into the cell where an endogenous mutant copy in the cell has been knocked out by any of the methods described herein. In some aspects, the wildtype cDNA copy of PCSK9, TTR, SERPINA1, KLKB1 and/or HAO1 may comprise silent gene modifications such that the cDNA is not subject to cleavage by the targeted nucleases. In some embodiments, the cDNA copy is integrated into the genome, while in other embodiments, the cDNA copy is maintained extrachromosomally.

In some aspects, the PCSK9, TTR, SERPINA1, KLKB1 or HAO1 modulated cells further comprise a gene encoding an exogenous transgene that inhibits PCSK9, TTR, SERPINA1, KLKB1 and/or HAO1 activity. In other aspects, described herein are cells lacking PCSK9, TTR, SERPINA1, KLKB1 and/or HAO1 gene modification(s) but comprising a construct for the expression of a transgene that encodes a PCSK9, TTR, SERPINA1, KLKB1 and/or HAO1 inhibitory activity. In some embodiments, the inhibitory transgene encodes an antibody that inhibits the proteins encoded by PCSK9, TTR, SERPINA1, KLKB1 and/or HAO1. In other embodiments, the inhibitory transgene encodes an inhibitory nucleic acid (e.g. RNAi, shRNA) that inhibits PCSK9, TTR, SERPINA1, KLKB1 and/or HAO1 expression. In some embodiments, the inhibitory RNA is a double stranded RNA (U.S. Pat. No. 9,249,415). Also described are cells produced by the methods described herein, including cells descended from these cells (e.g., genetically modified cells descended from the cells modified as described herein). In certain embodiments, the genetic modifications comprise one or more insertions and/or deletions within a PCSK9, TTR, SERPINA1, KLKB1 and/or HAO1 gene, including, but not limited to, insertions and/or deletions within the target sites disclosed herein and/or between paired target sites as described herein.

In one aspect, described herein is a polynucleotide expression construct comprising a sequence encoding a transgene that encodes one or more modulators of PCSK9, TTR, SERPINA1, KLKB1 and/or HAO1 gene expression (e.g., the engineered nuclease and/or engineered transcription factor targeted to PCSK9, TTR, SERPINA1, KLKB1 and/or HAO1). In certain embodiments, the polynucleotide expression construct further comprises an enhancer sequence (e.g., a wild-type or mutated Serpin1 enhancer), a promoter sequence (e.g., a transthyretin minimal promoter (TTRm) promoter), and the transgene and, optionally, a polyadenylation sequence (e.g., a synthetic polyadenylation sequence (SPA) and/or a signal peptide (SP) (see U.S. Patent Publication No. US-2017-0119906-A1). In certain embodiments, the expression construct further comprises an intron sequence (e.g., wild-type MVM or a mutated MVM sequence and/or chimeric intron). In certain embodiments, the expression constructs comprise in 5' to 3' orientation, an enhancer sequence, a promoter sequence, an intronic sequence, a transgene (optionally comprising a signal peptide), and a polyadenylation signal.

The expression cassette encoding the gene modulators as described herein may be included in any viral or non-viral vector, including but not limited to plasmid vectors, adenovirus vector, retroviral vectors and adeno associated vector (AAV). In a preferred embodiments, the expression construct is carried on an AAV construct and further comprises 5' and 3' ITRs flanking the expression constructs as described herein. Optionally, spacer molecules are also included between one or more of the components of the expression construct, for example, between the 5' ITR and the enhancer and/or between the polyadenylation signal and the 3' ITR.

In some embodiments, the one or more transgenes include sequences encoding gene modulators such as engineered nucleases (e.g. ZFNs, TALENs, TtAgo and CRISPR/Cas systems). In other embodiments, the gene modulating transgenes include sequences encoding engineered transcription factors (e.g. ZFP-TFs, TALE-TFs, CRISPR/Cas-TF systems). In certain embodiments, the gene modulators (e.g., nucleases and/or transcription factors) are targeted to PCSK9, TTR, SERPINA1, KLKB1 and/or HAO1.

In certain aspects, the polynucleotides as described herein are introduced into a cell such that they are maintained episomally while driving expression of the PCSK9, TTR, SERPINA1, KLKB1 and/or HAO1 gene-modulating transgene. In other aspects, the expression constructs are randomly integrated into the genome of the cell into which they are introduced. In further aspects the expression constructs driving transgene expression are integrated into a genome by nuclease-mediated targeted integration.

In still further aspects, described herein are cells comprising any of the gene modulators disclosed herein (polynucleotides and/or proteins) as well as cells comprising any genetic modifications made by the gene modulators described herein. Also provided are cells descended from these cells, for example cells descended (including but not limited to cells differentiated from stem or progenitor cells) from genetically modified cells as described herein, in which the cells no longer comprise the gene modulator(s). The isolated cells may be introduced into the subject (ex vivo cell therapy) or cells as described herein (e.g., genetically modified cells) may be modified when it is part of the subject (in vivo).

In further aspects, described herein are methods for expressing one or more transgenes (modulators of PCSK9, TTR, SERPINA1, KLKB1 and/or HAO1) in a liver cell, the methods comprising introducing one or more expression constructs as described herein into the cell such that the transgene is expressed in the cell. In certain embodiments, the expression construct is carried on a viral or non-viral vector, preferably an AAV vector (for example AAV2, AAV6, AAV8, AAV2/6, or AAV2/8).

In another aspect, provided herein is a method of expressing one or more transgenes (modulators of PCSK9, TTR, SERPINA1, KLKB1 and/or HAO1) in a live animal, the methods comprising administering one or more expression cassettes as described herein to the live animal. In certain embodiments, the expression cassettes are administered to the liver of the live animal. In certain embodiments, the expression construct is carried on a viral or non-viral vector, preferably an AAV vector (for example AAV2 or AAV2/6). In some embodiments, the expression construct is administered systemically via a peripheral vein (e.g. intravenously).

In another aspect, pharmaceutical compositions comprising one or more of cells, expression constructs, transcription factors and/or nucleases described herein are provided.

In certain aspects, described herein are compositions, methods and systems for targeted integration of a liver-specific expression cassette. The methods and systems comprise administering one or more expression cassettes as described herein and administering one or more nucleases specific for a target gene (e.g., PCSK9, TTR, SERPINA1, KLKB1 and/or HAO1 and/or safe harbor gene) to a cell. Following nuclease-mediated cleavage of the target gene, the expression cassette is integrated into the gene via homology-dependent or homology-independent mechanisms. In certain embodiments, the target gene is an endogenous albumin gene.

For nuclease-mediated targeted integration of the expression constructs of the present invention, any nuclease can be used, including but not limited to, one or more zinc finger nucleases (ZFNs), TALENs, CRISPR/Cas nucleases and/or TtAgo nucleases, such that the expression construct is integrated into the region (gene) cleaved by the nuclease(s). In certain embodiments, one or more pairs of nucleases are employed. The nucleases may be introduced in mRNA form or may be administered to the cell using non-viral or viral vectors. In some aspects, the nuclease polynucleotides may be delivered by lentivirus or by non-integrating lentivirus. In other aspects, the expression cassette may be delivered by AAV and/or DNA oligos.

In a further aspect, methods and compositions are described herein for providing a therapeutic protein for treating a disorder where the therapeutic protein is a single chain antibody. In certain embodiments, the methods comprise administering an expression cassette (e.g., AAV vector) as described herein to the liver of a subject in need thereof. In other embodiments, the method comprises administering a modified cell (expressing a functional version of a protein that is aberrantly expressed in a subject from an expression cassette as described) to the subject.

In any of the compositions and methods described, expression cassettes and/or nucleases may be carried on an AAV vector, including but not limited to AAV1, AAV3, AAV4, AAV5, AAV6, AAV8, AAV9 and AAVrh10 or pseudotyped AAV such as AAV2/8, AAV8.2, AAV2/5 and AAV2/6 and the like. In certain embodiments, the polynucleotides (expression constructs and/or nucleases) are delivered using the same AAV vector types. In other embodiments, the polynucleotides are delivered using different AAV vector types. The polynucleotides may be delivered using one or more vectors. In certain embodiments, the polynucleotides are delivered via intravenous (e.g., intraportal vein or peripheral vein) administration into the liver of an intact animal.

The compositions and methods described herein can be used to treat or prevent disorders including e.g., TTR-Mediated Amyloidosis, A1AT Deficiency, Hereditary Angioedema, Familial Hypercholesterolemia/Static resistant hypercholesterolemia and Hyperxoaluria.

The methods described herein can be practiced in vitro, ex vivo or in vivo. In certain embodiments, the compositions are introduced into a live, intact mammal. The mammal may be at any stage of development at the time of delivery, e.g., embryonic, fetal, neonatal, infantile, juvenile or adult. Additionally, targeted cells may be healthy or diseased. In certain embodiments, one or more of the compositions are delivered intravenously (e.g., to the liver via the intraportal vein, for example tail vein injection or systemically via a peripheral vein), intra-arterially, intraperitoneally, intramuscularly, into liver parenchyma (e.g., via injection), into the hepatic artery (e.g., via injection), and/or through the biliary tree (e.g., via injection).

For targeting the compositions to a particular type of cell, e.g., platelets, fibroblasts, hepatocytes, etc., one or more of the administered compositions may be associated with a homing agent that binds specifically to a surface receptor of the cell. For example, the vector may be conjugated to a ligand (e.g., galactose) for which certain hepatic system cells have receptors. The conjugation may be covalent, e.g., a crosslinking agent such as glutaraldehyde, or noncovalent, e.g., the binding of an avidinated ligand to a biotinylated vector. Another form of covalent conjugation is provided by engineering the AAV helper plasmid used to prepare the vector stock so that one or more of the encoded coat proteins is a hybrid of a native AAV coat protein and a peptide or protein ligand, such that the ligand is exposed on the surface of the viral particle.

A kit, comprising the cells and/or expression constructs described herein, is also provided. The kit may further comprise nucleic acids encoding nucleases, (e.g. RNA molecules encoding ZFNs, TALENs or Cas and modified Cas proteins, and guide RNAs), transcription factors or aliquots of the nucleases, transcription factors, cells, instructions for performing the methods of the invention, and the like.

These and other aspects will be readily apparent to the skilled artisan in light of disclosure as a whole.

BRIEF DESCRIPTION OF THE DRAWINGS

FIGS. 1A and 1B depict partial sequence of the region in exon 5 of the human SERPINA1 gene near where the Z mutation is located. FIG. 1A (SEQ ID NO: 174 and 131) shows the site of the G→A mutation in the Z mutation gene sequence and also shows where the SERPINA1-specific ZFNs bind. Figure discloses peptide sequence as SEQ ID NO: 274. FIG. 1B (SEQ ID NO:132) shows the G→A mutation and also indicates the location of the sites of the altered nucleotides following integration of a gene correction donor.

FIG. 2A depicts the amount of ZFN-mediated NHEJ detected in the livers of the mice who were treated with either AAV8-ZFNs alone (25264 & 25277) at a low dose (7.5e10 vg per ZFN per mouse) or a high dose (1.5 e11 vg per ZFN per mouse) while FIG. 2B depicts the amount of targeted integration of the gene correction donor (1.5e12 vg per mouse AAV8 comprising the gene correction donor).

FIG. 3A depicts the amount of ZFN-mediated NHEJ detected in the livers of the mice who were treated with either AAV8-ZFNs alone (25264 & 25277) at a low dose (7.5e10 vg per ZFN per mouse AAV8) or a high dose (1.5 e11 vg per ZFN per mouse) and FIG. 3B depicts the amount of targeted integration of the gene correction donor (1.5e12 vg per mouse AAV8 comprising the gene correction donor).

FIG. 3C shows a direct comparison in the amount of detected NHEJ for the 2 week samples as compared to the 6 month samples.

FIGS. 4A through 4E (SEQ ID NO: 133-138) show partial sequences of TTR gene including potential areas to target with ZFNs. The heaviness of the box around the letter name of each target matches the heaviness of the target lines. FIGS. 4A through 4C depict the Exon 1 sequence while FIG. 4D shows sequence in Exon 2 and FIG. 4E shows sequence in Exon 3. For example, target 'A' is indicated with the light lines in FIG. 4A. Target 'B' is indicated by the heavier lines where the B pair will both bind to the sense (Watson) strand of the gene, while the 'C' target is bound by a ZFN pair that binds to the 5' sense target of B, and the C target on the antisense strand (also in a heavy line) in FIG. 4A. FIG. 4B shows the 'E' target which corresponds to the two heavy lines on the sense strand (shown under the sequence). The 'F' target uses the heavy E target line at the 5' end of the sense strand and the heavy target line on the antisense strand near F. The G target is depicted as the light lines on the sense strand of FIG. 4B. For FIG. 4C, the 'D' target is indicated by the light lines under the sense and antisense strands. FIG. 4D shows the 'H', 'I' and 'J' target sequences where all letter boxes are shown in the center of the two ZFN binding sequences. FIG. 4E depicts two ZFN targets, 'L' and 'M' where the L pair binds to the heavy lines and the M pair binds to the light lines.

FIG. 5A shows results with mRNA dose per ZFN in B16-F10 cells when the ZFN-encoding mRNAs are introduced via BTX electroporation, three days post transfection. FIG. 5B shows results in mouse hepatocytes three days post transfection when the ZFN-encoding mRNAs are introduced via lipofection.

FIG. 6A shows the cleavage activity (% indels) in livers from mice treated with the indicated ZFNs, either at a high (1.5e11 vg per ZFN per mouse) or low (2.5e10 vg per ZFN per mouse) doses, harvested 28 days post treatment. FIG. 6B shows the plasma mTTR concentration under the same treatment conditions. The data demonstrates that the ZFN cleave their targets in vivo, and cause a reduction in plasma TTR.

FIG. 8A shows the activity results at the on-target location of each of the test proteins, and FIG. 8B shows the activity at the sum of the 3 highest off target loci. The mutant proteins have increased on-target activity and decreased off target activity as compared to the parent proteins.

DETAILED DESCRIPTION

Figure 2B:
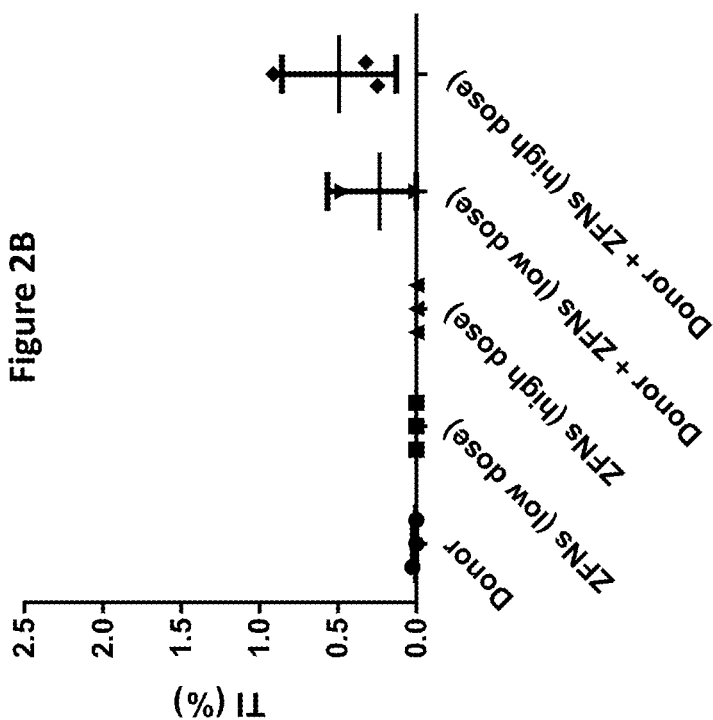
FIGS. 2A and 2B are graphs depicting the amount of NHEJ and TI in mice that have been treated with ZFN and the gene-correction donor where the animals were sacrificed at two weeks.

Disclosed herein are methods and compositions to modulate the expression of PCSK9, TTR, SERPINA1, KLKB1 or HAO1 genes as well as cassettes for production of PCSK9, TTR, SERPINA1, KLKB1 or HAO1 inhibitory transgenes, particularly in liver cells. Modulation of PCSK9, TTR, SERPINA1, KLKB1 or HAO1 expression may be achieved through the use of targeted nucleases (ZFN, TALEN, Ttago, CRISPR/Cas) to knock out the gene, and/or transcription factors (ZFP-TF, TALE-TF, RNA guided Cas-TF) to inhibit endogenous PCSK9, TTR, SERPINA1, KLKB1 or HAO1 expression. Cells comprising the gene modulators (polynucleotides and/or proteins) and/or comprising genetic modifications made by the gene modulators (but not comprising the gene modulators themselves) as well as cells descended from these cells are also provided. The methods and compositions of the invention can be used to express PCSK9, TTR, SERPINA1, KLKB1 and/or HAO1 inhibitory transgenes via liver-specific expression constructs. The compositions (constructs comprising gene modulators, proteins, and/or cells) as described herein may be delivered any transgene(s) to liver cells, in vivo or in vitro and can be used for the treatment and/or prevention of any disease or disorder which can be ameliorated by the provision of one or more of the transgenes via in vivo and/or ex vivo therapies.

Provided herein is a liver cell in which expression of an endogenous PCSK9, TTR, SERPINA1, KLKB1 and/or HAO1 gene is altered as compared to wild-type, for example by cleaving the gene using at least one artificial nuclease comprising a DNA-binding domain (that binds to a target site in the endogenous gene) and a cleavage domain or using an artificial transcription factor (repressor or activator) comprising a DNA-binding domain (that binds to a target site in the endogenous gene) and a transcriptionally regulatory domain (activator or repressor) such that is expression is altered. The target site can comprise at least 12 (e.g., 12, 13, 14, 15, 16, 17, 18, 19, 20, 21, 22 or more) contiguous or non-contiguous nucleotides as shown in the target sites of any of the appended Tables (e.g., Tables 1, 3, 5, 7, 11, 13, 14 and 16). An exogenous sequence (e.g., a transgene; a sequence that introduces a mutation into the gene, or a sequence that corrects a mutation in the endogenous gene) may be integrated into the endogenous gene following cleavage and/or one or more nucleotides may be inserted and/or deleted following cleavage. Also provided are fusion molecules comprising a DNA-binding domain (e.g., zinc finger protein, TAL-effector domain protein or single-guide RNA (sgRNA)) that binds to a target site in an endogenous PCSK9, TTR, SERPINA1, KLKB1 and/or HAO1 gene and a functional domain (e.g., cleavage domain, transcriptional activation domain or transcriptional repression domain) and polynucleotides (e.g., mRNA, viral or non-viral vectors, etc.) encoding these fusion molecules. Pharmaceutical compositions comprising cells, fusion molecules and/or polynucleotides as described herein are also provided as are methods of making and using the cells, fusion molecules and/or pharmaceutical compositions for the alteration of endogenous gene expression and/or the treatment of disorders such as TTR-Mediated Amyloidosis, A1AT Deficiency, Hereditary Angioedema, Familial Hypercholesterolemia/Static resistant hypercholesterolemia and Hyperoxaluria (via administration thereof to a subject in need).

Hereditary angioedema (HAE) is an autosomal dominant disease that affects 1 in 50,000 people and is a result of decreased levels of the C1 inhibitor. Patients experience recurrent episodes of swelling in any part of the body where swelling localized to the oropharynx, larynx or abdomen carry the highest risk of morbidity and death (see Tse and Zuraw, (2013) *Clev Clin J of Med* 80(5):297). The disease occurs from extravasation of plasma into tissues as a result of the over production of bradykinin. The mechanism seems to involve the cleavage of prekallikrein (also known as PKK, KLK3, PKKD, Fletcher factor and Kininogenin) by activate factor XII, releasing active plasma kallikrein (which activates more factor XII). Plasma kallikrein then cleaves kininogen, releasing bradykinin. The bradykinin then binds to the B2 bradykinin receptor on endothelial cells, increasing the permeability of the endothelium. Normally, the C1 inhibitor (encoded by SERPING1) controls bradykinin production by inhibiting plasma kallikrein and the activation of factor XII. HAE occurs in three types, Type I and II that are distinguished by the amount and type of C1 inhibitor present, and Type III which is tied to a Thr309Lys mutation in factor XII (Prieto et al (2009) *Allergy* 64(2):284). Type I HAE has low levels of C1 inhibitor that appear to be a result of poor expression and destruction of the small amount of C1 inhibitor protein that is made. Type 1 accounts for approximately 85% of HAE patients. Type II patients have normal levels of C1 inhibitor, but the C1 inhibitor protein is ineffectual due to mutations (Tse and Zuraw, ibid). More than 250 mutations in SERPING1 have been characterized that lead to Type I HAE including small and large insertions and deletions as well as duplications (Rijavec et al (2013) *PLoS One* 8(2): e56712). Due to this high variability in the genetic basis of HAE, the methods and compositions of the invention can be used to prevent or treat HAE by targeting downstream players in the manifestation of HAE. For example, targeting the gene encoding prekallikrein (KLKB1, expressed in hepatocytes) to effect a decrease in prekallikrein (abbreviated PKK) expression can result in a decrease in bradykinin production without regard to the type of mutation upstream that is causing the HAE, and thus result in a decrease in plasma extravasation. Thus, the methods and compositions of the invention may be used to cause a decrease in the expression of KLKB1 to prevent or treat HAE. Engineered nucleases can be used to knock out KLKB1 in a subset of hepatocytes that will reduce bradykinin production, and/or engineered transcription factors can be used to down regulate KLKB1 expression.

PCSK9 is a gene (also known as FH3; HCHOLA3; LDLCQ1; NARC-1; NARC 1; PC9) encoding a protein that plays a major regulatory role in cholesterol homeostasis. The PCSK9 protein binds to the epidermal growth factor-like repeat A (EGF-A) domain of LDLR, and induces LDLR degradation. Autosomal dominant, toxic gain of function mutations in PCSK9 (e.g. S 127R, P216L, D374Y and N157K) have been described and are associated with hyperlipidemia and Familial hypercholesterolemia (FH) as a result of an increased rate of LDLR degradation leading to a corresponding increase in plasma LDL cholesterol (Abifadel et al (2003) *Nat Gen* 34(2):154). In addition, loss of function PCSK9 mutations have been identified (e.g. Y142X, C679X and R46L) that cause an increase in hepatic LDLR levels, with an associated substantial decrease in the amount of plasma LDL cholesterol, leading to an 88% reduction in the incidence of coronary heart disease (Cohen et al (2003) *New Eng J Med* 354(12): 1264). Thus the methods and compositions of the invention can be used to treat or prevent hyperlipidemia and/or FH. Engineered nucleases can be designed to knock out a PCSK9 gene comprising a mutation that is associated with a toxic gain of function. Additionally, a wild type PCSK9 gene may be knocked out in a number of cells in the liver to treat FH caused by mutations in other genes such as LDLR or APOB. Alternatively, engineered transcription factors can be used to repress expression from a mutant or wild type PCSK9 gene.

Transthyretin Amyloidoses (TTRA) is one of several degenerative diseases suspected to be linked to misfolded and aggregated protein (amyloids). Transthyretin (TTR, also known as CTS; CTS1; HEL111; HsT2651; PALB; TBPA) is a tetramer produced in the liver and secreted into the bloodstream that serves to transport holo-retinal binding protein. However, upon conformational changes, it becomes amyloidogenic. Partial unfolding exposes stretches of hydrophobic residues in an extended conformation that efficiently misassemble into largely unstructured spherical aggregates that ultimately before cross-3 sheet amyloid structures (see Johnson et al (2012) *J Mol Biol* 421(2-3): 183). TTRA can occur in patients in both sporadic and autosomal dominant inherited forms which include familial amyloid polyneuropathy (FAP) and familial amyloid cardiomyopathy (FAC). These inherited forms are usually earlier onset and relate to over 100 point mutations described in the TTR gene. Generally, the more destabilizing of the protein that the mutation is, the more likely it is to have some amount of amyloid pathology. The amyloid formed causes selective destruction of cardiac tissue in FAC or peripheral and central nervous tissue in FAP. Some new therapeutic strategies for treating these diseases such as inhibitory RNA strategies center on trying to decrease the amount of TTR to decrease the aggregation potential of the protein (Johnson et al, ibid). Thus the methods and compositions of the invention can be used to target specific TTR mutants, and/or target wild type TTR in an effort to reduce the quantity of the pathological forms of the TTR protein and/or to decrease TTR concentration in general. Engineered nucleases may be used to knock out TTR in a subset of hepatocytes and/or engineered transcription factors specific for TTR may also be used to down regulate its expression.

Alpha-1-antitrypsin (A1AT) deficiency occurs in about 1 in 1500-3000 people of European ancestry but is rare in individuals of Asian descent. The alpha-1-antitrypsin protein is a protease inhibitor that is encoded by the SERPINA1 gene and serves to protect cells from the activity of proteases released by inflammatory cells, including neutrophil elastase, trypsin, metalloproteinase 9 (MMP-9), myeloperoxidase (MPO) and proteinase-3 (PR-3). Deficiency is an autosomal co-dominant or a recessive disorder caused by mutant SERPINA1 genes in heterozygous individuals where reduced expression from the mutant allele or the expression of a mutant A1AT protein with poor inhibitory activity leads to chronic lack of inhibition of neutrophil elastase resulting in tissue damage. The most common SERPINA1 mutation comprises a Glu342Lys substitution (also referred to as the Z allele) that causes the protein to form ordered polymers in the endoplasmic reticulum of patient hepatocytes. These inclusions ultimately cause liver cirrhosis which can only be treated by liver transplantation (Yusa et al (2011) *Nature* 478 p. 391). The polymerization within the hepatocytes results in a severe decrease in plasma A1AT levels, leading to increased risk of this inflammatory disease. In addition, A1AT deficiency is linked to pulmonary diseases including chronic obstructive pulmonary disease (COPD), emphysema and chronic bronchitis (Tuder et al (2010) *Proc Am Thorac Soc* 7(6): p. 381) and potentially may have a far broader reach into the inhibition of the progression of other diseases including type 1 and type 2 diabetes, acute myocardial infarction, rheumatoid arthritis, inflammatory bowel disease, cystic fibrosis, transplant rejection, graft versus host disease and multiple sclerosis (Lewis (2012) *Mol Med* 18(1) p. 957). In infancy and early childhood onset liver disease, the pathology of the disease presents as neonatal jaundice and cholestasis, which can be followed by progression to advanced fibrosis or cirrhosis. In adults, liver disease manifests as slowly progressive fibrosis which is typically diagnosed when the patient is in their fifth decade, where these patients have an increased risk of cirrhosis and hepatocellular carcinoma (Guo et al (2014) *J Clin Invest* 124(1):251). Population studies have suggested a minimum A1AT plasma threshold of approximately 0.5 mg/mL (normal plasma levels are approximately 0.9-1.75 mg/ML in a non-inflammatory state) to avoid these diseases, and current therapies mostly act to reduce symptoms through the use of bronchodilators and the like, although the use of weekly infusions of A1AT (Zemaira®, Prolastin) is also an option for emphysema patients with a demonstrated severe lack of plasma A1AT (Koepke et al (2015) *PLoS One* 10(1): e0117497). Severe lung disease associated with A1AT also is ultimately treated by transplant. Clinical trials for the treatment of A1AT deficiency involve a variety of approaches including the delivery of concentrated A1AT protein, use of an AAV construct comprising an A1AT gene by IM injection, and the use of A1AT in HIV, to list just a few. Thus, the compositions and methods of the invention can be used to treat or prevent diseases related to A1AT deficiency. Transcription factors and systems as described herein that are specific for the mutant A1AT allele (e.g. the Z allele) can be made to silence the gene and prevent expression, thereby eliminating the hepatic aggregates that can lead to cirrhosis. In addition, a wild type SERPINA1 gene may be introduced into the genome of the cell for expression, may be introduced via a non-integrating vector system (e.g. carrying a cDNA copy of the wild type gene) for extracellular expression, or may be introduced into the albumin locus in vivo for increased hepatic secretion while specific SERPINA1 nucleases are introduced to knock out an endogenous mutant SERPINA1 allele (e.g. the gene comprising the Z point mutation). In some embodiments, the Z point mutation is corrected by nuclease-driven insertion of a correcting oligonucleotide or partial cDNA such that the point mutation is corrected.

Primary hyperoxaluria type 1 (PH1), an inherited rare autosomal recessive disorder occurring in 0.11 to 0.26 per 100,000 births, is disease of glyoxylate metabolism, and arises from mutations in the enzyme alanine-glyoxylate aminotransferase (AGT, Siegal et al (2011) *Int J Organ Transpl Med* 2(3):126-132). The resulting deficiency in this enzyme leads to abnormally high oxalate production resulting in calcium oxalate crystal formation and deposition in the kidney and many other tissues, with systemic oxalosis and end-stage renal disease (ESRD) being a common outcome. Normally in the cell, glyoxylate present in cytoplasm is converted to glycolate by the enzyme glyoxylate reductase, and the glycolate can be taken up in the peroxisome and converted into glycine by AGT. When ACT is deficient, the accumulating glyoxylate is converted to oxalate by the liver-specific enzyme glycolate oxidase, or hydroxyacid oxidase-1 (HAO1, also known as HAO1X1, GOX1, GO and GOX). This increased accumulation of oxalate leads to supersaturation of urine with oxalate, and in turn leads to oxalate urolithiasis, nephrocalcinosis, renal tubular damage, renal failure and even death. ESRD in hyperoxaluria is accompanied by calcium oxalate deposition in the skin, bone marrow, bone (causing recurrent bone fractures), myocardium, nervous system, skeletal muscle, blood vessels and retina. Treatment is best initiated in children prior to kidney damage and can involve diet considerations (avoiding vitamin C and high oxalate foods) and daily dialysis. Unfortunately, dialysis is often able to significantly reduce the oxalate load. Liver transplant can be performed, but the therapeutics needed to avoid rejection can compound the kidney disorders associated with the PH1. In one study (Nolkemper et al (2000) *Pediatr Transplant* 4(3):177-81), there was an 82% survival when patients were given a liver transplant at 10 years of age, while when the transplant was performed at 20 years of age, survival dropped to 72%. In contrast, when a hepato-renal transplant was performed, there was an 80% patient survival rate when the transplant was performed 5 years of age, but this reduced to only 66% when performed at 20 years old (Eytan and Weismann (2009) *Pediatr Transplant* 13(7):805-807). RNAi approaches may offer some help as injection of GO-specific siRNAs decreased the expression of GO and reduced urinary oxalate excretion in a mouse disease model (Li et al (2016) *Biochim Biophys Acta* 1862(2):233-239).

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Recombination" refers to a process of exchange of genetic information between two polynucleotides, including but not limited to, capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms.

In certain methods of the disclosure, one or more targeted nucleases as described herein create a double-stranded break (DSB) in the target sequence (e.g., cellular chromatin) at a predetermined site (e.g., PCSK9 gene). The DSB mediates integration of a construct as described herein. Optionally, the construct has homology to the nucleotide sequence in the region of the break. The expression construct may be physically integrated or, alternatively, the expression cassette is used as a template for repair of the break via homologous recombination, resulting in the introduction of all or part of the nucleotide sequence as in the expression cassette into the cellular chromatin. Thus, a first sequence in cellular chromatin can be altered and, in certain embodiments, can be converted into a sequence present in an expression cassette. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, the exogenous nucleotide sequence (the "expression construct" or "expression cassette" or "vector") can contain sequences that are homologous, but not identical, to genomic sequences in the region of interest, thereby stimulating homologous recombination to insert a non-identical sequence in the region of interest. Thus, in certain embodiments, portions of the expression cassette sequence that are homologous to sequences in the region of interest exhibit between about 80 to 99% (or any integer therebetween) sequence identity to the genomic sequence that is replaced. In other embodiments, the homology between the expression cassette and genomic sequence is higher than 99%, for example if only 1 nucleotide differs as between the homology regions of the expression cassette and genomic sequences of over 100 contiguous base pairs. In certain cases, a non-homologous portion of the expression cassette can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest.

The term "sequence" refers to a nucleotide sequence of any length, which can be DNA or RNA; can be linear, circular or branched and can be either single-stranded or double stranded. The term "transgene" refers to a nucleotide sequence that is inserted into a genome. A transgene can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5' GAATTC 3' is a target site for the Eco RI restriction endonuclease.

An "episome" is a replicating nucleic acid, nucleoprotein complex or other structure comprising a nucleic acid that is not part of the chromosomal karyotype of a cell. Examples of episomes include plasmids, minicircles and certain viral genomes. The liver specific constructs described herein may be episomally maintained or, alternatively, may be stably integrated into the cell.

An "exogenous" molecule is a molecule that is not normally present in a cell, but can be introduced into a cell by one or more genetic, biochemical or other methods.

"Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, ligases, deubiquitinases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of fusion molecules include, but are not limited to, fusion proteins (for example, a fusion between a protein DNA-binding domain and a cleavage domain), fusions between a polynucleotide DNA-binding domain (e.g., sgRNA) operatively associated with a cleavage domain, and fusion nucleic acids (for example, a nucleic acid encoding the fusion protein).

Expression of a fusion molecule in a cell can result from delivery of the fusion molecule to the cell or by delivery of a polynucleotide encoding one or more components of the fusion molecule to a cell, wherein the polynucleotide is transcribed, and the transcript is translated, to generate the fusion molecule. In the case of CRISPR/Cas transcription factors and/or nucleases, the sgRNA DNA binding domain associates with the functional domain(s) (e.g., nuclease domain(s) or transcriptional regulatory domain) upon introduction of the sgRNA and functional domain encoding-sequences into the cell. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE or CRISPR/Cas system as described herein. Thus, gene inactivation may be partial or complete. Thus, a "gene modulator" is any molecule that modulates expression of a target gene, including but not limited to modification of the gene sequence and/or modification of gene expression.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples of safe harbor loci that are targeted by nuclease(s) include CCR5, HPRT, AAVS1, Rosa, ATPA1, CLYBL, and Albumin. See, e.g., U.S. Pat. Nos. 7,951,925; 8,771,985; 8,110,379; 7,951,925; U.S. Publication Nos. 20100218264; 20110265198; 20130137104; 20130122591; 20130177983; 20130177960; 20150056705 and 20150159172.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

"Eukaryotic" cells include, but are not limited to, fungal cells (such as yeast), plant cells, animal cells, mammalian cells and human cells (e.g., T-cells), including stem cells (pluripotent and multipotent).

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$. "Non-specific binding" refers to generalized, non-covalent interactions that occur between any molecule of interest (e.g. an engineered nuclease) and a macromolecule (e.g. DNA) that can occur at any generalized location in one molecule wherein such interaction is not limited to a target sequence.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity. In the case of an RNA-guided nuclease system, the RNA guide is heterologous to the nuclease component (Cas9 or Cfp1) and both may be engineered.

A "DNA binding molecule" is a molecule that can binding to DNA. Such DNA binding molecule can be a polypeptide, a domain of a protein, a domain within a larger protein or a polynucleotide. In some embodiments, the polynucleotide is DNA, while in other embodiments, the polynucleotide is RNA. In some embodiments, the DNA binding molecule is a protein domain of a nuclease (e.g. the FokI domain), while in other embodiments, the DNA binding molecule is a guide RNA component of an RNA-guided nuclease (e.g. Cas9 or Cfp1).

A "DNA binding protein" (or binding domain) is a protein, or a domain within a larger protein, that binds DNA in a sequence-specific manner through one or more zinc fingers or through interaction with one or more RVDs in a zinc finger protein or TALE, respectively. The term zinc finger DNA binding protein is often abbreviated as zinc finger protein or ZFP.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526 incorporated by reference herein in its entirety.

Zinc finger and TALE binding domains can be "engineered" to bind to a predetermined nucleotide sequence, for example via engineering (altering one or more amino acids) of the recognition helix region of a naturally occurring zinc finger protein or by engineering of the amino acids involved in DNA binding (the "repeat variable diresidue" or RVD region). Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 8,586,526; 6,140,081; 6,453,242; 6,746,838; 7,241,573; 6,866,997; 7,241,574 and 6,534,261; see also WO 98/53058; WO 98/53059; WO 98/53060; WO 02/016536 and WO 03/016496.

A "selected" zinc finger protein, TALE or CRISPR/Cas system is not found in nature whose production results primarily from an empirical process such as phage display, interaction trap, rational design or hybrid selection. See e.g., U.S. Pat. Nos. 8,586,526; 5,789,538; 5,925,523; 6,007,988; 6,013,453; 6,200,759; 6,242,568; 6,733,970; 7,297,491; WO 98/53057; WO 02/099084.

A "CRISPR/Cas" system refers to a nuclease or transcription factors system comprising a single guide RNA (sgRNA) DNA-binding domain and one or more cleavage domains (for nucleases) or transcriptional regulator domains (for transcription factors). The sgRNA can be designed to bind to any DNA sequence. The sgRNA, when associated with the cleavage or transcriptional regulatory domain(s) then mediates modulation of gene expression. See. e.g., U.S. Pat. Nos. 9,267,135 and 8,841,260 and U.S. Patent Publication Nos. 20150056705 and 20150031134.

"TtAgo" is a prokaryotic Argonaute protein thought to be involved in gene silencing. TtAgo is derived from the bacteria *Thermus thermophilus*. See, e.g., Swarts et al. (2014) *Nature* 507(7491):258-61; G. Sheng et al., (2013) *Proc. Natl. Acad. Sci. U.S.A.* 111, 652). A "TtAgo system" is all the components required including, for example, guide DNAs for cleavage by a TtAgo enzyme. "Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Recombination" refers to a process of exchange of genetic information between two polynucleotides, including but not limited to, capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In certain methods of the disclosure, one or more targeted nucleases as described herein create a double-stranded break (DSB) in the target sequence (e.g., cellular chromatin) at a predetermined site (e.g., a gene or locus of interest). The DSB mediates integration of a construct (e.g. donor) as described herein. Optionally, the construct has homology to the nucleotide sequence in the region of the break. An expression construct may be physically integrated or, alternatively, the expression cassette is used as a template for repair of the break via homologous recombination, resulting in the introduction of all or part of the nucleotide sequence as in the expression cassette into the cellular chromatin. Thus, a first sequence in cellular chromatin can be altered and, in certain embodiments, can be converted into a sequence present in an expression cassette. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional engineered nucleases can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence or via cleavage of the target sequence(s) followed by error-prone NHEJ-mediated repair that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miR-NAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known.

A polynucleotide "vector" or "construct" is capable of transferring gene sequences to target cells. Typically, "vector construct," "expression vector," "expression construct," "expression cassette," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the expression cassettes of the invention can be administered. Subjects of the present invention include those with a disorder.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Cancer, monogenic diseases and graft versus host disease are non-limiting examples of conditions that may be treated using the compositions and methods described herein.

Liver-Specific Expression Constructs

Described herein are expression cassettes (constructs) for use in directing expression of a transgene (e.g., one or more modulators of a PCSK9, a TTR, a SERPINA1, a KLKB1 and/or a HAO1 gene) in a liver cell, including in vivo following administration of the expression cassette(s) to the subject (e.g., peripheral or hepatic vein delivery). Also described here are expression cassettes (constructs) comprising a wildtype cDNA copy of a PCSK9, a TTR, a SERPINA1, a KLKB1 and/or a HAO1 gene for use in a cell where an endogenous mutant version of PCSK9, a TTR, a SERPINA1, a KLKB1 and/or a HAO1 gene has been knocked out by one or more modulators as described above. The expression construct may be maintained episomally and drive expression of the transgene extrachromosomally (see U.S. Publication No. 20170119906) or, alternatively, the expression construct may be integrated into the genome of a liver cell, for example by nuclease-mediated targeted integration.

The polynucleotide expression construct comprises an enhancer sequence, a promoter sequence, and one or more transgenes. Optionally included are one or more of the following: an intronic sequence, a polyadenylation sequence and/or a signal peptide. Any enhancer sequence may be used in the expression constructs described herein. In certain embodiments, the enhancer is a wild-type or modified Serpin1 enhancer (Chuah et al., (2014) *Molecular Therapy,* 22, 1605-1613; Nair et al. (2014) *Blood* 123, 3195-3199).

In preferred embodiments, the Serpin1 enhancer comprises one or more mutations (e.g., point mutations) as compared to wild-type, for example a Serpin1 enhancer containing one or more nucleotide modifications as shown, namely modifications of nucleotides at one or more of locations within the enhancer. See, e.g., U.S. Publication No. US-2017-0119906-A1.

Similarly, any promoter sequence can be used in the expression cassettes of the invention. In certain embodiments, the promoter is a constitutive promoter. In other embodiments, the promoter is an inducible or tissue specific promoter. In some embodiments, the promoter is a liver-specific promoter. In certain embodiments, the promoter is a transthyretin minimal promoter (TTRm) promoter. In other embodiments, the promoter is an alpha-1 anti-trypsin (hAAT) promoter.

Any of the polynucleotides described herein may further optionally comprise an intronic sequence. In certain embodiments, the expression construct includes a truncated chimeric intron (T-chimeric intron) sequence. The T-chimeric intron is a truncated version of the chimeric intron in pCI-neo (GenBank U47120). The chimeric intron in pCI-neo is the 5' splice donor site from the human β-globin gene, and the branchpoint and 3' acceptor site of an immunoglobulin gene heavy chain variable region. The T-chimeric intron contains a 45 bp deletion between the 5' splice donor and the branchpoint. In yet other embodiments, the expression constructs include a mutated MVM intron sequence (e.g., as shown in U.S. Publication No. US-2017-0119906-A1).

Alternatively, the expression constructs as described herein may lack an intronic sequence, for example as shown in U.S. Publication No. US-2017-0119906-A1.

The constructs described herein may be contained within any viral or non-viral vector. The constructs may be maintained episomally or may be integrated into the genome of the cell (e.g., via nuclease-mediated targeted integration).

Non-viral vectors include DNA or RNA plasmids, DNA MCs, naked nucleic acid, and nucleic acid complexed with a delivery vehicle such as a liposome, nanoparticle or poloxamer. Viral vectors that may be used to carry the expression cassettes described herein include, but are not limited to, retroviral, lentivirus, adenoviral, adeno-associated viral vectors, vaccinia and herpes simplex virus vectors. Integration in the host genome is possible with the retrovirus, lentivirus, and adeno-associated virus gene transfer methods, and as described herein may be facilitated by nuclease-mediated integration.

In certain preferred embodiments, the constructs are included in an adeno-associated virus ("AAV") vector or vector system that may be maintained episomally or integrated into the genome of a liver cell (e.g., via nuclease-mediated targeted integration). Construction of recombinant AAV vectors is in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

Thus, in certain embodiments, the expression construct is carried on an AAV construct and further comprises 5' and 3' ITRs flanking the expression constructs elements (e.g., enhancer, promoter, optional intron, transgene, etc.) as described herein. Optionally, spacer molecules are also included between one or more of the components of the expression construct, for example, between the 5' ITR and the enhancer and/or between the polyadenylation signal and the 3' ITR. The spacers may function as homology arms to facilitate recombination into a safe-harbor locus (e.g. albumin). In certain embodiments, the construct is a construct as shown in U.S. Publication No. US-2017-0119906-A1.

In certain embodiments, the AAV vectors as described herein can be derived from any AAV. In certain embodiments, the AAV vector is derived from the defective and nonpathogenic parvovirus adeno-associated type 2 virus. All such vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702-3 (1998), Kearns et al., *Gene Ther.* 9:748-55 (1996)). Other AAV serotypes, including AAV1, AAV2, AAV3, AAV4, AAV5, AAV6, AAV7, AAV8, AAV9 and AAVrh. 10 and any novel AAV serotype can also be used in accordance with the present invention. In some embodiments, chimeric AAV is used where the viral origins of the LTR sequences of the viral nucleic acid are heterologous to the viral origin of the capsid sequences. Non-limiting examples include chimeric virus with LTRs derived from AAV2 and capsids derived from AAV5, AAV6, AAV8 or AAV9 (i.e. AAV2/5, AAV2/6, AAV2/8 and AAV2/9, respectively).

Retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

The constructs described herein may also be incorporated into an adenoviral vector system. Adenoviral based vectors are capable of very high transduction efficiency in many cell types and do not require cell division. With such vectors, high titer and high levels of expression have been obtained. This vector can be produced in large quantities in a relatively simple system.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1): 10-20 (1997); Dranoff et al., *Hum. Gene Ther.* 1:111-2 (1997).

Replication-deficient recombinant adenoviral vectors (Ad) can also be used with the polynucleotides described herein. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package AAV and adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. In some embodiments, AAV is produced using a baculovirus expression system.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl.*

*Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

The polynucleotides described herein may include one or more non-natural bases and/or backbones. In particular, an expression cassette as described herein may include methylated cytosines to achieve a state of transcriptional quiescence in a region of interest.

Furthermore, the expression constructs as described herein may also include additional transcriptional or translational regulatory or other sequences, for example, additional promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Transgenes

The constructs described herein can be used for hepatic delivery of any transgene.

In certain embodiments, the transgene encodes a sequence comprising one or more modulators of a PCSK9, a TTR, a SERPINA1, a KLKB1 and/or a HAO1 gene, including but not limited to, one or more transcription factors that up-regulate or down-regulate expression of one or more these gene, one or more nucleases that cleave one or more of these genes, and/or one or more sequences that inhibit or activate one or more of these genes. Exemplary artificial transcription factors and/or nucleases that bind to target sites in one or more of these genes are described herein.

In other embodiments, the transgene encodes a cDNA sequence of a PCSK9, a TTR, a SERPINA1, a KLKB1 and/or a HAO1 gene. These transgenes may be used in cells in which the endogenous mutant copy of a PCSK9, a TTR, a SERPINA1, a KLKB1 and/or a HAO1 gene has been knocked out by a nuclease as described herein. The cDNA sequences may be integrated in the genome or may be maintained extrachromosomally (e.g. episomally).

The transgenes may also include promoter sequences, enhancer sequences, epitope tags, marker genes, cleavage enzyme recognition sites and various types of expression constructs. Marker genes that may be provided include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the transgene comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

In other embodiments, the transgene(s) encodes functional versions of proteins lacking of deficient in any genetic disease, including but not limited to, lysosomal storage disorders (e.g., Gaucher's, Fabry's, Hunter's, Hurler's, Neimann-Pick's, etc.), metabolic disorders, and/or blood disorders such as hemophilias and hemoglobinopathies, etc. See, e.g., U.S. Publication No. 20140017212 and 20140093913; U.S. Pat. Nos. 9,255,250 and 9,175,280.

For example, the transgene may comprise a sequence encoding a polypeptide that is lacking or non-functional in the subject having a genetic disease, including but not limited to any of the following genetic diseases: achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasiaossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesisimperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240), acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

Non-limiting examples of proteins (including functional fragments thereof such as truncated versions) that may be expressed as described herein include fibrinogen, prothrombin, tissue factor, Factor V, Factor VII, Factor IX, Factor X, Factor XI, Factor XII (Hageman factor), Factor XIII (fibrin-stabilizing factor), von Willebrand factor, prekallikrein, high molecular weight kininogen (Fitzgerald factor), fibronectin, antithrombin III, heparin cofactor II, protein C, protein S, protein Z, protein Z-related protease inhibitor, plasminogen, alpha 2-antiplasmin, tissue plasminogen activator, urokinase, plasminogen activator inhibitor-1, plasminogen activator inhibitor-2, glucocerebrosidase (GBA), α-galactosidase A (GLA), iduronate sulfatase (IDS), iduronidase (IDUA), acid sphingomyelinase (SMPD1), MMAA, MMAB, MMACHC, MMADHC (C2orf25), MTRR, LMBRD1, MTR, propionyl-CoA carboxylase (PCC) (PCCA and/or PCCB subunits), a glucose-6-phosphate transporter (G6PT) protein or glucose-6-phosphatase (G6Pase), an LDL receptor (LDLR), ApoB, LDLRAP-1, a PCSK9, a mitochondrial protein such as NAGS (N-acetylglutamate synthetase), CPS1 (carbamoyl phosphate synthetase I), and OTC (ornithine transcarbamylase), ASS (argininosuccinic acid synthetase), ASL (argininosuccinase acid lyase) and/or ARG1 (arginase), and/or a solute carrier family 25 (SLC25A13, an aspartate/glutamate carrier) protein, a UGT1A1 or UDP glucuronsyltransferase polypeptide A1, a fumarylacetoacetate hydrolyase (FAH), an alanine-glyoxylate aminotransferase (AGXT) protein, a glyoxylate reductase/hydroxypyruvate reductase (GRHPR) protein, a transthyretin gene (TTR) protein, an ATP7B protein, a phenylalanine hydroxylase (PAH) protein, a lipoprotein lyase (LPL) protein and/or a therapeutic single chain antibody.

In certain embodiments, the transgene can comprise a marker gene (described above), allowing selection of cells that have undergone targeted integration, and a linked sequence encoding an additional functionality. Non-limiting examples of marker genes include GFP, drug selection marker(s) and the like.

The constructs described herein may also be used for delivery of non-coding transgenes. Sequences encoding antisense RNAs, RNAi, shRNAs and micro RNAs (miR-NAs) may also be used for targeted insertions.

In certain embodiments, the transgene includes sequences (e.g., coding sequences, also referred to as transgenes) greater than 1 kb in length, for example between 2 and 200 kb, between 2 and 10 kb (or any value therebetween). The transgene may also include one or more nuclease target sites.

When integrated (e.g., via nuclease-mediate integration), the transgene may be inserted into an endogenous gene such that all, some or none of the endogenous gene is expressed.

Nucleases/Transcription Factors

In certain embodiments, the gene modulators described herein comprise one or more nucleases that inactivate a PCSK9, TTR, SERPINA1, KLKB1 and/or HAO1 gene. Furthermore, nucleases may also be used to integrated one or more transgenes into a target gene, for instance into a PCSK9, TTR, SERPINA1, KLKB1 or HAO1 gene and/or a safe harbor gene (e.g., albumin). Preferably, integration of the transgene construct(s) is targeted following cleavage of the target gene by one or more nucleases (e.g., zinc finger nucleases ("ZFNs"), TALENs, TtAgo, CRISPR/Cas nuclease systems, and homing endonucleases) and the construct integrated by either homology directed repair (HDR) or by end capture during non-homologous end joining (NHEJ) driven processes. See, e.g., U.S. Pat. Nos. 9,255,250; 9,200,266; 9,045,763; 9,005,973; 9,150,847; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983; 20130196373 and 20150056705, the disclosures of which are incorporated by reference in their entireties for all purposes.

Any nuclease can be used for targeted integration of a transgene (e.g., expression construct).

In certain embodiments, the nuclease comprises a zinc finger nuclease (ZFN), which comprises a zinc finger DNA-binding domain and a cleavage (nuclease) domain. See, e.g., U.S. Pat. Nos. 9,255,250; 9,200,266; 9,045,763; 9,005,973; 9,150,847; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861.

In other embodiments, the nuclease comprises a TALEN, which comprises a TAL-effector DNA binding domain and a cleavage (nuclease) domain. See, e.g., U.S. Pat. No. 8,586,526 and U.S. Publication No. 20130196373.

In still further embodiments, the nuclease comprises a CRISPR/Cas nuclease system, which includes a single guide RNA for recognition of the target site and one or more cleavage domains. See, e.g., U.S. Patent Publication No. 20150056705.

The cleavage domains of the nucleases may be wild-type or mutated, including non-naturally occurring (engineered) cleavage domains that form obligate heterodimers. See, e.g., U.S. Pat. Nos. 8,623,618; 7,888,121; 7,914,796; and 8,034,598 and U.S. Publication No. 20110201055.

The nuclease(s) may make one or more double-stranded and/or single-stranded cuts in the target site. The sites of cleavage and/or modification may be within the target site and/or between the two target sites when using a nuclease that functions as a dimer. In certain embodiments, the nuclease comprises a catalytically inactive cleavage domain (e.g., FokI and/or Cas protein). See, e.g., U.S. Pat. Nos. 9,200,266; 8,703,489 and Guillinger et al. (2014) *Nature Biotech.* 32(6):577-582. The catalytically inactive cleavage domain may, in combination with a catalytically active domain act as a nickase to make a single-stranded cut. Therefore, two nickases can be used in combination to make a double-stranded cut in a specific region. Additional nickases are also known in the art, for example, McCaffery et al. (2016) *Nucleic Acids Res.* 44(2):e11. doi: 10.1093/nar/gkv878. Epub 2015 Oct. 19.

In certain embodiments, the nuclease cleaves a safe harbor gene (e.g., CCR5, HPRT, AAVS1, ATPA1, CLYBL, Rosa, Albumin, etc). See, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983 and 20130177960. In preferred embodiments, the nuclease cleaves an endogenous albumin gene such that the expression cassette is integrated into the endogenous albumin locus of a liver cell. Albumin-specific nucleases are described, for example, in U.S. Pat. No. 9,150,847; and U.S. Publication Nos. 20130177983 and 20150056705.

In addition to, or instead of, nucleases as described herein, a PCSK9, TTR, SERPINA1, KLKB1 and/or HAO1 gene may be modulated (down-regulated) by the use of one or more engineered transcription factors. As with engineered nucleases, engineered transcription factors typically comprise at least one DNA-binding domain (e.g., that binds the targeted gene) and a functional domain (e.g., a transcriptional regulatory domain). Any engineered transcription factor that modulated PCSK9, TTR, SERPINA1, KLKB1 and/or HAO1 gene expression may be used.

A. DNA-Binding Domains

Any DNA-binding domain can be used in the nuclease and transcription factors described herein, including but not limited to a zinc finger DNA-binding domain, a TALE DNA binding domain, or a DNA-binding domain from a mega-nuclease, or a CRIPSR/Cas DNA binding complex (e.g., single guide RNA). In certain embodiments, the DNA-binding domain of the artificial transcription factor or artificial nuclease binds to a target site of 9, 10, 11, 12, 13, 14, 15, 16, 17, 18, 19, 20, 21, 22, 23, 24 or more nucleotides as shown in any of the target sites disclosed herein.

In certain embodiments, the DNA-binding domain comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et al (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas et al (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 base pairs in the repeat domain of hpx17. However, both gene products have less than 40% sequence identity with AvrBs3 family proteins of *Xanthomonas*.

Thus, in some embodiments, the DNA binding domain that binds to a target site in a target locus is an engineered domain from a TAL effector similar to those derived from the plant pathogens *Xanthomonas* (see Boch et al, (2009) *Science* 326: 1509-1512 and Moscou and Bogdanove, (2009) *Science* 326: 1501) and *Ralstonia* (see Heuer et al (2007) *Applied and Environmental Microbiology* 73(13): 4379-4384); U.S. Pat. Nos. 8,586,526; 8,420,782 and 8,440,431.

In certain embodiments, the DNA binding domain comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 7,888,121; 7,972,854; 6,453,242; 6,534,261; 6,599,692; 6,503,717; 6,689,558; 7,030,215; 6,794,136; 7,067,317; 7,262,054; 7,070,934; 7,361,635; 7,253,273, all incorporated herein by reference in their entireties.

An engineered zinc finger binding or TALE domain can have a novel binding specificity, compared to a naturally-occurring zinc finger or TALE protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 8,586,526; 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in WO 02/077227.

In addition, as disclosed in these and other references, DNA domains (e.g., multi-fingered zinc finger proteins or TALE domains) may be linked together using any suitable linker sequences, including for example, linkers of 5 or more amino acids in length. See, also, U.S. Pat. Nos. 6,479,626; 6,903,185; 7,153,949; 9,567,609; and U.S. Patent Publication Nos. 20170218349 and 20170211075 for non-limiting examples of linker sequences. The DNA binding proteins described herein may include any combination of suitable linkers between the individual zinc fingers of the protein. In addition, enhancement of binding specificity for zinc finger binding domains has been described, for example, in WO 02/077227.

Selection of target sites; DNA-binding domains and methods for design and construction of fusion molecules (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496 and U.S. Publication No. 20110301073.

In still further embodiments, the DNA binding domain comprises a DNA-binding single-guide RNA in combination with a functional domain (e.g., CRISPR/Cas transcription factor). See, e.g., U.S. Pat. No. 8,697,359.

B. Functional Domains

The DNA-binding domains may be operably linked to any functional domain useful in gene modulation (e.g., repression) as described herein. Thus, artificial nucleases and transcription factors comprising DNA-binding domains (e.g., ZFPs or TALEs, CRISPR/Cas components such as single guide RNAs) as described herein associated with a heterologous regulatory (functional) domain (or functional fragment thereof) are also provided. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. Thus, the invention provides artificial transcription factors comprising the DNA-binding domains described herein and a transcriptional regulatory domain as well as artificial nucleases comprising the DNA-binding domains and one or more nuclease domains.

In certain embodiments, the functional domain comprises a transcriptional regulatory domain, for example a repression domain. Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

It will be clear to those of skill in the art that, in the formation of a fusion molecule (or a nucleic acid encoding same) between a DNA-binding domain as described herein and a functional domain, either a repression domain or a molecule that interacts with a repression domain is suitable as a functional domain. Essentially any molecule capable of recruiting a repressor (e.g., protein or complex) and/or repressing activity (such as, for example, histone demethylation) to the target gene is useful as a repression domain, and consequently can be used in the practice of the claimed invention. Insulator domains, localization domains, and chromatin remodeling proteins such as ISWI-containing domains and/or methyl binding domain proteins suitable for use as functional domains in fusion molecules are described, for example, in U.S. Pat. Nos. 6,919,204 and 7,053,264.

Non-limiting examples of transcriptional activation domains. Suitable domains for achieving activation (transcriptional activation domains) include the HSV VP16 activation domain; nuclear hormone receptors; the p65 subunit of nuclear factor kappa Bl or artificial chimeric functional domains such as VP64 and degron. Additional exemplary activation domains include, Oct 1, Oct-2A, Sp1, AP-2, and CTF1 as well as p300, CBP, PCAF, SRC1 PvALF, AtHD2A, ERF-2, OsGAI, HALF-1, C1, AP1, ARF-5, -6, -7, and -8, CPRF1, CPRF4, MYC-RP/GP, and TRAB1.

In certain embodiments, the target site bound by the DNA-binding domain is present in an accessible region of cellular chromatin. Accessible regions can be determined as described, for example, in U.S. Pat. No. 6,511,808. If the target site is not present in an accessible region of cellular chromatin, one or more accessible regions can be generated as described in WO 01/83793. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al. (1987) *Cell* 48:261-270; Pina et al. (1990) *Cell* 60:719-731; and Cirillo et al. (1998) *EMBO J.* 17:244-254.

In certain embodiments, at least one component of the proteins and systems described herein is naturally occurring (e.g., a naturally occurring functional domain). In other embodiments, the compositions described herein are comprised of all non-naturally occurring components, i.e., engineered in the DNA-binding domain and the functional domain. For example, the DNA-binding domain of a naturally-occurring domain may be altered to bind to a selected target site.

In certain embodiments, the PCSK9, TTR, SERPINA1, KLKB1 or HAO1 gene modulator comprises a CRISPR/Cas transcription factor system. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR, initially described in *S. pyogenes*, is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences where processing occurs by a double strand-specific RNase III in the presence of the Cas9 protein. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. In addition, the tracrRNA must also be present as it base pairs with the crRNA at its 3' end, and this association triggers Cas9 activity. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

Type II CRISPR systems have been found in many different bacteria. BLAST searches on publically available genomes by Fonfara et al ((2013) *Nuc Acid Res* 42(4):2377-2590) found Cas9 orthologs in 347 species of bacteria. Additionally, this group demonstrated in vitro CRISPR/Cas cleavage of a DNA target using Cas9 orthologs from *S. pyogenes, S. mutans, S. therophilus, C. jejuni, N. meningitides, P. multocida* and *F. novicida*. Thus, the term "Cas9" refers to an RNA guided DNA nuclease comprising a DNA binding domain and two nuclease domains, where the gene encoding the Cas9 may be derived from any suitable bacteria.

The wild-type Cas9 protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand. The Cas 9 nuclease can be engineered such that only one of the nuclease domains is functional, creating a Cas nickase (see Jinek et al, ibid). Nickases can be generated by specific mutation of amino acids in the catalytic domain of the enzyme, or by truncation of part or all of the domain such that it is no longer functional. Since Cas 9 comprises two nuclease domains, this approach may be taken on either domain. A double strand break can be achieved in the target DNA by the use of two such Cas 9 nickases. The nickases will each cleave one strand of the DNA and the use of two will create a double strand break.

The requirement of the crRNA-tracrRNA complex can be avoided by use of an engineered "single-guide RNA"

(sgRNA) that comprises the hairpin normally formed by the annealing of the crRNA and the tracrRNA (see Jinek et al (2012) *Science* 337:816 and Cong et al (2013) Sciencexpress/10.1126/science.1231143). In *S. pyrogenes*, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing (see Ramalingam ibid) and has been useful for zebrafish embryo genomic editing in vivo (see Hwang et al (2013) *Nature Biotechnology* 31 (3):227) with editing efficiencies similar to ZFNs and TALENs. In addition, CRISPR/Cas transcription factors have also been described. See, e.g., U.S. Pat. No. 8,697,359; Piatek et al. (2015) *Plant Biotechnology J.* 13(4):578-589 and Perez-Pinera et al. (2013) *Nature Methods* 10:973-976).

Chimeric or sgRNAs can be engineered to comprise a sequence complementary to any desired target for transcriptional regulation as described herein. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In certain embodiments, the RNAs comprise 22 bases of complementarity to a target and of the form G[n19], followed by a protospacer-adjacent motif (PAM) of the form NGG. Thus, in one method, sgRNAs can be designed by utilization of a known target of a DNA-binding domain (e.g., ZFP, TALE) in a gene of interest. In addition, sgRNAs can be designed to known paired nuclease sites by (i) aligning the target sequences of the ZFN heterodimer with the reference sequence of the relevant genome (human, mouse, or of a particular plant species); (ii) identifying the spacer region between the ZFN half-sites; (iii) identifying the location of the motif G[N20]GG that is closest to the spacer region (when more than one such motif overlaps the spacer, the motif that is centered relative to the spacer is chosen); (iv) using that motif as the core of the sgRNA. This method advantageously relies on proven nuclease targets. Alternatively, sgRNAs can be designed to target any region of interest simply by identifying a suitable target sequence the conforms to the G[n20]GG formula. Along with the complementarity region, an sgRNA may comprise additional nucleotides to extend to tail region of the tracrRNA portion of the sgRNA (see Hsu et al (2013) *Nature Biotech* doi: 10.1038/nbt.2647). Tails may be of +67 to +85 nucleotides, or any number therebetween with a preferred length of +85 nucleotides. Truncated sgRNAs may also be used, "tru-gRNAs" (see Fu et al, (2014) *Nature Biotech* 32(3): 279). In tru-gRNAs, the complementarity region is diminished to 17 or 18 nucleotides in length.

Further, alternative PAM sequences may also be utilized, where a PAM sequence can be NAG as an alternative to NGG (Hsu 2014, ibid) using a *S. pyogenes* Cas9. Additional PAM sequences may also include those lacking the initial G (Sander and Joung (2014) *Nature Biotech* 32(4):347). In addition to the *S. pyogenes* encoded Cas9 PAM sequences, other PAM sequences can be used that are specific for Cas9 proteins from other bacterial sources. For example, the PAM sequences shown below (adapted from Sander and Joung, ibid, and Esvelt et al, (2013) *Nat Meth* 10(11): 1116) are specific for these Cas9 proteins:

| Species | PAM |
| --- | --- |
| S. pyogenes | NGG |
| S. pyogenes | NAG |
| S. mutans | NGG |
| S. thermophilius | NGGNG |
| S. thermophilius | NNAAAW |
| S. thermophilius | NNAGAA |
| S. thermophilius | NNNGATT |
| C. jejuni | NNNNACA |
| N. meningitides | NNNNGATT |
| P. multocida | GNNNCNNA |
| F. novicida | NG |

Thus, a suitable target sequence for use with a *S. pyogenes* CRISPR/Cas system can be chosen according to the following guideline: [n17, n18, n19, or n20](G/A)G. Alternatively the PAM sequence can follow the guideline G[n17, n18, n19, n20](G/A)G. For Cas9 proteins derived from non-*S. pyogenes* bacteria, the same guidelines may be used where the alternate PAMs are substituted in for the *S. pyogenes* PAM sequences.

Most preferred is to choose a target sequence with the highest likelihood of specificity that avoids potential off target sequences. These undesired off target sequences can be identified by considering the following attributes: i) similarity in the target sequence that is followed by a PAM sequence known to function with the Cas9 protein being utilized; ii) a similar target sequence with fewer than three mismatches from the desired target sequence; iii) a similar target sequence as in ii), where the mismatches are all located in the PAM distal region rather than the PAM proximal region (there is some evidence that nucleotides 1-5 immediately adjacent or proximal to the PAM, sometimes referred to as the 'seed' region (Wu et al (2014) *Nature Biotech* 32(7):670-676) are the most critical for recognition, so putative off target sites with mismatches located in the seed region may be the least likely be recognized by the sg RNA); and iv) a similar target sequence where the mismatches are not consecutively spaced or are spaced greater than four nucleotides apart (Hsu 2014, ibid). Thus, by performing an analysis of the number of potential off target sites in a genome for whichever CRIPSR/Cas system is being employed, using these criteria above, a suitable target sequence for the sgRNA may be identified.

In some embodiments, the CRISPR-Cpf1 system is used. The CRISPR-Cpf1 system, identified in *Francisella* spp, is a class 2 CRISPR-Cas system that mediates robust DNA interference in human cells. Although functionally conserved, Cpf1 and Cas9 differ in many aspects including in their guide RNAs and substrate specificity (see Fagerlund et al, (2015) *Genom Bio* 16:251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term "Cas" includes both Cas9 and Cpf1 proteins. Thus, as used herein, a "CRISPR/Cas system" refers both CRISPR/Cas and/or CRISPR/Cpf1 systems, including both nuclease and/or transcription factor systems.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. In some aspects, a functional derivative may comprise a single biological property of a naturally occurring Cas protein. In other aspects, a function derivative may comprise a subset of biological properties of a naturally occurring Cas protein. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Exemplary CRISPR/Cas single guide RNAs targeted to specific genes are disclosed for example, in U.S. Publication No. 20150056705.

Thus, the compositions and systems described herein comprises one or more DNA-binding domains that specifically bind to one or more target sites in selected gene and at least one functional domain such that, when introduced into a cell, the composition (or system) modulates PCSK9, TTR, SERPINA1, KLKB1 or HAO1 gene expression.

Target Sites

As described in detail above, DNA-binding domains of the artificial nucleases and/or transcription factors as described herein can be engineered to bind to any sequence of choice. An engineered DNA-binding domain can have a novel binding specificity, compared to a naturally-occurring DNA-binding domain. In certain embodiments, the DNA-binding domains bind to a sequence within a liver-specific gene as described herein, for example a target site (typically 9, 10, 11, 12, 13, 14, 15, 16, 17, 18, 19, 20, 21 or even more base pairs), including DNA-binding domains that bind to a sequence or 12 or more base pairs (contiguous or non-contiguous) of the target sites shown herein (e.g., Tables 1, 3, 5, 7, 11, 13, 14, and 16). Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties. Rational design of TAL-effector domains and single guide RNAs is also known. See, e.g., U.S. Pat. No. 8,771,985 and U.S. Patent Publication No. 20150056705.

Delivery

The nucleases, transcription factors and/or transgenes (e.g., PCSK9, TTR, SERPINA1, KLKB1 or HAO1 inhibitors) may be delivered in vivo or ex vivo by any suitable means into any cell type, preferably to the liver (systemically or via hepatic delivery). Similarly, when used in combination with nucleases for targeted integration, the nucleases may be delivered in polynucleotide and/or protein form, for example using non-viral vector(s), viral vectors(s) and/or in RNA form, e.g., as mRNA.

Methods of non-viral delivery of nucleic acids include electroporation, lipofection, microinjection, biolistics, virosomes, liposomes, immunoliposomes, other nanoparticle, polycation or lipid:nucleic acid conjugates, naked DNA, artificial virions, and agent-enhanced uptake of DNA. Sonoporation using, e.g., the Sonitron 2000 system (RichMar) can also be used for delivery of nucleic acids. Additional exemplary nucleic acid delivery systems include those provided by AmaxaBiosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336).

In preferred embodiments, the expression constructs are AAV vectors. The optional nucleases may be administered in mRNA form or using one or more viral vectors (AAV, Ad, etc.). Administration can be by any means in which the polynucleotides are delivered to the desired target cells. Both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree. Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al., (1994) *Nature Genetics,* 6:335-341.

In systems involving delivery of more than one polynucleotides (e.g., construct as described herein and nuclease in polynucleotide form), the two or more polynucleotide(s) are delivered using one or more of the same and/or different vectors. For example, the nuclease in polynucleotide form may be delivered in mRNA form and the liver-specific constructs as described herein may be delivered via other modalities such as viral vectors (e.g., AAV), minicircle DNA, plasmid DNA, linear DNA, liposomes, nanoparticles and the like.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

The effective amount of expression cassette (and optional nuclease(s), and/or modified cells) to be administered will vary from patient to patient. Accordingly, effective amounts are best determined by the physician administering the compositions (e.g., cells) and appropriate dosages can be determined readily by one of ordinary skill in the art. Analysis of the serum or other tissue levels of the therapeutic polypeptide and comparison to the initial level prior to administration can determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.*, 6:1391-1401.

Formulations for both ex vivo and in vivo administrations include suspensions (e.g., of genetically modified cells, liposomes or nanoparticles) in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods and compositions disclosed herein are useful in providing therapies for any PCSK9, TTR, SERPINA1, KLKB1 and/or HAO1-related disorder by modulating the expression of the endogenous PCSK9, TTR, SERPINA1, KLKB1 or HAO1 gene, including via the provision of a PCSK9, TTR, SERPINA1, KLKB1 and/or HAO1-inhibitory transgene (transcription factor, nuclease, etc.). In addition, the methods and compositions provide methods for knock out of a mutant PCSK9, TTR, SERPINA1, KLKB1 or HAO1 gene and the provision of a wild type PCSK9, TTR, SERPINA1, KLKB1 or HAO1 cDNA for treatment or prevention of such a disorder. The cell may be modified in vivo or may be modified ex vivo and subsequently administered to a subject. Thus, the methods and compositions provide for the treatment and/or prevention of such PCSK9, TTR, SERPINA1, KLKB1 and/or HAO1 related disorders. Thus, the compositions and methods described herein can be used to treat or prevent disorders including e.g., TTR-Mediated Amyloidosis, A1AT Deficiency, Hereditary Angioedema, Familial Hypercholesterolemia/Static resistant hypercholesterolemia and Hyperxoaluria.

The following Examples include exemplary embodiments of the present disclosure in which the optionally used nuclease comprises a zinc finger nuclease (ZFN) or CRISPR/Cas system. It will be appreciated that this is for purposes of exemplification only and that other nucleases can be used, for example TALENs, homing endonucleases (meganucleases) with engineered DNA-binding domains that bind to target sites as described herein and/or fusions of naturally occurring of engineered homing endonucleases (meganucleases) DNA-binding domains and heterologous cleavage domains and/or fusions of meganucleases and TALE proteins. In addition, it will be appreciated that expression constructs as described herein can be carried on other vectors (other than AAV) to produce the same results in the treatment and/or prevention of disorders caused by deficient protein production.

EXAMPLES

Example 1: Design, Construction and General Characterization of Compositions that Modulate the PCSK9, TTR, SERPINA1, KLKB1 or HAO1 Genes Zinc finger, Cas and TALE proteins that bind to either the mouse or human PCSK9, TTR, SERPINA1, KLKB1 or HAO1 gene operably linked to transcriptional regulatory or nuclease domains are designed and incorporated into plasmids, AAV or adenoviral vectors or made into mRNA essentially as described in Urnov et al. (2005) *Nature* 435(7042):646-651, Perez et al (2008) *Nature Biotechnology* 26(7):808-816, and as described in U.S. Pat. Nos. 8,586,526 and 6,534,261.

sgRNAs for use in the CRISPR/Cas system are made synthetically by methods known in the art (see Hsu et al, (2013) *Nature Biotech* doi:10.1038/nbt.2647, or Sternberg et al, (2014) *Nature* 507: 62). The sgRNAs are engineered as described above and are designed to target a sequence in the endogenous PCSK9, TTR, SERPINA1, KLKB1 and/or HAO1 gene (e.g., a target sequences as set forth in herein).

The human or mouse PCSK9, TTR, SERPINA1, KLKB1 and/or HAO1-specific nucleases are introduced into human (e.g. K562) or mouse cells as mRNA and are analyzed for cleavage activity. Briefly, the cells are transfected with two doses of mRNA (2 or 6 μg in total of the two ZFNs) using a BTX 96 well electroporator (BTX) according to standard protocols. Cells are then expanded for an additional 7 days. Cells are removed at day 7 and analyzed for on target PCSK9, TTR, SERPINA1, KLKB1 or HAO1 modification using deep sequencing (Miseq, Illumina).

For PCSK9, TTR, SERPINA1, KLKB1 and/or HAO1-specific CRISPR/Cas experiments, Cas9 is supplied on a pVAX plasmid, and the sgRNA are supplied on a plasmid under the control of the U6 promoter. The plasmids are mixed at either 100 ng of each or 400 ng of each and are mixed with 2e5 cells per run. The cells are transfected using the Amaxa system. Briefly, an Amaxa transfection kit is used and the nucleic acids are transfected using a standard Amaxa shuttle protocol. Following transfection, the cells are left to rest for 10 minutes at room temperature and then resuspended in prewarmed RPMI. The cells are then grown in standard conditions at 37° C. Genomic DNA is isolated 7 days after transfection and subject to MiSeq analysis.

All nucleases are found bind to their target sites and to be functionally active (in cleaving the target gene).

Example 2: Design, Construction and General Characterization of Compositions that Modulate PCSK9, TTR, SERPINA1, KLKB1 or HAO1 Gene Expression Zinc finger proteins are targeted to PCSK9, TTR, SERPINA1, KLKB1 or HAO1 were engineered essentially as described in Zhang et al (2000) *J Biol Chem* 275(43):33850-33860). The ZFPs were evaluated and shown to be bind and cleave their target sites. Linkers and ZFN architecture are as previously described (U.S. Publication Nos. 20170218349 and 20170211075). For example, linker L0 is LRGSQLVKS (SEQ ID NO:139), linker N7a is SGTPHEVGVYTL (SEQ ID NO:140), linker N6a is SGAQGSTLDF (SEQ ID NO: 141), and linker L8c4 is LRGSYAPMPPLALASP (SEQ ID NO: 142).

I. Nuclease Targeting of PCSK9

PCSK9-specific zinc finger proteins were made as described above. Exemplary proteins (including the linker) are shown below in Table 1.

TABLE 1

Human PCSK9-specific zinc finger proteins

| SBS #/Target | F1 | F2 | F3 | F4 | F5 | F6 | linker |
|---|---|---|---|---|---|---|---|
| SBS#60045 5' taCGTGGTGGTGCT GAAGGAggagaccc (SEQ ID NO: 1) | QSSHLTR (SEQ ID NO: 13) | QSGNLAR (SEQ ID NO: 14) | QSSDLSR (SEQ ID NO: 15) | WHSSLHQ (SEQ ID NO: 16) | LRHHLTR (SEQ ID NO: 17) | HKQHRDA (SEQ ID NO: 18) | L0 |
| SBS#60043 5' agGATCCGtGGAGG TTGCCTGgcaccta (SEQ ID NO: 2) | RSDVLSE (SEQ ID NO: 19) | TRNGLKY (SEQ ID NO: 20) | TSGHLSR (SEQ ID NO: 21) | QSGHLSR (SEQ ID NO: 22) | NNRDLIN (SEQ ID NO: 23) | TSSNLSR (SEQ ID NO: 24) | N7a* |
| SBS#60134 5' ttACCGGGGGGCTG GTAttcatccgccc (SEQ ID NO: 3) | QSGALAR (SEQ ID NO: 25) | RSDVLSE (SEQ ID NO: 19) | RSAHLSR (SEQ ID NO: 26) | RSDHLSR (SEQ ID NO: 27) | DRSVLAR (SEQ ID NO: 28) | N/A | N7a* |
| SBS#60133 5' ccGCCCGGTACCGT GGAGGGgtaatccg (SEQ ID NO: 4) | RSDHLSR (SEQ ID NO: 27) | QSGHLSR (SEQ ID NO: 22) | HKQHRDA (SEQ ID NO: 18) | DNSNRIK (SEQ ID NO: 29) | RSDHLSE (SEQ ID NO: 30) | HSRTRTK (SEQ ID NO: 31) | L0 |
| SBS#60137 5' agATGGGGTCTTA CCGGGGggctggta (SEQ ID NO: 5) | RSDHLSR (SEQ ID NO: 27) | QQWDRKQ (SEQ ID NO: 32) | TPSYLPT (SEQ ID NO: 33) | DRSALAR (SEQ ID NO: 34) | RSDHLSE (SEQ ID NO: 30) | RKDARIT (SEQ ID NO: 35) | N6a* |
| SBS#60334 5' ggTACCGGGCGGAT GAAtaccagccccc (SEQ ID NO: 6) | QSGNLAR (SEQ ID NO: 14) | TSGNLTR (SEQ ID NO: 36) | RSDDLTR (SEQ ID NO: 37) | RSDHLSE (SEQ ID NO: 30) | DKSNRKK (SEQ ID NO: 38) | N/A | N7a* |
| SBS#60259 5' gaGGCTGGGGAGTA GAGGCAggcatcgt (SEQ ID NO: 7) | QSGDLTR (SEQ ID NO: 39) | RSDNLTR (SEQ ID NO: 40) | QSGALAR (SEQ ID NO: 25) | QSGHLSR (SEQ ID NO: 22) | RSDHLSQ (SEQ ID NO: 41) | DSSHRTR (SEQ ID NO: 42) | N7a* |
| SBS#60254 5' cgCTGCCGGCAACT TCCGGGacgatgcc (SEQ ID NO: 8) | RSAHLSR (SEQ ID NO: 26) | DSSDRKK (SEQ ID NO: 43) | QHQVLVR (SEQ ID NO: 44) | QNATRTK (SEQ ID NO: 45) | RSDTLSE (SEQ ID NO: 46) | RSPGRMG (SEQ ID NO: 47) | N6a* |
| SBS#60256 5' cgCTGCCGGCAACT TCCGGGacgatgcc (SEQ ID NO: 8) | RSAHLSR (SEQ ID NO: 26) | DSSDRKK (SEQ ID NO: 43) | QHQVLVR (SEQ ID NO: 44) | QNATRTK (SEQ ID NO: 45) | RSDTLSE (SEQ ID NO: 46) | RSPGRMG (SEQ ID NO: 47) | N7a* |
| SBS#60289 5' agAGAAGTGGATCA GTCTCTgcctcaac (SEQ ID NO: 9) | DGYYLPT (SEQ ID NO: 48) | DRSALAR (SEQ ID NO: 34) | ERQTLIK (SEQ ID NO: 49) | QSGHLSR (SEQ ID NO: 22) | HRWHLQT (SEQ ID NO: 50) | AQCCLFH (SEQ ID NO: 51) | N6a* |
| SBS#60287 5' cgGAGCTCACCCTG GCCGAGttgaggca (SEQ ID NO: 10) | RSDNLAR (SEQ ID NO: 52) | DRSVLHR (SEQ ID NO: 53) | RSDTLSA (SEQ ID NO: 54) | DKSTRTK (SEQ ID NO: 55) | PCRYRLD (SEQ ID NO: 56) | RSANLTR (SEQ ID NO: 57) | N6a* |
| SBS#60309 5' taTCCCCGGCGGGC AGCCTGggcctgca (SEQ ID NO: 11) | RSDVLSE (SEQ ID NO: 19) | QKCCLRS (SEQ ID NO: 58) | DRSHLTR (SEQ ID NO: 59) | RSDDLTR (SEQ ID NO: 37) | RSDTLSN (SEQ ID NO: 60) | TNSDRTK (SEQ ID NO: 61) | N6a* |

TABLE 1-continued

Human PCSK9-specific zinc finger proteins

| SBS #/Target | Design | | | | | | linker |
|---|---|---|---|---|---|---|---|
| | F1 | F2 | F3 | F4 | F5 | F6 | |
| SBS#60308<br>5'<br>tgCAGGCGGCGGGC<br>aGTGCGCtctgact<br>(SEQ ID NO: 12) | HRQRLEE<br>(SEQ ID<br>NO: 62) | RNASRTR<br>(SEQ ID<br>NO: 63) | DRSHLTR<br>(SEQ ID<br>NO: 59) | RSDDLTR<br>(SEQ ID<br>NO: 37) | RSDTLSE<br>(SEQ ID<br>NO: 46) | KPYNLQQ<br>(SEQ ID<br>NO: 64) | L0 |

*indicates that the DNA binding domain is attached to the FokI nuclease domain at the DNA binding domain's N-terminus (see U.S. Publication Nos. 20170218349 and 20170211075)

The nucleases were tested for activity in K562 cells where 2 μg of each mRNA encoding a partner nuclease was added in a 100 μL transfection volume. All proteins bound to their targets and induced cleavage. Exemplary results of pairwise combinations are shown below in Table 2, where "% indel" indicates the activity. % indels were measured by deep sequencing (MiSeq, Illumnia) and then analyzed for the percent of alleles comprising insertions and/or deletions at the cleavage site. Table 2 demonstrates that these exemplary ZFN pairs were all active.

TABLE 2

PCSK9-specific nuclease activity

| Pair | % Indel |
|---|---|
| 60045_60043 | 65.40 |
| 60134_60133 | 72.63 |
| 60137_60334 | 67.90 |
| 60259_60254 | 75.69 |
| 60259_60256 | 74.32 |
| 60289_60287 | 73.07 |
| 60309_60308 | 71.77 |

Zinc finger nucleases were also designed against the *Macacca mulatta* PCSK9 gene (mmPCSK9), and are shown below in Table 3.

TABLE 3

M. mulatta PCSK9 zinc finger protein designs

| SBS #/<br>Target/<br>exon | Design | | | | | | Linker-<br>Fok<br>domain |
|---|---|---|---|---|---|---|---|
| | F1 | F2 | F3 | F4 | F5 | F6 | |
| SBS# 69903<br>5'gtGGAGGC<br>TGCCCGGCAC<br>CTacgtggtg<br>(SEQ ID<br>NO: 143),<br>exon 2 | TGQTLRG<br>(SEQ ID<br>NO: 147) | QNATRTK<br>(SEQ ID<br>NO: 45) | RSDNLSE<br>(SEQ ID<br>NO: 95) | SKQYLIK<br>(SEQ ID<br>NO: 148) | DRSHLTR<br>(SEQ ID<br>NO: 59) | QSGHLSR<br>(SEQ ID<br>NO: 22) | N7a*<br>ELD |
| SBS# 69912<br>5'gtGGTGCT<br>GAAGGAGGAG<br>ACccaccgct<br>(SEQ ID<br>NO: 144),<br>exon 2 | DRSNLSR<br>(SEQ ID<br>NO: 91) | QSGHLSR<br>(SEQ ID<br>NO: 22) | QSGHLQR<br>(SEQ ID<br>NO: 149) | QSGNLAR<br>(SEQ ID<br>NO: 14) | QSSDLSR<br>(SEQ ID<br>NO: 15) | TSGHLSR<br>(SEQ ID<br>NO: 21) | L0<br>KKR |
| SBS# 69908<br>5'gtGGAGGC<br>TGCCCGGCAC<br>CTacgtggtg<br>(SEQ ID<br>NO: 143),<br>exon 2 | YKWDLNN<br>(SEQ ID<br>NO: 150) | QNATRTK<br>(SEQ ID<br>NO: 45) | RSDTLSE<br>(SEQ ID<br>NO: 46) | QKRNRTK<br>(SEQ ID<br>NO: 151) | DRSHLTR<br>(SEQ ID<br>NO: 59) | QSGHLSR<br>(SEQ ID<br>NO: 22) | N7a*<br>ELD |
| SBS# 69909<br>5'gtGGAGGC<br>TGCCCGGCAC<br>CTacgtggtg<br>(SEQ ID<br>NO: 143),<br>exon 2 | TGQTLRG<br>(SEQ ID<br>NO: 147) | QNATRTK<br>(SEQ ID<br>NO: 45) | RSDTLSE<br>(SEQ ID<br>NO: 46) | QKRNRTK<br>(SEQ ID<br>NO: 151) | DRSHLTR<br>(SEQ ID<br>NO: 59) | QSGHLSR<br>(SEQ ID<br>NO: 22) | N7a*<br>ELD |

TABLE 3-continued

M. mulatta PCSK9 zinc finger protein designs

| SBS #/ Target/ exon | Design | | | | | | Linker-Fok domain |
|---|---|---|---|---|---|---|---|
| | F1 | F2 | F3 | F4 | F5 | F6 | |
| SBS# 69913 5'gtGGTGCT GAAGGAGGAG ACccaccgct (SEQ ID NO: 144), exon 2 | DRSNLSR (SEQ ID NO: 91) | QSGHLSR (SEQ ID NO: 22) | QSGHLAR (SEQ ID NO: 72) | QSGNLAR (SEQ ID NO: 14) | QSSDLSR (SEQ ID NO: 15) | TSGHLSR (SEQ ID NO: 21) | L0 KKR |
| SBS# 69915 5'gtGGGACA TCGCAGGCTG CTgcccacgt (SEQ ID NO: 145), exon 7 | QSSDLSR (SEQ ID NO: 15) | QSSDLRR (SEQ ID NO: 71) | RSDNLSA (SEQ ID NO: 152) | RNNDRKT (SEQ ID NO: 153) | DRSDLSR (SEQ ID NO: 154) | RSHHLKA (SEQ ID NO: 155) | N7a* ELD |
| SBS# 69922 5'ggGGTGGT GACTTACCAG CCacgtgggc (SEQ ID NO: 146), exon 7 | DRSTRTK (SEQ ID NO: 156) | RRDTLLD (SEQ ID NO: 157) | QSAVLPG (SEQ ID NO: 158) | DRSNLTR (SEQ ID NO: 99) | LKQNLDA (SEQ ID NO: 159) | LRHHLTR (SEQ ID NO: 17) | N7a* KKR |
| SBS# 69925 5'ggGGTGGT GACTTACCAG CCacgtgggc (SEQ ID NO: 146), exon 7 | DRSDLSR (SEQ ID NO: 154) | QSGDLTR (SEQ ID NO: 39) | QSAVLPG (SEQ ID NO: 158) | DRSNLTR (SEQ ID NO: 99) | LKQNLDA (SEQ ID NO: 159) | LRHHLTR (SEQ ID NO: 17) | N7a* KKR |
| SBS# 69928 5'ggGGTGGT GACTTACCAG CCacgtgggc (SEQ ID NO: 146), exon 7 | ERGTLAR (SEQ ID NO: 160) | QSADRTK (SEQ ID NO: 68) | QSAVLPG (SEQ ID NO: 158) | DRSNLTR (SEQ ID NO: 99) | LKQNLDA (SEQ ID NO: 159) | LRHHLTR (SEQ ID NO: 17) | N7a* KKR |
| SBS# 69926 5'ggGGTGGT GACTTACCAG CCacgtgggc (SEQ ID NO: 146), exon 7 | DRSDLSR (SEQ ID NO: 154) | QSGDLTR (SEQ ID NO: 39) | SHLGLTI (SEQ ID NO: 161) | DRSNLTR (SEQ ID NO: 99) | LKQNLDA (SEQ ID NO: 159) | LRHHLTR (SEQ ID NO: 17) | N7a* KKR |
| SBS# 69916 5'gtGGGACA TCGCAGGCTG CTgcccacgt (SEQ ID NO: 145), exon 7 | QSSDLSR (SEQ ID NO: 15) | QSSDLRR (SEQ ID NO: 71) | RSDNLSA (SEQ ID NO: 152) | RSNDRKK (SEQ ID NO: 162) | DRSDLSR (SEQ ID NO: 154) | RSHHLKA (SEQ ID NO: 155) | N7a* ELD |
| SBS# 69918 5'gtGGGACA TCGCAGGCTG CTgcccacgt (SEQ ID NO: 145), exon 7 | QSSDLSR (SEQ ID NO: 15) | QSSDLRR (SEQ ID NO: 71) | RSDNLSA (SEQ ID NO: 152) | RNNDRKT (SEQ ID NO: 153) | QNATRIN (SEQ ID NO: 163) | RSAHLSR (SEQ ID NO: 26) | N7a* ELD |
| SBS# 69919 5'gtGGGACA TCGCAGGCTG CTgcccacgt (SEQ ID NO: 145), exon 7 | QSSDLSR (SEQ ID NO: 15) | QSSDLRR (SEQ ID NO: 71) | RSDNLSA (SEQ ID NO: 152) | RSNDRKK (SEQ ID NO: 162) | QNATRIN (SEQ ID NO: 163) | RSAHLSR (SEQ ID NO: 26) | N7a* ELD |

TABLE 3-continued

M. mulatta PCSK9 zinc finger protein designs

| SBS #/ Target/ exon | Design | | | | | | Linker- Fok domain |
|---|---|---|---|---|---|---|---|
| | F1 | F2 | F3 | F4 | F5 | F6 | |
| SBS# 69920 5'gtGGGACA TCGCAGGCTG CTgcccacgt (SEQ ID NO: 145), exon 7 | QSSDLSR (SEQ ID NO: 15) | QSSDLRR (SEQ ID NO: 71) | RSDNLST (SEQ ID NO: 108) | RSNDREK (SEQ ID NO: 164) | QNATRIN (SEQ ID NO: 163) | RSAHLSR (SEQ ID NO: 26) | N7a* ELD |
| SBS# 69929 5'ggGGTGGT GACTTACCAG CCacgtgggc (SEQ ID NO: 146), exon 7 | ERGTLAR (SEQ ID NO: 160) | QSADRTK (SEQ ID NO: 68) | SHLGLTI (SEQ ID NO: 161) | DRSNLTR (SEQ ID NO: 99) | LKQNLDA (SEQ ID NO: 159) | LRHHLTR (SEQ ID NO: 17) | N7a* KKR |

*indicates that the DNA binding domain is attached to the FokI nuclease domain at the DNA binding domain's N-terminus (see U.S. Publications Nos. 20170218349 and 20170211075)

Nucleases targeting the *M. mulatta* PCSK9 gene were tested for activity in the Rhesus macaque cell line MK2, and exemplary pairwise combination results are shown below in Table 4. All proteins bound their targets and induced cleavage. The total dose of mRNA encoding each partner of the nuclease pair is indicated, and was added in a 100 μL transfection volume. Activity is shown as % indels measured by deep sequencing (MiSeq, Illumnia) and then analyzed for the percent of alleles comprising insertions and/or deletions at the cleavage site.

TABLE 4

Activity of *M. mullata* PCSK9 ZFN pairs

| Indels (%) | total ug ZFN mRNA | | | | |
|---|---|---|---|---|---|
| Sample | 0 | 0.003 | 0.01 | 0.03 | 0.1 |
| 69903/69912 | 0.05 | 0.17 | 1.93 | 9.08 | 33.74 |
| 69908/69912 | 0.05 | 0.22 | 1.73 | 11.82 | 42.54 |
| 69909/69912 | 0.05 | 0.48 | 4.19 | 21.30 | 58.71 |
| 69909/69913 | 0.05 | 0.56 | 3.63 | 18.28 | 53.39 |
| 69915/69922 | 0.03 | 0.21 | 3.93 | 31.72 | 77.97 |

TABLE 4-continued

Activity of *M. mullata* PCSK9 ZFN pairs

| Indels (%) | total ug ZFN mRNA | | | | |
|---|---|---|---|---|---|
| Sample | 0 | 0.003 | 0.01 | 0.03 | 0.1 |
| 69915/69925 | 0.03 | 0.26 | 1.26 | 25.27 | 71.53 |
| 69915/69928 | 0.03 | 0.20 | 1.16 | 17.96 | 63.41 |
| 69915/69926 | 0.03 | 0.16 | 1.26 | 7.28 | 37.05 |
| 69916/69922 | 0.03 | 0.46 | 5.88 | 27.89 | 81.41 |
| 69916/69925 | 0.03 | 0.56 | 3.28 | 17.00 | 76.97 |
| 69916/69928 | 0.03 | 0.25 | 3.15 | 23.90 | 69.22 |
| 69918/69922 | 0.03 | 0.28 | 2.02 | 21.78 | 71.24 |
| 69918/69925 | 0.03 | 0.14 | 1.75 | 15.82 | 68.68 |
| 69918/69928 | 0.03 | 0.09 | 0.79 | 14.92 | 57.86 |
| 69919/69922 | 0.03 | 0.16 | 2.62 | 26.07 | 76.11 |
| 69919/69925 | 0.03 | 0.25 | 1.82 | 22.85 | 66.23 |
| 69920/69922 | 0.03 | 0.51 | 2.94 | 20.56 | 72.11 |
| 69920/69925 | 0.03 | 0.43 | 2.17 | 18.13 | 71.79 |
| 69920/69928 | 0.03 | 0.27 | 1.51 | 12.35 | 54.45 |
| 69920/69929 | 0.03 | 0.30 | 1.45 | 10.77 | 43.34 |

ZFNs were designed against the mouse PCSK9 (mPCSK9) gene, and are shown below in Table 5.

TABLE 5

Mouse PCSK9 zinc finger protein designs

| SBS #/ Target/exon (site) | Design | | | | | | Linker- Fok domain |
|---|---|---|---|---|---|---|---|
| | F1 | F2 | F3 | F4 | F5 | F6 | |
| SBS# 60422 5'tcGGGAGA TTGAGGGCAG GGtcaccatc (SEQ ID NO: 165), exon 4 (A) | RSAHLSR (SEQ ID NO: 26) | QSGDLTR (SEQ ID NO: 39) | RSDHLSA (SEQ ID NO: 180) | SYWSRTV (SEQ ID NO: 181) | QNAHRKT (SEQ ID NO: 182) | RSAHLSR (SEQ ID NO: 26) | N7a* ELD |
| SBS# 64793 5'tcGGGAGA TTGAGGGCAG GGtcaccatc (SEQ ID NO: 165), exon 4 (A) | RSDHLSR (SEQ ID NO: 27) | QSGDLTR (SEQ ID NO: 39) | RSDHLSA (SEQ ID NO: 180) | SYWSRTV (SEQ ID NO: 181) | QSAHRKN (SEQ ID NO: 183) | RSAHLSR (SEQ ID NO: 26) | N7a* ELD |

TABLE 5-continued

Mouse PCSK9 zinc finger protein designs

| SBS #/Target/exon (site) | Design | | | | | | Linker-Fok domain |
|---|---|---|---|---|---|---|---|
| | F1 | F2 | F3 | F4 | F5 | F6 | |
| SBS# 64802 5'tcGGGAGA TTGAGGGCAG GGtcaccatc (SEQ ID NO: 165), exon 4 (A) | RSDHLSR (SEQ ID NO: 27) | QSSDLTR (SEQ ID NO: 184) | RSDHLSA (SEQ ID NO: 180) | SYWSRTV (SEQ ID NO: 181) | QSAHRKN (SEQ ID NO: 183) | RSAHLSR (SEQ ID NO: 26) | N7a* ELD |
| SBS# 64791 5'tcGGGAGA TTGAGGGCAG GGtcaccatc (SEQ ID NO: 165), exon 4 (A) | RSDHLSR (SEQ ID NO: 27) | QSGDLTR (SEQ ID NO: 39) | RSDHLSA (SEQ ID NO: 180) | SYWSRTV (SEQ ID NO: 181) | QNAHRKT (SEQ ID NO: 182) | RSAHLSR (SEQ ID NO: 26) | N7a* ELD |
| SBS# 60423 5'ggCACGCT GTTGAAGTCG GTgatggtga (SEQ ID NO: 166), exon 4 (A) | TSGHLSR (SEQ ID NO: 21) | DRSALAR (SEQ ID NO: 34) | QSSNLAR (SEQ ID NO: 94) | TSGSLTR (SEQ ID NO: 185) | QSSDLSR (SEQ ID NO: 15) | DRSNRNQ (SEQ ID NO: 186) | N7a* KKR |
| SBS# 64842 5'ggCACGCT GTTGAAGTCG GTgatggtga (SEQ ID NO: 166), exon 4 (A) | TSGHLSR (SEQ ID NO: 21) | TSGSLTR (SEQ ID NO: 185) | QSSNLAR (SEQ ID NO: 94) | QSGSLTR (SEQ ID NO: 67) | QSSDLSR (SEQ ID NO: 15) | DRSNRNQ (SEQ ID NO: 186) | N7a* KKR |
| SBS# 64844 5'ggCACGCT GTTGAAGTCG GTgatggtga (SEQ ID NO: 166), exon 4 (A) | TSGHLSR (SEQ ID NO: 21) | TSGSLTR (SEQ ID NO: 185) | QSSNLAR (SEQ ID NO: 94) | TSGSLTR (SEQ ID NO: 185) | QSSDLSR (SEQ ID NO: 15) | DRSNRNQ (SEQ ID NO: 186) | N7a* KKR |
| SBS# 64836 5'ggCACGCT GTTGAAGTCG GTgatggtga (SEQ ID NO: 166), exon 4 (A) | TSGHLSR (SEQ ID NO: 21) | TSGSLTR (SEQ ID NO: 185) | QSSNLAR (SEQ ID NO: 94) | TSGSLTR (SEQ ID NO: 185) | QSSDLSR (SEQ ID NO: 15) | DRSNRNQ (SEQ ID NO: 186) | N7a* KKR |
| SBS# 60416 5'caGAGCAT CCCATGGAAC CTggagcgaa (SEQ ID NO: 167) exon 3 (B) | HGQTLNE (SEQ ID NO: 187) | QSGNLAR (SEQ ID NO: 14) | RSDVLSN (SEQ ID NO: 188) | DRSTRIT (SEQ ID NO: 189) | LSWNLLT (SEQ ID NO: 190) | RSANLTR (SEQ ID NO: 57) | N7a* ELD |
| SBS# 64859 5'caGAGCAT CCCATGGAAC CTggagcgaa (SEQ ID NO: 167) exon 3 (B) | LQQTLAD (SEQ ID NO: 191) | QSGNLAR (SEQ ID NO: 14) | RSDVLSN (SEQ ID NO: 188) | DRSTRIT (SEQ ID NO: 189) | LKQNLDA (SEQ ID NO: 159) | RSANLTR (SEQ ID NO: 57) | N7a* ELD |
| SBS# 64848 5'caGAGCAT CCCATGGAAC CTggagcgaa (SEQ ID NO: 167) exon 3 (B) | HGQTLNE (SEQ ID NO: 187) | QSGNLAR (SEQ ID NO: 14) | RSDVLSN (SEQ ID NO: 188) | DRSTRIT (SEQ ID NO: 189) | LKQNLDA (SEQ ID NO: 159) | RSANLTR (SEQ ID NO: 57) | N7a* ELD |

TABLE 5-continued

Mouse PCSK9 zinc finger protein designs

| SBS #/ Target/exon (site) | Design | | | | | | Linker-Fok domain |
|---|---|---|---|---|---|---|---|
| | F1 | F2 | F3 | F4 | F5 | F6 | |
| SBS# 64853 5'caGAGCAT CCCATGGAAC CTggagcgaa (SEQ ID NO: 167) exon 3 (B) | LQQTLAD (SEQ ID NO: 191) | QSGNLAR (SEQ ID NO: 14) | RSDVLSN (SEQ ID NO: 188) | DRSTRIT (SEQ ID NO: 189) | LKQNLDA (SEQ ID NO: 159) | RSANLTR (SEQ ID NO: 57) | N7a* ELD |
| SBS# 60417 5'ctGGTGCC ATGCTGGGAT AAttcgctcc (SEQ ID NO: 168) exon 3 (B) | QSANRTK (SEQ ID NO: 192) | DSSHRTR (SEQ ID NO: 42) | RSDALSE (SEQ ID NO: 193) | RSSTRKT (SEQ ID NO: 194) | ERGTLAR (SEQ ID NO: 160) | TSGSLTR (SEQ ID NO: 185) | N7a* KKR |
| SBS# 64866 5'ctGGTGCC ATGCTGGGAT AAttcgctcc (SEQ ID NO: 168) exon 3 (B) | QSANRTK (SEQ ID NO: 192) | DSSHRTR (SEQ ID NO: 42) | RSDVLSE (SEQ ID NO: 19) | RKYSLRV (SEQ ID NO: 195) | ERGTLAR (SEQ ID NO: 160) | TSGSLTR (SEQ ID NO: 185) | N7a* KKR |
| SBS# 64876 5'ctGGTGCC ATGCTGGGAT AAttcgctcc (SEQ ID NO: 168) exon 3 (B) | QSANRTK (SEQ ID NO: 192) | DSSHRTR (SEQ ID NO: 42) | RSDALSE (SEQ ID NO: 193) | RSSTRKT (SEQ ID NO: 194) | ERGTLAR (SEQ ID NO: 160) | TSGSLTR (SEQ ID NO: 185) | N7a* KKR |
| SBS# 64869 5'ctGGTGCC ATGCTGGGAT AAttcgctcc (SEQ ID NO: 168) exon 3 (B) | QSANRTK (SEQ ID NO: 192) | QSGHLSR (SEQ ID NO: 22) | RSDALSE (SEQ ID NO: 193) | RSSTRKT (SEQ ID NO: 194) | ERGTLAR (SEQ ID NO: 160) | TSGSLTR (SEQ ID NO: 185) | N7a* KKR |
| SBS# 60474 5'gaGCTGCG GCAGAGGCTG ATccacttct (SEQ ID NO: 169) exon 8 (D) | TSGNLTR (SEQ ID NO: 36) | LSQDLNR (SEQ ID NO: 196) | RSDNLAR (SEQ ID NO: 52) | QNVSRPR (SEQ ID NO: 197) | RSDDLTR (SEQ ID NO: 37) | QSSDLRR (SEQ ID NO: 71) | N6a* ELD |
| SBS# 64912 5'gaGCTGCG GCAGAGGCTG ATccacttct (SEQ ID NO: 169) exon 8 (D) | TSGNLTR (SEQ ID NO: 36) | LSQDLNR (SEQ ID NO: 196) | RSDNLAR (SEQ ID NO: 52) | QSGDLTR (SEQ ID NO: 39) | RSDSLSV (SEQ ID NO: 125) | RSADLSR (SEQ ID NO: 105) | N6a* |
| SBS# 60475 5'ttGATGAC GTCTTTGGTA GAgaagtgga (SEQ ID NO: 170) exon 8 (D) | QNAHRKT (SEQ ID NO: 182) | LRHHLTR (SEQ ID NO: 17) | TPSYLPT (SEQ ID NO: 33) | DRSALAR (SEQ ID NO: 34) | DRSNLSR (SEQ ID NO: 91) | TSGNLTR (SEQ ID NO: 36) | N6a* KKR |
| SBS# 64928 5'ttGATGAC GTCTTTGGTA GAgaagtgga (SEQ ID NO: 170) exon 8 (D) | QNAHRKT (SEQ ID NO: 182) | LRHHLTR (SEQ ID NO: 17) | SLTYLPT (SEQ ID NO: 198) | DRSALAR (SEQ ID NO: 34) | DRSNLSR (SEQ ID NO: 91) | TSANLSR (SEQ ID NO: 199) | N6a* KKR |

TABLE 5-continued

Mouse PCSK9 zinc finger protein designs

| SBS #/ Target/exon (site) | Design | | | | | | Linker- Fok domain |
|---|---|---|---|---|---|---|---|
| | F1 | F2 | F3 | F4 | F5 | F6 | |
| SBS# 60412 5'gcTAAGTG cATGGCTGTC TGGttctgta (SEQ ID NO: 171) exon 3 (E) | RWQYLPT (SEQ ID NO: 200) | DRSALAR (SEQ ID NO: 34) | QSSDLSR (SEQ ID NO: 15) | RKDALVA (SEQ ID NO: 201) | RSHSLLR (SEQ ID NO: 202) | QSANRTK (SEQ ID NO: 192) | N7a* ELD |
| SBS# 64946 5'gcTAAGTG cATGGCTGTC TGGttctgta (SEQ ID NO: 171) exon 3 (E) | RSDHLST (SEQ ID NO: 69) | DRSALAR (SEQ ID NO: 34) | QSSDLSR (SEQ ID NO: 15) | RRDALLM (SEQ ID NO: 203) | RSHSLLR (SEQ ID NO: 202) | QSANRTK (SEQ ID NO: 192) | N7a* ELD |
| SBS# 64944 5'gcTAAGTG cATGGCTGTC TGGttctgta (SEQ ID NO: 171) exon 3 (E) | RSDHLST (SEQ ID NO: 69) | DRSALAR (SEQ ID NO: 34) | QSSDLSR (SEQ ID NO: 15) | RKDALVA (SEQ ID NO: 201) | RSHSLLR (SEQ ID NO: 202) | QSANRTK (SEQ ID NO: 192) | N7a* ELD |
| SBS# 64947 5'gcTAAGTG cATGGCTGTC TGGttctgta (SEQ ID NO: 171) exon 3 (E) | RSDHLSA (SEQ ID NO: 180) | DRSALAR (SEQ ID NO: 34) | QSSDLSR (SEQ ID NO: 15) | RKDALVA (SEQ ID NO: 201) | RSHSLLR (SEQ ID NO: 202) | QSANRTK (SEQ ID NO: 192) | N7a* ELD |
| SBS# 60413 5'caCATGGG GCAACTtCAG GGCctacaga (SEQ ID NO: 172) exon 3 (E) | DSSHRTR (SEQ ID NO: 42) | AKWNLDA (SEQ ID NO: 204) | QHQVLVR (SEQ ID NO: 44) | QNATRTK (SEQ ID NO: 45) | RSDHLSR (SEQ ID NO: 27) | TSSNRKT (SEQ ID NO: 126) | N7a* KKR |
| SBS# 64951 5'caCATGGG GCAACTtCAG GGCctacaga (SEQ ID NO: 172) exon 3 (E) | DSSHRTR (SEQ ID NO: 42) | AKWNLDA (SEQ ID NO: 204) | HASTLQN (SEQ ID NO: 205) | QNATRTK (SEQ ID NO: 45) | RSDHLSR (SEQ ID NO: 27) | TSSNRKT (SEQ ID NO: 126) | N7a* KKR |
| SBS# 64950 5'caCATGGG GCAACTtCAG GGCctacaga (SEQ ID NO: 172) exon 3 (E) | DSSHRTR (SEQ ID NO: 42) | AKWNLDA (SEQ ID NO: 204) | HASTLQN (SEQ ID NO: 205) | QNATRTK (SEQ ID NO: 45) | RSDHLSR (SEQ ID NO: 27) | TSSNRKT (SEQ ID NO: 126) | N7a* KKR |
| SBS# 64952 5'caCATGGG GCAACTtCAG GGCctacaga (SEQ ID NO: 172) exon 3 (E) | DRSHLTR (SEQ ID NO: 59) | RSDNLRE (SEQ ID NO: 206) | QHQVLVR (SEQ ID NO: 44) | QNATRTK (SEQ ID NO: 45) | RSDHLSR (SEQ ID NO: 27) | TSSNRKT (SEQ ID NO: 126) | N7a* KKR |
| SBS# 60460 5'gtGGGACC TCACAGGCTG CTgcccacgt (SEQ ID NO: 173) exon 7 (F) | QSSDLSR (SEQ ID NO: 15) | HRSTRNR (SEQ ID NO: 207) | RSDNLSQ (SEQ ID NO: 208) | ASNDRKK (SEQ ID NO: 209) | ASKTRTN (SEQ ID NO: 210) | RSAHLSR (SEQ ID NO: 26) | N7a* ELD |

TABLE 5-continued

Mouse PCSK9 zinc finger protein designs

| SBS #/Target/exon (site) | Design | | | | | | Linker-Fok domain |
|---|---|---|---|---|---|---|---|
| | F1 | F2 | F3 | F4 | F5 | F6 | |
| SBS# 64971 5'gtGGGACC TCACAGGCTG CTgcccacgt (SEQ ID NO: 173) exon 7 (F) | QSSDLSR (SEQ ID NO: 15) | QSSDLRR (SEQ ID NO: 71) | RSDNLSQ (SEQ ID NO: 208) | ASNDRKK (SEQ ID NO: 209) | DRSDLSR (SEQ ID NO: 154) | RSHHLKA (SEQ ID NO: 155) | N7a* ELD |
| SBS# 64969 5'gtGGGACC TCACAGGCTG CTgcccacgt (SEQ ID NO: 173) exon 7 (F) | QSSDLSR (SEQ ID NO: 15) | HRSTRNR (SEQ ID NO: 207) | RSDNLSQ (SEQ ID NO: 208) | ASNDRKK (SEQ ID NO: 209) | DRSDLSR (SEQ ID NO: 154) | RSHHLKA (SEQ ID NO: 155) | N7a* ELD |
| SBS# 64968 5'gtGGGACC TCACAGGCTG CTgcccacgt (SEQ ID NO: 173) exon 7 (F) | QSSDLSR (SEQ ID NO: 15) | QSSDLRR (SEQ ID NO: 71) | RSDNLSQ (SEQ ID NO: 208) | ASNDRKK (SEQ ID NO: 209) | DRSDLSR (SEQ ID NO: 154) | RSHHLKA (SEQ ID NO: 155) | N7a* ELD |
| SBS# 60461 5'ggGGTGGT GACTCACCGG CCacgtgggc (SEQ ID NO: 175) exon 7 (F) | DRSTRTK (SEQ ID NO: 156) | RRDTLLD (SEQ ID NO: 157) | QSADRTK (SEQ ID NO: 68) | DRSNLTR (SEQ ID NO: 99) | LRHHLTR (SEQ ID NO: 17) | LKQHLTR (SEQ ID NO: 211) | N7a* KKR |
| SBS# 64983 5'ggGGTGGT GACTCACCGG CCacgtgggc (SEQ ID NO: 175) exon 7 (F) | DRSTRTK (SEQ ID NO: 156) | RRDTLLD (SEQ ID NO: 157) | QSSDLSR (SEQ ID NO: 15) | DRSNLTR (SEQ ID NO: 99) | HKQHRDA (SEQ ID NO: 18) | LRHHLTR (SEQ ID NO: 17) | N7a* KKR |
| SBS# 64982+ 5'ggGGTGGT GACTCACCGG CCacgtgggc (SEQ ID NO: 175) exon 7 (F) | DRSTRTK (SEQ ID NO: 156) | RRDTLLD (SEQ ID NO: 157) | QSSDLSR (SEQ ID NO: 15) | DRSNLTR (SEQ ID NO: 99) | LKQNLDA (SEQ ID NO: 159) | LRHHLTR (SEQ ID NO: 17) | N7a* KKR |
| SBS# 64972+ 5'ggGGTGGT GACTCACCGG CCacgtgggc (SEQ ID NO: 175) exon 7 (F) | DRSTRTK (SEQ ID NO: 156) | RRDTLLD (SEQ ID NO: 157) | QSSDLSR (SEQ ID NO: 15) | DRSNLTR (SEQ ID NO: 99) | LKQNLDA (SEQ ID NO: 159) | LRHHLTR (SEQ ID NO: 17) | N7a* KKR |
| SBS# 60392 5'agGATGGA GATTATGAAG AGctgatgct (SEQ ID NO: 176) exon 1 (G) | RSANLAR (SEQ ID NO: 111) | QSANRTK (SEQ ID NO: 192) | TSSNRKT (SEQ ID NO: 126) | TSSNLSR (SEQ ID NO: 24) | DRSHLSR (SEQ ID NO: 212) | TSGNLTR (SEQ ID NO: 36) | N7a* ELD |
| SBS# 64989 5'agGATGGA GATTATGAAG AGctgatgct (SEQ ID NO: 176) exon 1 (G) | RSANLAR (SEQ ID NO: 111) | QSGNLAR (SEQ ID NO: 14) | TSSNRKT (SEQ ID NO: 126) | TSSNLSR (SEQ ID NO: 24) | QSGHLQR (SEQ ID NO: 149) | TSGNLTR (SEQ ID NO: 36) | N7a* ELD |

TABLE 5-continued

Mouse PCSK9 zinc finger protein designs

| SBS #/ Target/exon (site) | Design | | | | | | Linker-Fok domain |
|---|---|---|---|---|---|---|---|
| | F1 | F2 | F3 | F4 | F5 | F6 | |
| SBS# 64992 5'agGATGGA GATTATGAAG AGctgatgct (SEQ ID NO: 176) exon 1 (G) | RSANLAR (SEQ ID NO: 111) | TSANLSR (SEQ ID NO: 199) | TSSNRKT (SEQ ID NO: 126) | TSSNLSR (SEQ ID NO: 24) | QSGHLQR (SEQ ID NO: 149) | TSGNLTR (SEQ ID NO: 36) | N7a* ELD |
| SBS# 60393 5'tcCTCCTG GGACGGgAGG GCGagcatca (SEQ ID NO: 177) exon 1 (G) | RSADLTR (SEQ ID NO: 213) | RSDHLTQ (SEQ ID NO: 214) | RSDHLSE (SEQ ID NO: 30) | QSHHRKT (SEQ ID NO: 215) | RSDVLSE (SEQ ID NO: 19) | SPSSRRT (SEQ ID NO: 216) | N7a* KKR |
| SBS# 65021 5'tcCTCCTG GGACGGgAGG GCGagcatca (SEQ ID NO: 177) exon 1 (G) | RSADLTR (SEQ ID NO: 213) | RSDHLTQ (SEQ ID NO: 214) | RSDHLSE (SEQ ID NO: 30) | QSGHLSR (SEQ ID NO: 22) | RSDVLSE (SEQ ID NO: 19) | SPSSRRT (SEQ ID NO: 216) | N7a* KKR |
| SBS# 65022 5'tcCTCCTG GGACGGgAGG GCGagcatca (SEQ ID NO: 177) exon 1 (G) | RSADLTR (SEQ ID NO: 213) | RSDHLTQ (SEQ ID NO: 214) | RSDHLSE (SEQ ID NO: 30) | NSSSRIK (SEQ ID NO: 217) | RSDVLSE (SEQ ID NO: 19) | SPSSRRT (SEQ ID NO: 216) | N7a* KKR |
| SBS# 58781 5'gtGGTGCT GATGGAGGAG ACccagaggc (SEQ ID NO: 178) exon 2 (J) | DRSNLSR (SEQ ID NO: 91) | QSGHLSR (SEQ ID NO: 22) | DRSHLSR (SEQ ID NO: 212) | TSGNLTR (SEQ ID NO: 36) | QSSDLSR (SEQ ID NO: 15) | WHSSLHQ (SEQ ID NO: 16) | L0 KKR |
| SBS# 65098 5'gtGGTGCTG ATGGAGGAG ACccagaggc (SEQ ID NO: 178) exon 2 (J) | DRSNLSR (SEQ ID NO: 91) | QSGHLSR (SEQ ID NO: 22) | QSSHLTR (SEQ ID NO: 13) | TSANLSR (SEQ ID NO: 199) | QSSDLSR (SEQ ID NO: 15) | TSGHLSR (SEQ ID NO: 21) | L0 KKR |
| SBS# 65094 5'gtGGTGCT GATGGAGGAG ACccagaggc (SEQ ID NO: 178) exon 2 (J) | DRSNLSR (SEQ ID NO: 91) | QSGHLSR (SEQ ID NO: 22) | DRSHLSR (SEQ ID NO: 212) | TSANLSR (SEQ ID NO: 199) | QSSDLSR (SEQ ID NO: 15) | TSGHLSR (SEQ ID NO: 21) | L0 KKR |
| SBS# 65095 5'gtGGTGCT GATGGAGGAG ACccagaggc (SEQ ID NO: 178) exon 2 (J) | DRSNLSR (SEQ ID NO: 91) | QSGHLSR (SEQ ID NO: 22) | DRSHLSR (SEQ ID NO: 212) | TSANLSR (SEQ ID NO: 199) | QSSDLSR (SEQ ID NO: 15) | HRHHLIR (SEQ ID NO: 218) | L0 KKR |

TABLE 5-continued

Mouse PCSK9 zinc finger protein designs

| SBS #/Target/exon (site) | F1 | F2 | F3 | F4 | F5 | F6 | Linker-Fok domain |
|---|---|---|---|---|---|---|---|
| SBS# 58780 5'ctGGAGGC TGCCAGGAAC CTacattgtg (SEQ ID NO: 179) exon 2 (J) | HGQTLNE (SEQ ID NO: 187) | QSGNLAR (SEQ ID NO: 14) | RSDNLSE (SEQ ID NO: 95) | SKQYLIK (SEQ ID NO: 148) | DRSHLTR (SEQ ID NO: 59) | QSGHLSR (SEQ ID NO: 22) | N7a* ELD |
| SBS# 65086 5'ctGGAGGC TGCCAGGAAC CTacattgtg (SEQ ID NO: 179) exon 2 (J) | LQQTLAD (SEQ ID NO: 191) | QSGNLAR (SEQ ID NO: 14) | RSDNLSE (SEQ ID NO: 95) | SKQYLIK (SEQ ID NO: 148) | DRSHLTR (SEQ ID NO: 59) | QSGHLSR (SEQ ID NO: 22) | N7a* ELD |
| SBS# 65085 5'ctGGAGGC TGCCAGGAAC CTacattgtg (SEQ ID NO: 179) exon 2 (J) | LQQTLAD (SEQ ID NO: 191) | QSGNLAR (SEQ ID NO: 14) | RSDNLSE (SEQ ID NO: 95) | RGDRRNK (SEQ ID NO: 219) | DRSHLTR (SEQ ID NO: 59) | QSGHLSR (SEQ ID NO: 22) | N7a* ELD |

*indicates that the DNA binding domain is attached to the FokI nuclease domain at the DNA binding domain's N-terminus (see U.S. Publication Nos. 20170218349 and 20170211075).
†SBS# 64982 and SBS# 64972 have the same helices and FokI domains, but differ in the the finger linkers; specifically in the linker between F2 and F3.

Nucleases targeting the murine PCSK9 gene (mPCSK9) shown above were tested for activity in the murine liver cell line Hepa1-6 at 0.1 ug total ZFN mRNA dose, where half of the dose is each individual ZFN. ZFNs were added in a 100 µL transfection volume. All proteins bound to their targets and induced cleavage. Exemplary activity (% indel) results of pairwise combinations are shown below in Tables 6A through 6G at the specific sites shown in FIG. 6. % Indels were measured by deep sequencing (MiSeq, Illumnia) and then analyzed for the percent of alleles comprising insertions and/or deletions at the cleavage site.

TABLE 6A mPCSK9 ZFN, Site A

| Site A | 60423 | 64842 | 64844 | 64836 |
|---|---|---|---|---|
| 60422 | 16.4 | 35.0 | 26.8 | 26.7 |
| 64793 | 35.8 | 44.9 | 42.9 | 37.3 |
| 64802 | 30.6 | 43.0 | 41.6 | 37.0 |
| 64791 | 34.0 | 41.8 | 41.7 | 38.0 |

TABLE 6B mPCSK9 ZFN, Site B

| Site B | 60417 | 64866 | 64876 | 64869 |
|---|---|---|---|---|
| 60416 | 13.9 | 35.7 | 32.4 | 30.9 |
| 64859 | 53.0 | 79.0 | 71.2 | 82.4 |
| 64848 | 36.2 | 73.6 | 64.8 | 73.0 |
| 64853 | 31.9 | 66.5 | 58.6 | 64.3 |

TABLE 6C mPCSK9 ZFN, Site D

| Site D | 60475 | 64928 |
|---|---|---|
| 60474 | 0.1 | 0.1 |
| 64912 | 0.0 | 0.1 |

TABLE 6D mPCSK9 ZFN, Site E

| Site E | 60413 | 64951 | 64950 | 64952 |
|---|---|---|---|---|
| 60412 | 22.8 | 28.6 | 20.6 | 23.5 |
| 64946 | 35.4 | 51.3 | 45.2 | 45.3 |
| 64944 | 41.4 | 48.8 | 38.7 | 49.1 |
| 64947 | 28.8 | 38.3 | 29.9 | 42.0 |

TABLE 6E mPCSK9 ZFN, Site F

| Site F | 60461 | 64983 | 64982 | 64972 |
|---|---|---|---|---|
| 60460 | 27.2 | 50.5 | 53.8 | 23.7 |
| 64971 | 85.8 | 95.2 | 95.9 | 89.0 |
| 64969 | 69.1 | 79.4 | 86.1 | 69.8 |

TABLE 6F mPCSK9 ZFN, Site G

| Site G | 60393 | 65021 | 65022 | |
|---|---|---|---|---|
| 60392 | 53.7 | 68.1 | 69.2 | |
| 64989 | 60.9 | 83.3 | 76.3 | |
| 64992 | 51.4 | 79.8 | 69.1 | |
| 64968 | 70.7 | 78.4 | 86.3 | 67.4 |

TABLE 6G mPCSK9 ZFN, Site J

| Site J | 58780 | 65086 | 65085 |
|---|---|---|---|
| 58781 | 40.5 | 62.3 | 54.1 |
| 65098 | 67.4 | 77.2 | 73.5 |
| 65094 | 69.6 | 77.8 | 73.3 |
| 65095 | 64.2 | 76.7 | 72.1 |

Correlation between % indels and knockdown of secreted mPCSK9 protein in the transduced Hepa1-6 cell supernatant is calculated. Two doses are evaluated (Low dose is 0.5 ug total ZFN mRNA dose and high dose is 4 ug total ZFN mRNA dose), and mPCSK9 protein concentration is measured by ELISA at 3 days post transduction ("3DPT"). The analysis demonstrates a decrease in mPCSK9 concentration in the supernatant that correlates to the percent indels induced by the ZFN.

II. Nuclease Targeting of SERPINA

Zinc finger nucleases were designed to cleave the SERPINA gene flanking the location of the Z mutation (FIG. 1), Table 7, (see also Yusa et al (2011) Nature 478(7369):391-394). The zinc finger proteins were tested in HepG2 cells and K562 cells and the results are shown below in Table 8. "Linker" indicates that the DNA binding domain is attached to the FokI nuclease domain at the DNA binding domain's N-terminus.

TABLE 7

SERPINA1-specific ZFN

| SBS #/Target | F1 | F2 | F3 | F4 | F5 | Linker |
|---|---|---|---|---|---|---|
| SBS#25264 5' gtCGATGGT CAGCAcagcctt atgcacg (SEQ ID NO: 65) | QSGSLTR (SEQ ID NO: 67) | QSADRTK (SEQ ID NO: 68) | RSDHLST (SEQ ID NO: 69) | QSAHRIT (SEQ ID NO: 70) | N/A | L0 |
| SBS#25277 5' gaAAGGGAc tGAAGCTGCTgg ggccatg (SEQ ID NO: 66) | QSSDLRR (SEQ ID NO: 71) | QSSDLSR (SEQ ID NO: 15) | QSGNLAR (SEQ ID NO: 14) | QSGHLAR (SEQ ID NO: 72) | RLDNRTA (SEQ ID NO: 73) | L0 |

TABLE 8

Activity of SERPINA1-specific ZFN in vitro

| Pair used, concentration | % Indels, HepG2 cells | % Indels, K562 cells |
|---|---|---|
| 25264_25277_100ng | 4.46% | 23.03% |
| 25264_25277_200ng | 5.31% | 40.91% |
| 25264_25277_400ng | 6.09% | 40.68% |
| 25264_25277_800ng | 3.15% | 27.02% |

Exemplary ZFNs were then used in combination with an oligonucleotide donor that would correct the G→A mutation responsible for the 'Z' mutation. In addition, the oligonucleotide comprised silent nucleotide alterations in the ZFN target sequences that would prevent cleavage of the oligonucleotide once integrated (FIG. 1B). In particular, the nucleotides recognized by Fingers 2 and 4 (TCA and CGA, respectively) of SBS #25264 are altered such that these triplets are TGA and CAA (variant SMS24). These new sequences will no longer be targeted by the SBS #25264 ZFN, and so once the oligonucleotide is integrated, cleavage will no longer occur. The SMS24 SERPINA1 variant oligonucleotide also comprised homology arms that were homologous to the SERPINA1 sequence flanking the cleavage site. When the SMS24 variant oligonucleotide was used with the SERPINA1-specific ZFNs, targeted integration of the oligonucleotide occurred at approximately 4% of alleles in HepG2 cells and 25% of alleles in K562 cells (see Table 9).

TABLE 9

ZFN mediated integration of corrective oligonucleotide in vitro

| | HepG2 | | K562 | |
|---|---|---|---|---|
| | % NHEJ | % TI | % NHEJ | % TI |
| SMS24 + ZFNs | 15.42 | 4.36 | 28.71 | 24.88 |
| ZFNs | 12.75 | 0.00 | 41.13 | 0 |
| SMS24 | 0.44 | 0.07 | 0.12 | 0.08 |

Next, the corrective oligonucleotide and SERPINA1-specific ZFNs were tested in vivo in PiZ mice, a strain comprising approximately 10 copies of the PiZ variant of the human SERPINA1 gene integrated into its germline (Carlson et al (1989) J. Clin Invest. 83: 1183-1190). PiZ mice are transgenic for the mutant human SERPINA1 ("SA1-ATZ") and exhibit ATZ accumulation in hepatocytes and liver fibrosis. The SMS24 oligonucleotide and the ZFN pair were both delivered by AAV8 vectors via the intravenous route and groups of mice were sacrificed 2 weeks and 6 months after treatment for molecular, histological, and biochemical analyses. Untreated age/sex matched PiZ mice were used as controls. Table 10 shows the experimental outline and the injection schedules.

TABLE 10

In vivo testing of ZFN-mediated integration of a corrective oligonucleotide donor

| Group | Test Article #1 | Dose #1 (vg/mouse) | Volume/ dose #1 (uL) | Test Article #1 Injections, mice Day 0 | Test Article #2 | Dose #2 (vg/mouse) | Volume/dose #2 (uL) | Test Article #2 Injections, mice Day 0 | Sacrifice 2 weeks | Sacrifice 6 months | Total |
|---|---|---|---|---|---|---|---|---|---|---|---|
| 1 | SMS24 AAV8 | 1.5E+12 | 200 | 6 | | | | | 3 | 3 | 6 |
| 2 | | | | | 25264/25 277 AAV8 | 7.5E+10 | 200 | 6 | 3 | 3 | 6 |
| 3 | | | | | 25264/25 277 AAV8 | 1.5E+11 | 200 | 6 | 3 | 3 | 6 |
| 4 | SMS24 AAV8 | 1.5E+12 | 200 | 6 | 25264/25 277 AAV8 | 7.5E+10 | 200 | 6 | 3 | 3 | 6 |
| 5 | SMS24 AAV8 | 1.5E+12 | 200 | 6 | 25264/25 277 AAV8 | 1.5E+11 | 200 | 6 | 3 | 3 | 6 |

Figure 2A:
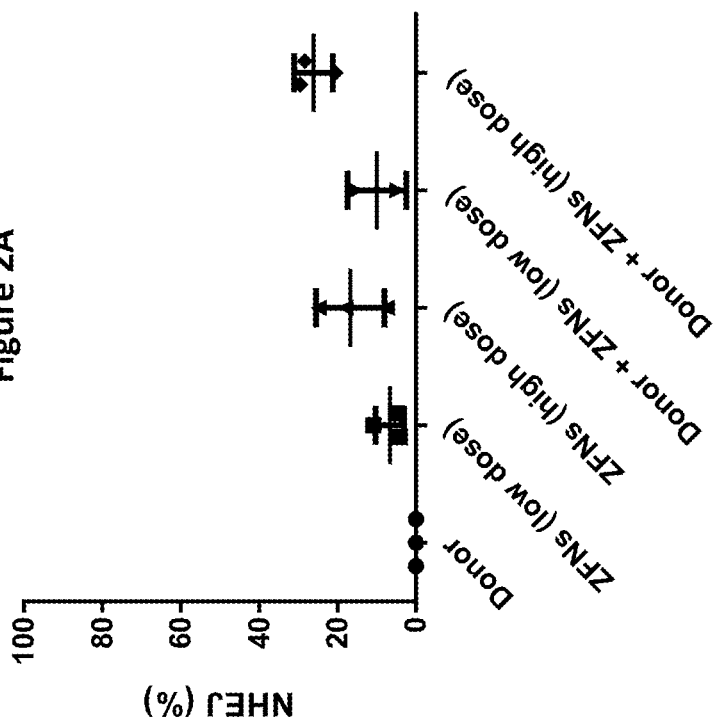
Figure 3C:
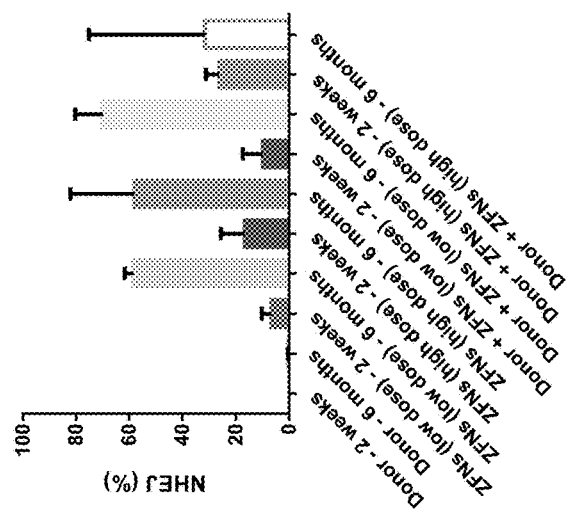
FIGS. 3A through 3C are graphs showing the NHEJ and TI data in mice that had been treated with ZFN and/or the gene correction donor where the animals were sacrificed at 6 months.
Figure 3B:
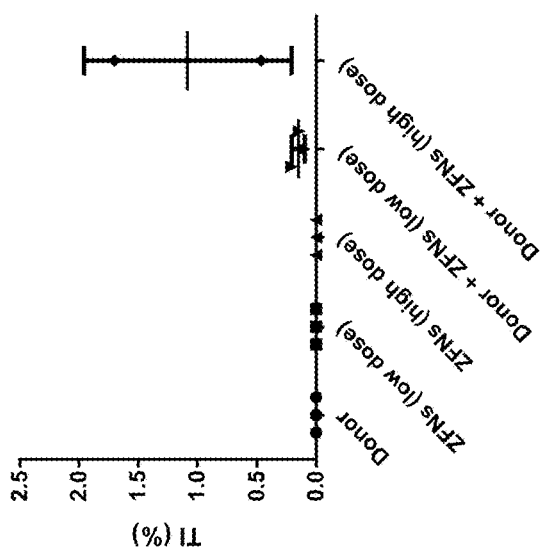
Figure 3A:
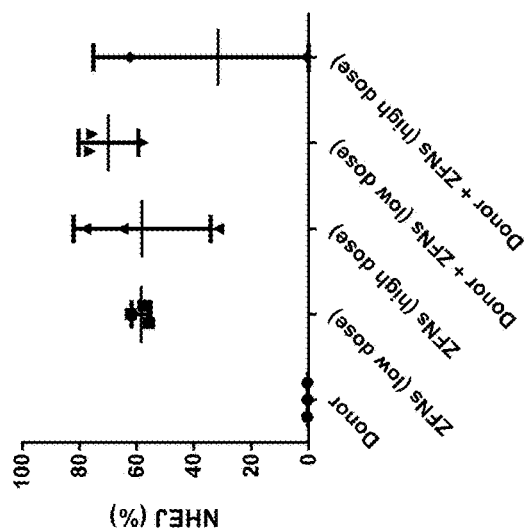

Half of each cohort in the experiment was sacrificed two weeks following injection and the liver tissues were examined for the percent of alleles with NHEJ or targeted integration (TI) at the cleavage site. The results demonstrated that higher doses of ZFNs lead to increased cleavage activity (FIG. 2A), and higher doses of ZFNs in the presence of the oligonucleotide donor lead to higher amounts of TI (FIG. 2B). At six months following injection, the second half of the cohorts were sacrificed. Liver analysis showed that there was a larger percent of alleles displaying NHEJ activity in all cohorts at six months than at two weeks (FIG. 3C). The clear increased in the percent of NHEJ bearing cells may be indicative of a selective advantage for those cells bearing a knock out of the PiZ alleles. In contrast, the amount of TI detected comprising the corrective oligo was not significantly different than the two week samples (FIG. 3B). More specifically, two weeks after treatment, deep sequencing of the hepatic SA1-ATZ gene pool showed 8+4% or 23+8% non-homologous end joining (NHEJ) respectively in mice receiving low dose or high dose rAAV-ZFN. When the rAAV-TI was co-administered with low dose or high dose of rAAV-ZFN, gene repair by targeted insertion (TI) of the normal AAT sequence occurred in 0.25+0.2% and 0.5+0.4 of SA1-ATZ genes. ZFN treatment reduced the number of PiZ globule-containing hepatocytes in liver at 6 months, indicating liver repopulation by genome-edited hepatocytes, as assayed by Diastase/periodic acid Schiff stain. At this time point, serum human ATZ levels declined by 30+6 and 40+5% in the low dose and high dose groups, respectively, compared with controls. Six months after treatment, the percentage of cells with NHEJ in the SA1-ATZ genes increased to 64+8% and 58+20% of recipients of low dose or high dose rAAV-ZFNs, respectively. In mice receiving high dose rAAV-ZFN plus rAAV-TI, up to 1.7% of SA1-ATZ genes showed gene correction. In parallel, serum ATZ levels declined by 47% and 70% in the low dose and high dose rAAV-ZFN recipients, respectively, and liver fibrosis, as measured by Sirius red staining, was greatly reduced compared with controls.

Thus, nuclease-mediated editing of the SA1-ATZ transgene in vivo appears to provide a proliferative advantage to PiZ mouse hepatocytes, allowing them to massively repopulate the liver and reverse hepatic fibrosis, indicating its use as a therapeutic for ATD.

III. Nuclease Targeting of TTR

TTR-specific zinc finger proteins were made to target murine and human TTR as described above. Several regions in the TTR gene were identified for potentially targeting (see, e.g., FIG. 4). Exemplary proteins as well as target sites and exemplary linkers and FokI mutations are shown below in Table 11.

TABLE 11

TTR-Specific ZFN designs

| SBS #/Target | F1 | F2 | F3 | F4 | F5 | F6 | Linker/ Fok | region |
|---|---|---|---|---|---|---|---|---|
| Mouse TTR | | | | | | | | |
| SBS#59642 5'ctTTGCCTcG CTGGACTGgta tttgtgt (SEQ ID NO: 74) | RSDVLSE (SEQ ID NO: 19) | QSGHLSR (SEQ ID NO: 22) | QSSDLSR (SEQ ID NO: 15) | QSSDLSR (SEQ ID NO: 15) | RLYTLHK (SEQ ID NO: 90) | N/A | L0/ N- ELD | C Ex 1 |
| SBS#59199 5'ccGCGGGGC CAGCTTCAG ACacaaatac (SEQ ID NO: 75) | DRSNLSR (SEQ ID NO: 91) | QSADRTK (SEQ ID NO: 68) | QSSDLSR (SEQ ID NO: 15) | QRSTLKS (SEQ ID NO: 92) | RSAHLSR (SEQ ID NO: 26) | RSDDLTR (SEQ ID NO: 37) | N7a/ N- KKR | C Ex 1 |

TABLE 11-continued

TTR-Specific ZFN designs

| SBS #/Target | F1 | F2 | F3 | F4 | F5 | F6 | Linker/Fok | region |
|---|---|---|---|---|---|---|---|---|
| SBS#59667 5'ccGCGGGGC CAGCTTCAG ACacaaatac (SEQ ID NO: 75) | DRSNLSR (SEQ ID NO: 91) | QSADRTK (SEQ ID NO: 68) | QSSDLSR (SEQ ID NO: 15) | QRSTLKS (SEQ ID NO: 92) | RSAHLSR (SEQ ID NO: 26) | RSDDLTR (SEQ ID NO: 37) | N7a/N-KKR | C Ex 1 |
| SBS#61046 5'ctTTGCCTcG CTGGACTGgta tttgtgt (SEQ ID NO: 74) | RSDVLSE (SEQ ID NO: 19) | QSGHLSR (SEQ ID NO: 22) | LSQDLNR (SEQ ID NO: 93) | QSSDLSR (SEQ ID NO: 15) | RLYTLHK (SEQ ID NO: 90) | N/A | N6a/N-ELD | C Ex 1 |
| SBS#59192 5'ctTTGCCTcG CTGGACTGgta tttgtgt (SEQ ID NO: 74) | RSDTLSE (SEQ ID NO: 46) | QSGHLSR (SEQ ID NO: 22) | QSSDLSR (SEQ ID NO: 15) | QSSDLSR (SEQ ID NO: 15) | RLYTLHK (SEQ ID NO: 90) | N/A | N6a/N-ELD | C Ex 1 |
| SBS#59771 5'gtGCCCAGG GTGCTGGAG AAtccaaatg (SEQ ID NO: 76) | QSSNLAR (SEQ ID NO: 94) | QSGHLSR (SEQ ID NO: 22) | QSSDLSR (SEQ ID NO: 15) | TSGHLSR (SEQ ID NO: 21) | RSDNLSE (SEQ ID NO: 95) | ASKTRKN (SEQ ID NO: 96) | N7a/N-ELD | H Ex 2 |
| SBS#59245 5'agGACTTTG ACCATcAGAG GAcatttgg (SEQ ID NO: 77) | QSGHLAR (SEQ ID NO: 72) | QLTHLNS (SEQ ID NO: 97) | SKLYLNN (SEQ ID NO: 98) | DRSNLTR (SEQ ID NO: 99) | GTQGLGI (SEQ ID NO: 130) | DRSNLTR (SEQ ID NO: 99) | N7a/N-KKR | H Ex 2 |
| SBS#59244 5'gtGCCCAGG GTGCTGGAG AAtccaaatg (SEQ ID NO: 76) | QSSNLAR (SEQ ID NO: 94) | QSGHLSR (SEQ ID NO: 22) | QSSDLSR (SEQ ID NO: 15) | WHSSLHQ (SEQ ID NO: 16) | RSDNLSE (SEQ ID NO: 95) | ASKTRKN (SEQ ID NO: 96) | N7a/N-ELD | H Ex 2 |
| SBS#59790 5'agGACTTTG ACCATcAGAG GAcatttgg (SEQ ID NO: 77) | QSGHLAR (SEQ ID NO: 72) | QLTHLNS (SEQ ID NO: 97) | SKLYLNN (SEQ ID NO: 98) | DRSNLTR (SEQ ID NO: 99) | YRWLRNS (SEQ ID NO: 100) | DRSNLTR (SEQ ID NO: 99) | N7a/N-KKR | H Ex 2 |
| SBS#59316 5'aaAAAGACc TCTGAGGGA TCCtgggagc (SEQ ID NO: 78) | DSGGLSK (SEQ ID NO: 101) | QSGHLSR (SEQ ID NO: 22) | RSDNLAR (SEQ ID NO: 52) | WRGDRVK (SEQ ID NO: 102) | DRSNLSR (SEQ ID NO: 91) | QRQNLVN (SEQ ID NO: 103) | N7a/N-ELD | J |
| SBS#59317 5'ctTACCCAG AGGCAAAGgg ctcccagga (SEQ ID NO: 79) | RSDNLSV (SEQ ID NO: 104) | RSADLSR (SEQ ID NO: 105) | RSDNLAR (SEQ ID NO: 52) | QGQDRHK (SEQ ID NO: 106) | DNSNRIK (SEQ ID NO: 29) | N/A | N7a/N-KKR | J |
| SBS#61135 5'aaAAAGACc TCTGAGGGA TCCtgggagc (SEQ ID NO: 78) | DSGGLSK (SEQ ID NO: 101) | QSGHLSR (SEQ ID NO: 22) | RSDNLAR (SEQ ID NO: 52) | RSDNLAR (SEQ ID NO: 52) | DRSNLSR (SEQ ID NO: 91) | QRQNLVN (SEQ ID NO: 103) | N7a/N-ELD | J |
| SBS#61137 5'aaAAAGACc TCTGAGGGA TCCtgggagc (SEQ ID NO: 78) | DSSDRKK (SEQ ID NO: 43) | QSGHLSR (SEQ ID NO: 22) | RSDNLAR (SEQ ID NO: 52) | WRGDRVK (SEQ ID NO: 102) | DRSNLSR (SEQ ID NO: 91) | QRQNLVN (SEQ ID NO: 103) | N7a/N-ELD | J |
| Human TTR | | | | | | | | |
| SBS#60489 5'gcAGAGGA GGAGCAGAC gatgagaagcc (SEQ ID NO: 80) | DRSNLSR (SEQ ID NO: 91) | QSGDLTR (SEQ ID NO: 39) | QSGHLSR (SEQ ID NO: 22) | QSGHLAR (SEQ ID NO: 72) | QLTHLNS (SEQ ID NO: 97) | N/A | N7a/N-KKR | Ex 1 |
| SBS#60488 5'atTCTTGGC AGGATGGCttc tcatcgtc (SEQ ID NO: 81) | QYCCLTN (SEQ ID NO: 107) | TSGNLTR (SEQ ID NO: 36) | RSDNLST (SEQ ID NO: 108) | FHSCLSA (SEQ ID NO: 109) | RNSDRTK (SEQ ID NO: 110) | N/A | N7a/N-ELD | Ex 1 |

TABLE 11-continued

TTR-Specific ZFN designs

| SBS #/Target | F1 | F2 | F3 | F4 | F5 | F6 | Linker/Fok | region |
|---|---|---|---|---|---|---|---|---|
| SBS#57730 5'gaGGAGGA GCAGACGAT GAGaagccatc (SEQ ID NO: 82) | RSANLAR (SEQ ID NO: 111) | TSGNLTR (SEQ ID NO: 36) | DRSNLSR (SEQ ID NO: 91) | QSGDLTR (SEQ ID NO: 39) | QSGHLAR (SEQ ID NO: 72) | DRSHLAR (SEQ ID NO: 112) | L0/ N-ELD | Ex 1 |
| SBS#57731 5'ccTTGCTGG ACTGGTATTT Gtgtctgag (SEQ ID NO: 83) | RPYTLRL (SEQ ID NO: 113) | HRSNLNK (SEQ ID NO: 114) | VSNNLAC (SEQ ID NO: 115) | DRSNLTR (SEQ ID NO: 99) | RSDVLSE (SEQ ID NO: 19) | RNFSLTM (SEQ ID NO: 116) | L0/ C-KKR | Ex 1 |
| SBS#60602 5'caCATGCAc GGCCACATT GATggcagga (SEQ ID NO: 84) | TSGNLTR (SEQ ID NO: 36) | HKSARAA (SEQ ID NO: 117) | YDYGRYT (SEQ ID NO: 118) | DRSHLAR (SEQ ID NO: 112) | QSGDLTR (SEQ ID NO: 39) | TSHNRNA (SEQ ID NO: 119) | N7a/ N-KKR | Ex 2 |
| SBS#60601 5'taGATGCTgT CCGAGGCAgt cctgccat (SEQ ID NO: 85) | QSGDLTR (SEQ ID NO: 39) | RSDNLAR (SEQ ID NO: 52) | DSSDRKK (SEQ ID NO: 43) | QSSDLSR (SEQ ID NO: 15) | TSGNLTR (SEQ ID NO: 36) | N/A | N7a/ N-ELD | Ex 2 |
| SBS#60751 5'tgCATGCTC ATGGAATGG GGagatgcca (SEQ ID NO: 86) | RSAHLSR (SEQ ID NO: 26) | RSDALTQ (SEQ ID NO: 120) | QSGHLAR (SEQ ID NO: 72) | IRSNLLA (SEQ ID NO: 121) | QSSDLSR (SEQ ID NO: 15) | LRHNLRA (SEQ ID NO: 122) | N6a/ N-KKR | Ex 3 |
| SBS#60750 5'ctTACTGGA AGGCACTTgg catctcccc (SEQ ID NO: 87) | ARSTRIT (SEQ ID NO: 123) | QSGSLTR (SEQ ID NO: 67) | RSDNLSV (SEQ ID NO: 104) | RNAHRIN (SEQ ID NO: 124) | DNSNRIK (SEQ ID NO: 29) | N/A | N6a/ ELD | Ex 3 |
| SBS#60764 5'gcTCATGGA ATGGGGAGA TGccaagtgc (SEQ ID NO: 88) | RSDSLSV (SEQ ID NO: 125) | RSANLTR (SEQ ID NO: 57) | RSDHLSR (SEQ ID NO: 27) | TSSNRKT (SEQ ID NO: 126) | RSDHLSQ (SEQ ID NO: 41) | QSADRTK (SEQ ID NO: 68) | L0/ N-ELD | Ex 3 |
| SBS#60765 5'gcAGAGGTG AGTATACAG ACcttcgagg (SEQ ID NO: 89) | DRSNLSR (SEQ ID NO: 91) | QKVTLAA (SEQ ID NO: 127) | TSSNRKT (SEQ ID NO: 126) | RSDDLSR (SEQ ID NO: 128) | LRHHLTR (SEQ ID NO: 17) | QSAHLKA (SEQ ID NO: 129) | L0/ C-KKR | Ex 3 |
| SBS# 60502 5'ctGCCTTGC TGGACTGGtatt tgtgtct (SEQ ID NO: 220) | VSNNLAC (SEQ ID NO: 115) | DRSNLTR (SEQ ID NO: 99) | RSDVLSE (SEQ ID NO: 19) | RNFSLTM (SEQ ID NO: 116) | HRKSLSR (SEQ ID NO: 223) | N/A | L8c4/ KKR | Ex 1 |
| SBS# 64066 5'gaGCAGACG ATGAGAAGcc atcctgcca (SEQ ID NO: 221) | AHGARWN (SEQ ID NO: 224) | RSANLTR (SEQ ID NO: 57) | TSGNLTR (SEQ ID NO: 36) | DRSNLSR (SEQ ID NO: 91) | QSGDLTR (SEQ ID NO: 39) | N/A | L8c4/ ELD | Ex 1 |
| SBS# 67451 5'gaGCAGACG ATGAGAAGcc atcctgcca (SEQ ID NO: 221) | AHGARWN (SEQ ID NO: 224) | RSANLTR (SEQ ID NO: 57) | TSANLSR (SEQ ID NO: 199) | DRSNLSR (SEQ ID NO: 91) | QSSDLTR (SEQ ID NO: 184) | N/A | L8c4/ ELD | Ex 1 |
| SBS# 67458 5'ctGCCTTGC TGGACTGGtatt tgtgtct (SEQ ID NO: 220) | VSNNLAC (SEQ ID NO: 115) | DRSNLTR (SEQ ID NO: 99) | RSDTLSE (SEQ ID NO: 46) | RRWSLSV (SEQ ID NO: 225) | DRSTRTK (SEQ ID NO: 156) | N/A | L8c4/ KKR | Ex 1 |
| SBS# 60501 5'gaGCAGACG ATGAGAAGcc atcctgcca (SEQ ID NO: 221) | AHGARWN (SEQ ID NO: 224) | RSANLTR (SEQ ID NO: 57) | TSGNLTR (SEQ ID NO: 36) | DRSNLTR (SEQ ID NO: 99) | QSGDLTR (SEQ ID NO: 39) | N/A | L8c4/ ELD | Ex 1 |

TABLE 11-continued

TTR-Specific ZFN designs

| SBS #/Target | F1 | F2 | F3 | F4 | F5 | F6 | Linker/Fok | region |
|---|---|---|---|---|---|---|---|---|
| SBS# 64080 5'ctGCCTTGC TGGACTGGtatt tgtgtct (SEQ ID NO: 220) | VSNNLAC (SEQ ID NO: 115) | DRSNLTR (SEQ ID NO: 99) | RSDVLSE (SEQ ID NO: 19) | RNFSLTM (SEQ ID NO: 116) | DRSTRTK (SEQ ID NO: 156) | N/A | L8c4/ KKR | Ex 1 |
| SBS# 67495 5'tgCATGCTC ATGGAATGG GGagatgcca (SEQ ID NO: 86) | RSDHLST (SEQ ID NO: 69) | RSDARTN (SEQ ID NO: 226) | QSGHLAR (SEQ ID NO: 72) | IRSNLLA (SEQ ID NO: 121) | QSSDLSR (SEQ ID NO: 15) | LKWNLRT (SEQ ID NO: 227) | N6a*/ KKR | Ex 3 |
| SBS# 60750 5'ctTACTGGA AGGCACTTgg catctcccc (SEQ ID NO: 87) | ARSTRIT (SEQ ID NO: 123) | QSGSLTR (SEQ ID NO: 67) | RSDNLSV (SEQ ID NO: 104) | RNAHRIN (SEQ ID NO: 124) | DNSNRIK (SEQ ID NO: 29) | N/A | N6a*/ ELD | Ex 3 |
| SBS# 67493 5'tgCATGCTC ATGGAATGG GGagatgcca (SEQ ID NO: 86) | RSDHLST (SEQ ID NO: 69) | RSDARTN (SEQ ID NO: 226) | QSGHLAR (SEQ ID NO: 72) | IRSNLLA (SEQ ID NO: 121) | QSSDLSR (SEQ ID NO: 15) | LRHNLRA (SEQ ID NO: 122) | N6a*/ KKR | Ex 3 |
| SBS# 64347 5'tcTTACTGgA AGGCACTTgg catctccc (SEQ ID NO: 222) | YTYSLSE (SEQ ID NO: 228) | QSGDLTR (SEQ ID NO: 39) | RKDQLVA (SEQ ID NO: 229) | RSDVLSE (SEQ ID NO: 19) | QRTPRAK (SEQ ID NO: 230) | N/A | N6a*/ ELD | Ex 3 |
| SBS# 60751 5'tgCATGCTC ATGGAATGG GGagatgcca (SEQ ID NO: 86) | RSAHLSR (SEQ ID NO: 26) | RSDALTQ (SEQ ID NO: 231) | QSGHLAR (SEQ ID NO: 72) | IRSNLLA (SEQ ID NO: 121) | QSSDLSR (SEQ ID NO: 15) | LRHNLRA (SEQ ID NO: 122) | N6a*/ KKR | Ex 3 |
| SBS# 67489 5'tcTTACTGgA AGGCACTTgg catctccc (SEQ ID NO: 222) | YTYSLSE (SEQ ID NO: 228) | QSGDLTR (SEQ ID NO: 39) | RKDQLVA (SEQ ID NO: 229) | RSDVLSE (SEQ ID NO: 19) | QRTPRAK (SEQ ID NO: 230) | N/A | N6a*/ ELD | Ex 3 |

Figure 5B:
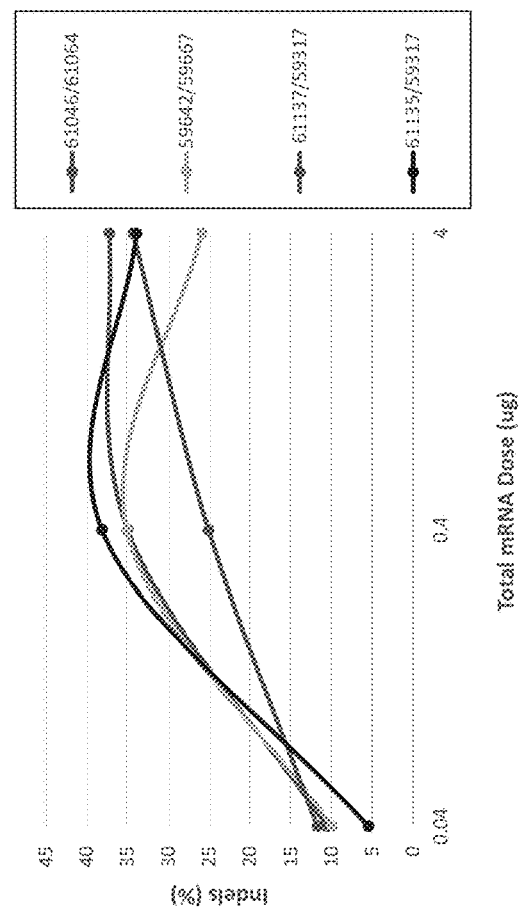
FIGS. 5A and 5B are graphs depicting the percent gene modification ("indels" indicating insertions and/or deletions characteristic of NHEJ following nuclease-mediated cleavage) in mouse hepatocytes treated with the indicated gene modulators (see Table 11).
Figure 5A:
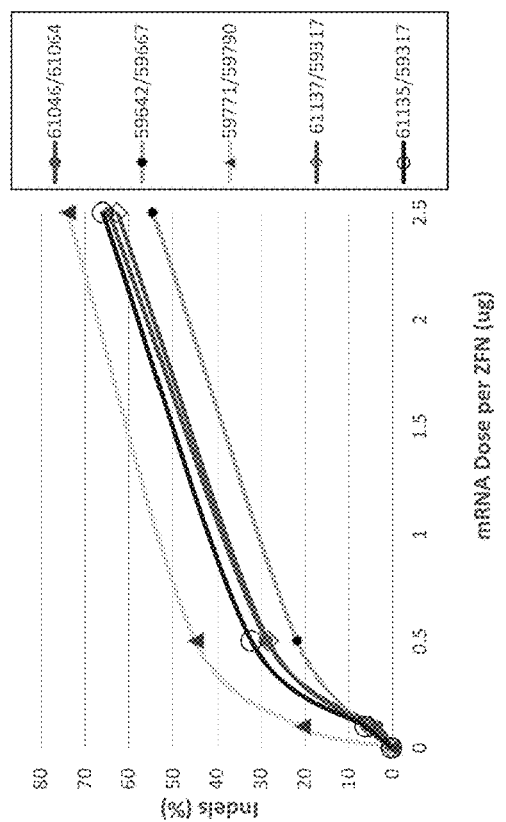
Figure 6B:
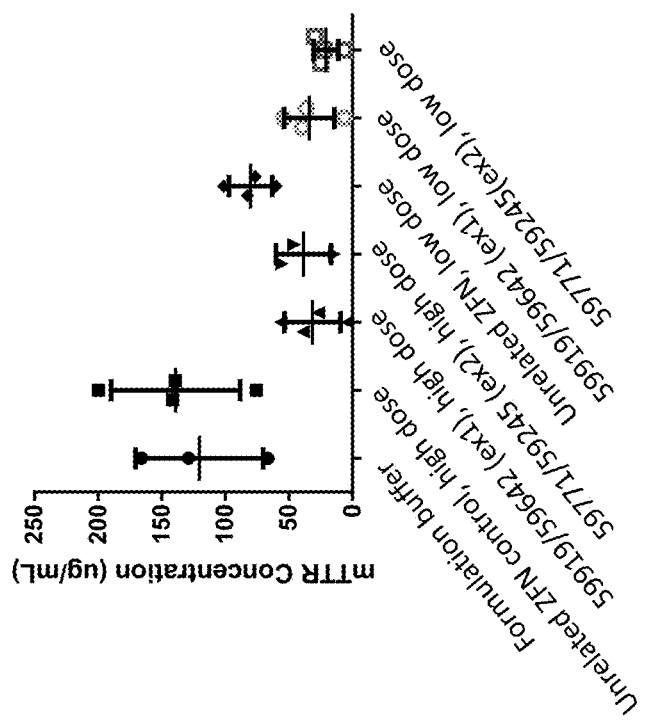
FIGS. 6A and 6B are graphs depicting the activity of TTR ZFNs in mice.
Figure 6A:
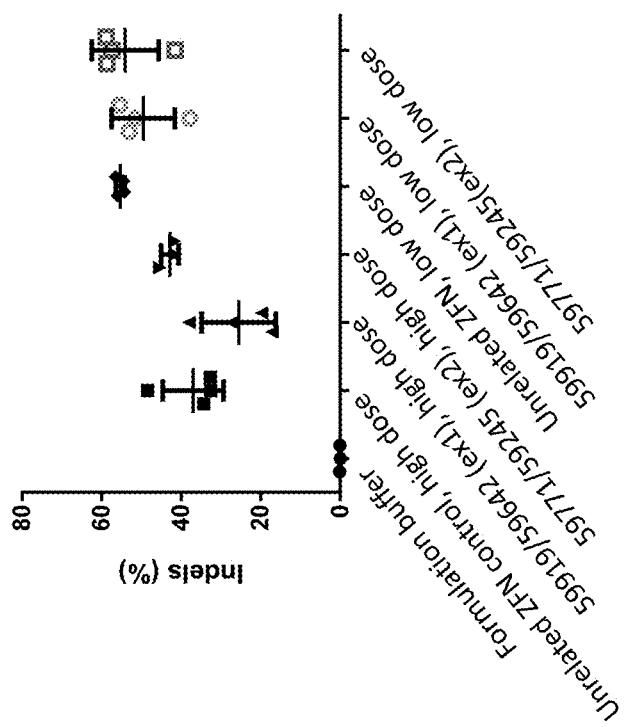
Figure 7:
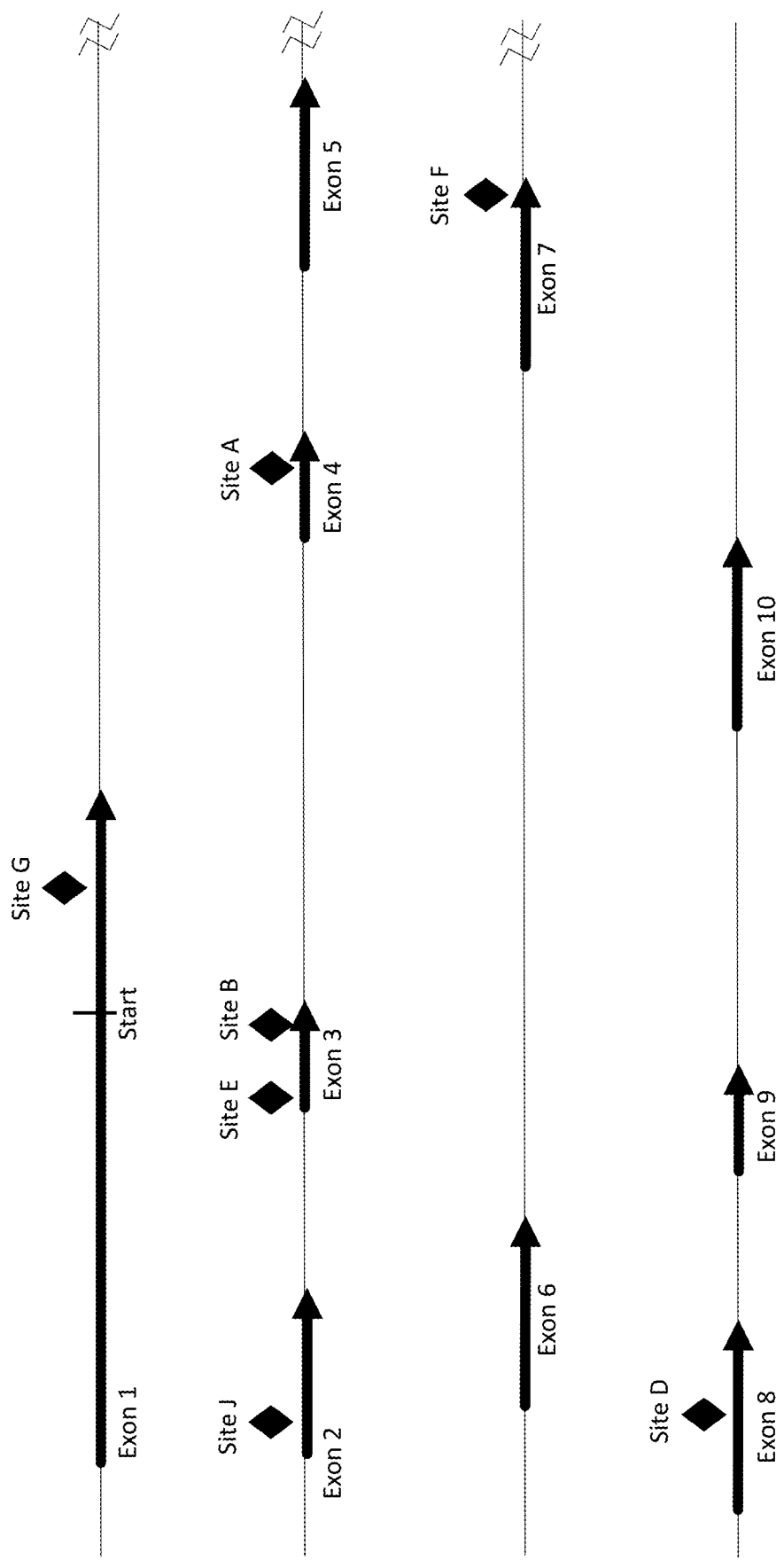
FIG. 7 is a schematic of the mouse PCSK9 gene, showing the exons and the sites selected to target.

All murine specific nucleases were tested in B16-F10 cells (FIG. 5A), primary mouse hepatocytes (FIG. 5B), or Hepa1-6 cells (FIGS. 8A and 8B) and found to be active. Lead ZFNs targeting mTTR exon 1, Site C (59919/59642) and exon 2, Site H (59771/59245), were cloned into individual AAV expression cassette vectors containing a human ApoE enhancer and human SERPINA1 promoter and then packaged into serotype AAV8. AAV ZFNs were then injected intravenously into wildtype C57BL6 mice at a high dose (1.5e11 vg per ZFN per mouse) or a low dose (2.5e10 vg per ZFN per mouse) and livers were harvested for gene modification and plasma was analyzed for mTTR protein knockdown 28 days later. FIG. 6A shows robust editing within the liver, while FIG. 6B shows high levels of circulating mTTR protein knockdown which is specific to the mTTR-targeted ZFN AAV vectors All human specific ZFNs were tested in the human liver cell line HepG2 and found to be active (see Table 12 below for activity of exemplary pairs). In brief, total ZFN mRNA dose, where half of the dose is each individual ZFN, is shown in Table 12 and was as added in a 100 μL transfection volume. All proteins bound to their targets and induced cleavage. Exemplary activity (% indel) results of pairwise combinations of ZFNs which bind exon 1 and exon 3 of the gene. % Indels were measured by deep sequencing (MiSeq, Illumnia) and then analyzed for the percent of alleles comprising insertions and/or deletions at the cleavage site.

TABLE 12

Activity of Human TTR reagents

| | mRNA Dose (ug/mL) | | |
|---|---|---|---|
| Sample | 5 | 40 | Exon |
| 64066/60502 | 19.0 | 37.3 | 1 |
| 67451/60502 | 17.9 | 36.6 | 1 |
| 67458/60501 | 27.4 | 47.6 | 1 |
| 64080/60501 | 24.2 | 47.0 | 1 |
| 67495/60750 | 30.0 | 61.8 | 3 |
| 67493/60750 | 24.8 | 59.2 | 3 |
| 64347/60751 | 25.7 | 63.5 | 3 |
| 67489/60751 | 19.3 | 62.2 | 3 |

To determine the specificity of the ZFNs which bind the murine TTR gene (mTTR), ZFN pairs were subjected to unbiased identification of candidate off-target sites using methods similar to those previously described (Tsai et al (2015) *Nat Biotechnol* 33:187-197) in B16-F10 cells. Briefly, B16-F10 cells were electroporated with mRNA encoding the ZFNs as well as barcoded ssDNA oligos using the BTX electroporation device to allow for unbiased identification of sites which have undergone double-stranded DNA cleavage and NHEJ-mediated integration of the ssDNA oligos. The top 24 sites found identified by Miseq next-generation sequencing (NGS) to contain integrated oligos were then confirmed in primary mouse hepatocyte cells which were transduced with the ZFN mRNA via lipofection (FIG. 5B). Genomic DNA from ZFN-treated mouse hepatocytes was amplified by PCR generating amplicons of approximately 200 bp surrounding the potential ZFN binding site. In order to build an equimolar library, PCR products were quantified with KAPA Library Quantification Kit for Illumina sequencing platforms (KAPABIOSYSTEMS) on C1000 Thermal Cycler (BIO-RAD) and sequenced on MiSeq Illumina Platform using MiSeq Reagent v.3 (Illumina). Quantification of insertions and deletions and insertions (indels) was then performed. Briefly, raw paired-end reads were joined and aligned to the specific genomic target sequences. Sequences with indels of ≥1 bp located within a 40 bp region encompassing the ZFN target site were considered as nuclease-induced genome modifications. All sites that produced a Bonferroni p-value ≤0.05 in comparison to a GFP-encoding mRNA electroporated control, were deemed off-target sites.

Modifications to residues within the ZFP which undergo non-specific binding to genomic DNA, in both the zinc finger backbone and in the FokI domain, were mutated in several ZFNs (R to Q changes at 1 to 6 residues) as well as mutations to the FokI which either affect catalytic activity or potentially non-specific DNA binding (U.S. Patent Publication No. 20180087072). The mutations made are shown below in Table 13 below.

TABLE 13

Backbone/FokI variants of SBS#59771/SBS#59790

| SBS # (target site, 5'-3') | Design [Helix Sequence, SEQ ID] [Mutations to finger backbone] | | | | | | Linker Fok mutants |
|---|---|---|---|---|---|---|---|
| | F1 | F2 | F3 | F4 | F5 | F6 | |
| 59771 5'gtGCCCAGGG TGCTGGAGAAt ccaaatg (SEQ ID NO: 76) | QSSNLAR (SEQ ID NO: 94) none | QSGHLSR (SEQ ID NO: 22) none | QSSDLSR (SEQ ID NO: 15) none | TSGHLSR (SEQ ID NO: 21) none | RSDNLSE (SEQ ID NO: 95) none | ASKTRKN (SEQ ID NO: 96) none | N7a ELD |
| 69063 5'gtGCCCAGGG TGCTGGAGAAt ccaaatg (SEQ ID NO: 76) | QSSNLAR (SEQ ID NO: 94) Qm5 | QSGHLSR (SEQ ID NO: 22) none | QSSDLSR (SEQ ID NO: 15) Qm5 | TSGHLSR (SEQ ID NO: 21) none | RSDNLSE (SEQ ID NO: 95) Qm5 | ASKTRKN (SEQ ID NO: 96) Qm5 | N7a ELD G480S |
| 69052 5'gtGCCCAGGG TGCTGGAGAAt ccaaatg (SEQ ID NO: 76) | QSSNLAR (SEQ ID NO: 94) none | QSGHLSR (SEQ ID NO: 22) Qm5 | QSSDLSR (SEQ ID NO: 15) none | TSGHLSR (SEQ ID NO: 21) Qm5 | RSDNLSE (SEQ ID NO: 95) none | ASKTRKN (SEQ ID NO: 96) Qm5 | N7a ELD D421S |
| 69121 5'gtGCCCAGGG TGCTGGAGAAt ccaaatg (SEQ ID NO: 76) | QSSNLAR (SEQ ID NO: 94) none | QSGHLSR (SEQ ID NO: 22) none | QSSDLSR (SEQ ID NO: 15) none | TSGHLSR (SEQ ID NO: 21) none | RSDNLSE (SEQ ID NO: 95) none | ASKTRKN (SEQ ID NO: 96) none | N7a ELD D421S, Q531R |
| 59790 5'agGACTTTGA CCATcAGAGG Acatttgg (SEQ ID NO: 77) | QSGHLAR (SEQ ID NO: 72) none | QLTHLNS (SEQ ID NO: 97) none | SKLYLNN (SEQ ID NO: 98) none | DRSNLTR (SEQ ID NO: 99) none | YRWLRNS (SEQ ID NO: 100) none | DRSNLTR (SEQ ID NO: 99) none | N7a KKR |
| 69110 5'agGACTTTGA CCATcAGAGG Acatttgg (SEQ ID NO: 77) | QSGHLAR (SEQ ID NO: 72) Qm5 | QLTHLNS (SEQ ID NO: 97) none | SKLYLNN (SEQ ID NO: 98) Qm5 | DRSNLTR (SEQ ID NO: 99) Qm5 | YRWLRNS (SEQ ID NO: 100) Qm5 | DRSNLTR (SEQ ID NO: 99) Qm5 | N7a KKR S418P |
| 69107 5'agGACTTTGA CCATcAGAGG Acatttgg (SEQ ID NO: 77) | QSGHLAR (SEQ ID NO: 72) Qm5 | QLTHLNS (SEQ ID NO: 97) none | SKLYLNN (SEQ ID NO: 98) Qm5 | DRSNLTR (SEQ ID NO: 99) Qm5 | YRWLRNS (SEQ ID NO: 100) Qm5 | DRSNLTR (SEQ ID NO: 99) Qm5 | N7a KKR K387S |
| 69102 5'agGACTTTGA CCATcAGAGG Acatttgg (SEQ ID NO: 77) | QSGHLAR (SEQ ID NO: 72) none | QLTHLNS (SEQ ID NO: 97) Qm5 | SKLYLNN (SEQ ID NO: 98) none | DRSNLTR (SEQ ID NO: 99) Qm5 | YRWLRNS (SEQ ID NO: 100) none | DRSNLTR (SEQ ID NO: 99) Qm5 | N7a KKR S418P |

TABLE 13-continued

Backbone/FokI variants of SBS#59771/SBS#59790

| SBS # (target site, 5'-3') | Design [Helix Sequence, SEQ ID] [Mutations to finger backbone] | | | | | | Linker Fok mutants |
|---|---|---|---|---|---|---|---|
| | F1 | F2 | F3 | F4 | F5 | F6 | |
| 69128 5'agGACTTTGA CCATcAGAGG Acatttgg (SEQ ID NO: 77) | QSGHLAR (SEQ ID NO: 72) none | QLTHLNS (SEQ ID NO: 97) none | SKLYLNN (SEQ ID NO: 98) none | DRSNLTR (SEQ ID NO: 99) none | YRWLRNS (SEQ ID NO: 100) none | DRSNLTR (SEQ ID NO: 99) none | N7a KKR D421S, Q481H |

Figure 8A:
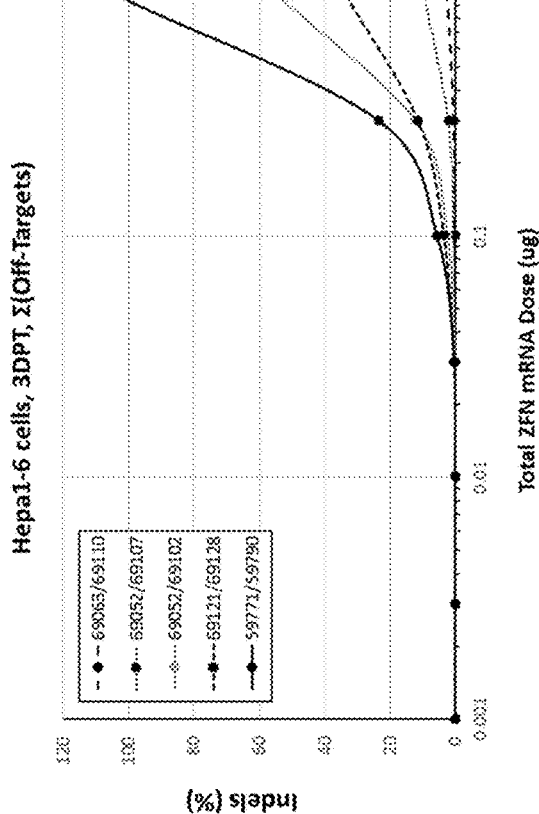
FIGS. 8A and 8B are graphs depicting cleavage of the murine TTR targets by ZFN. The ZFNs tested in this analysis comprise mutations in their backbones and in the FokI cleavage domain to remove specific phosphate contacting residues that may be related to off-target cleavage.
Figure 8B:
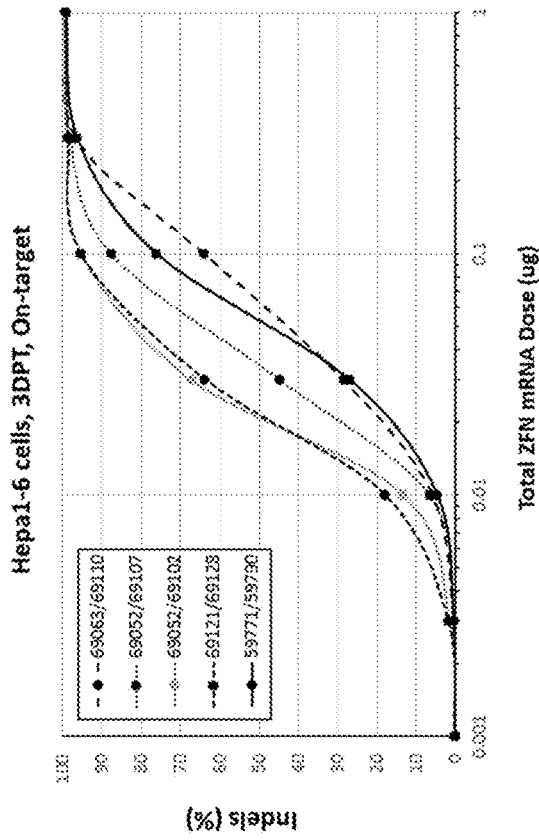

These variants were then tested for on target and off target cleavage activity. FIG. 8A shows the on-target activity in Hepa1-6 cells of the lead mutant ZFNs originating from the 59771/59790 pair. FIG. 8B shows the indel sum of the top 3 identified off-target sites for these lead ZFNs, demonstrating a decrease in off-target cleavage for the mutant ZFNs.

IV. Nuclease Targeting of HAO1

HAO1-specific zinc finger proteins were made to target *Macaca mulatta* HAO1 as described above. Exemplary proteins are shown below in Table 14.

Activity was analyzed as described above, and is shown below in Table 15. Total ZFN mRNA dose means that half of the dose is each individual ZFN, and was as added in a 100 μL transfection volume. All proteins bound to their targets and induced cleavage. Exemplary activity (% indel) results of pairwise combinations of ZFNs which bind exon 4 of the gene. % Indels were measured by deep sequencing (MiSeq, Illumnia) and then analyzed for the percent of alleles comprising insertions and/or deletions at the cleavage site.

TABLE 14

HAO1 ZFN designs for *M. mulatta*

| SBS #/Target | F1 | F2 | F3 | F4 | F5 | F6 | Linker/ Fok |
|---|---|---|---|---|---|---|---|
| SBS# 66075 5'acTTGCTGC ATATGtGGCT AAagcaata (SEQ ID NO: 232) | QLGNLHT (SEQ ID NO: 234) | DRSHLAR (SEQ ID NO: 112) | RSDVLST (SEQ ID NO: 235) | ASGNLLN (SEQ ID NO: 236) | RSDVLSE (SEQ ID NO: 19) | RKYSLRV (SEQ ID NO: 195) | N6a* ELD |
| SBS# 66079 5'acTTGCTGC ATATGtGGCT AAagcaata (SEQ ID NO: 232) | QLGNLHT (SEQ ID NO: 234) | DRSHLAR (SEQ ID NO: 112) | RSDVLST (SEQ ID NO: 235) | ASGNLLN (SEQ ID NO: 236) | RSDTLSE (SEQ ID NO: 46) | RRWSLSV (SEQ ID NO: 225) | N6a* ELD |
| SBS# 64555 5'tcCCAGCTG ATAGATGGG TCtattgctt (SEQ ID NO: 233) | DRSALAR (SEQ ID NO: 34) | RKYYLAK (SEQ ID NO: 237) | QSAHLVC (SEQ ID NO: 238) | TSGNLTR (SEQ ID NO: 36) | QSSDLSR (SEQ ID NO: 15) | QRSTLKS (SEQ ID NO: 92) | N6a* KKR |
| SBS# 66083 5'tcCCAGCTG ATAGATGGG TCtattgctt (SEQ ID NO: 233) | DRSALAR (SEQ ID NO: 34) | RKYYLAK (SEQ ID NO: 237) | QSAHLVC (SEQ ID NO: 238) | TSGNLTR (SEQ ID NO: 36) | QSSDLSR (SEQ ID NO: 15) | QRSTLKS (SEQ ID NO: 92) | N7a* KKR |
| SBS# 66084 5'tcCCAGCTG ATAGATGGG TCtattgctt (SEQ ID NO: 233) | DRSALAR (SEQ ID NO: 34) | RKYYLAK (SEQ ID NO: 237) | QSAHLVC (SEQ ID NO: 238) | TSGNLTR (SEQ ID NO: 36) | QSSDLSR (SEQ ID NO: 15) | QRSTLKS (SEQ ID NO: 92) | N6a* KKR |
| SBS# 64552 5'acTTGCTGC ATATGtGGCT AAagcaata (SEQ ID NO: 232) | QLGNLHT (SEQ ID NO: 234) | DRSHLAR (SEQ ID NO: 112) | RSDVLST (SEQ ID NO: 235) | ASGNLLN (SEQ ID NO: 236) | RSDVLSE (SEQ ID NO: 19) | RNFSLTM (SEQ ID NO: 116) | N6a* ELD |

TABLE 15

Activity of *M. mulatta* HAO1 ZFNs

| Sample (mRNA Dose (ug/mL)) | % Indels | |
|---|---|---|
| | 5 | 20 |
| 66075/64555 | 86.9 | 74.8 |
| 66079/64555 | 84.2 | 75.7 |
| 66083/64552 | 80.6 | 76.9 |
| 66084/64552 | 80.6 | 78.2 |

V. Nuclease Targeting of KLKB1

KLKB1-specific zinc finger proteins were made to target murine KLKB1 as described above, shown below in Table 16. Several exons in the KLKB1 gene were selected for targeting in mouse liver cell line Hepa1-6.

TABLE 16

Design of murine KLKB1 ZFNs

| SBS #/Target | F1 | F2 | F3 | F4 | F5 | F6 | Linker/Fok | Exon |
|---|---|---|---|---|---|---|---|---|
| SBS# 63342 5'ctGCTCCTT GCACGAAGG TCacattcag (SEQ ID NO: 239) | DRSALSR (SEQ ID NO: 251) | RLDNRTA (SEQ ID NO: 73) | RSDTLSE (SEQ ID NO: 46) | QKRNRTK (SEQ ID NO: 151) | IRSTLRD (SEQ ID NO: 252) | HRSSLRR (SEQ ID NO: 253) | N7a* KKR | Ex 9 |
| SBS# 63341 5'ttGACTTTGA AGGGGAAGA Actgaatgt (SEQ ID NO: 240) | QSANRTK (SEQ ID NO: 192) | QSGNLAR (SEQ ID NO: 14) | RSDHLSE (SEQ ID NO: 30) | QSGNLAR (SEQ ID NO: 14) | GTQGLGI (SEQ ID NO: 130) | DRSNLTR (SEQ ID NO: 99) | N7a* ELD | Ex 9 |
| SBS# 63238 5'gcAGAGTGC TGGAAAATatc catggggc (SEQ ID NO: 241) | TSSNRKT (SEQ ID NO: 126) | QSGHLSR (SEQ ID NO: 22) | RSDVLSE (SEQ ID NO: 19) | RLYTLHK (SEQ ID NO: 254) | QNAHRKT (SEQ ID NO: 182) | N/A | N7a* KKR | Ex 7 |
| SBS# 63236 5'ccGCTGAGtT CACAGGTTG CCccatgga (SEQ ID NO: 242) | ERGTLAR (SEQ ID NO: 160) | TSGSLTR (SEQ ID NO: 185) | RSDNLSQ (SEQ ID NO: 208) | ASNDRKK (SEQ ID NO: 209) | RSANLAR (SEQ ID NO: 111) | QSSDLRR (SEQ ID NO: 71) | N7a* ELD | Ex 7 |
| SBS# 63195 5'ttGTCGGTCT TAGAGATATT aaagttgg (SEQ ID NO: 243) | YSWTLRD (SEQ ID NO: 255) | TSGNLTR (SEQ ID NO: 36) | QNAHRKT (SEQ ID NO: 182) | STAALSY (SEQ ID NO: 256) | TSGHLSR (SEQ ID NO: 21) | DRSALAR (SEQ ID NO: 34) | N7a* KKR | Ex 5 |
| SBS# 63194 5'aaGGACTTG ATATGaGAGG GTccaactt (SEQ ID NO: 244) | TSGHLSR (SEQ ID NO: 21) | RSDNLTR (SEQ ID NO: 40) | RSDTLSQ (SEQ ID NO: 257) | ASANRTK (SEQ ID NO: 258) | YTYSLSE (SEQ ID NO: 228) | QSGHLSR (SEQ ID NO: 22) | N7a* ELD | Ex 5 |
| SBS# 63411 5'ttCACTTGCA GGCTGACctgc catggcc (SEQ ID NO: 245) | DRSNLSR (SEQ ID NO: 91) | LRQDLKR (SEQ ID NO: 259) | RSDNLST (SEQ ID NO: 108) | RQWSLRI (SEQ ID NO: 260) | DRSNRTT (SEQ ID NO: 261) | N/A | N6a* KKR | Ex 11 |
| SBS# 63410 5'tcTTTAGGG GAGTGGCCatg gcaggtca (SEQ ID NO: 246) | DRSTRTK (SEQ ID NO: 156) | RSDSLLR (SEQ ID NO: 262) | QRCHLTK (SEQ ID NO: 263) | RSDHLSQ (SEQ ID NO: 41) | STAALSY (SEQ ID NO: 256) | N/A | N6a* ELD | Ex 11 |
| SBS# 63375 5'tgCATGCCA TAGGTGATCC Tagttgggg (SEQ ID NO: 247) | HNHDLRN (SEQ ID NO: 264) | TSGNLTR (SEQ ID NO: 36) | LRHHLTR (SEQ ID NO: 17) | QKWPRDS (SEQ ID NO: 265) | DRSDLSR (SEQ ID NO: 154) | LRFNLRN (SEQ ID NO: 266) | N7a* KKR | Ex 10 |
| SBS# 63374 5'ggGAGCCAT CTGTGGATA ACcttaagga (SEQ ID NO: 248) | DRSNRTT (SEQ ID NO: 261) | TNSNRKR (SEQ ID NO: 267) | RSDSLLR (SEQ ID NO: 262) | LKQDRRK (SEQ ID NO: 268) | EKHDLHR (SEQ ID NO: 269) | RSANLTR (SEQ ID NO: 57) | L0 ELD | Ex 10 |

TABLE 16-continued

Design of murine KLKB1 ZFNs

| SBS #/Target | F1 | F2 | F3 | F4 | F5 | F6 | Linker/Fok | Exon |
|---|---|---|---|---|---|---|---|---|
| SBS# 63107 5'acGGCGAGA AAGCTGAAca gcaggcacc (SEQ ID NO: 249) | QSGNLAR (SEQ ID NO: 14) | QSSDLSR (SEQ ID NO: 15) | QSGNRTT (SEQ ID NO: 270) | RSANLAR (SEQ ID NO: 111) | DRSHLAR (SEQ ID NO: 112) | N/A | N7a* KKR | Ex 3 |
| SBS# 63106 5'ggCACCTGg GGTGAAaAGT GCAcatctt (SEQ ID NO: 250) | QSGDLTR (SEQ ID NO: 39) | LRHQLKS (SEQ ID NO: 271) | QRSNLVR (SEQ ID NO: 272) | TSGHLSR (SEQ ID NO: 21) | RSDVLST (SEQ ID NO: 235) | DTRNLRA (SEQ ID NO: 273) | L0 ELD | Ex 3 |

All nucleases shown bound to their target sites and were active. Table 17 below shows the activity of the indicated pairs, indicating the individual ZFN mRNA dose, where each ZFN mRNA was used in a 1:1 mass ratio that was as added in a 100 µL transfection volume. All proteins bound to their targets and induced cleavage. Exemplary activity (% indel) results of pairwise combinations of ZFNs which bind various coding regions of the gene. % Indels were measured by deep sequencing (MiSeq, Illumnia) and then analyzed for the percent of alleles comprising insertions and/or deletions at the cleavage site.

TABLE 17

Activity of murine KLKB1 ZFN Activity (% Indels)

| | | mRNA per ZFN (ug/mL) | |
|---|---|---|---|
| Locus | Sample | 5 | 40 |
| Exon 9 | 63342/63341 | 64.6129 | 96.7541 |
| Exon 7 | 63238/63236 | 45.2949 | 92.497 |
| Exon 5 | 63195/63194 | 17.8121 | 89.8445 |
| Exon 11 | 63411/63410 | 15.8158 | 84.6924 |
| Exon 10 | 63375/63374 | 11.8068 | 93.6912 |

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An isolated liver cell in which expression of an endogenous PCSK9 gene is altered as compared to wild-type, wherein the liver cell comprises a zinc finger protein comprising 5 or 6 zinc finger domains, each zinc finger domain comprising a recognition helix region sequence ordered F1 to F5 or F1 to F6, wherein the zinc finger protein comprises recognition helix regions ordered as shown in a single row of the following Table:

| F1 | F2 | F3 |
|---|---|---|
| QSSHLTR (SEQ ID NO:13) | QSGNLAR (SEQ ID NO:14) | QS SDLSR (SEQ ID NO:15) |
| RSDVLSE (SEQ ID NO:19) | TRNGLKY (SEQ ID NO:20) | TSGHLSR (SEQ ID NO:21) |
| QSGALAR (SEQ ID NO:25) | RSDVLSE (SEQ ID NO:19) | RSAHLSR (SEQ ID NO:26) |
| RSDHLSR (SEQ ID NO:27) | QSGHLSR (SEQ ID NO:22) | HKQHRDA (SEQ ID NO:18) |
| RSDHLSR (SEQ ID NO:27) | QQWDRKQ (SEQ ID NO:32) | TPSYLPT (SEQ ID NO:33) |
| QSGNLAR (SEQ ID NO:14) | TSGNLTR (SEQ ID NO:36) | RSDDLTR (SEQ ID NO:37) |
| QSGDLTR (SEQ ID NO:39) | RSDNLTR (SEQ ID NO:40) | QSGALAR (SEQ ID NO:25) |
| RSAHLSR (SEQ ID NO:26) | DSSDRKK (SEQ ID NO:43) | QHQVLVR (SEQ ID NO:44) |
| DGYYLPT (SEQ ID NO:48) | DRSALAR (SEQ ID NO:34) | ERQTLIK (SEQ ID NO:49) |
| RSDNLAR (SEQ ID NO:52) | DRSVLHR (SEQ ID NO:53) | RSDTLSA (SEQ ID NO:54) |
| RSDVLSE (SEQ ID NO:19) | QKCCLRS (SEQ ID NO:58) | DRSHLTR (SEQ ID NO:59) |
| HRQRLEE (SEQ ID NO:62) | RNASRTR (SEQ ID NO:63) | DRSHLTR (SEQ ID NO:59) |

| F4 | F5 | F6 |
|---|---|---|
| WHSSLHQ (SEQ ID NO:16) | LRHHLTR (SEQ ID NO:17) | HKQHRDA (SEQ ID NO:18) |
| QSGHLSR (SEQ ID NO:22) | NNRDLIN (SEQ ID NO:23) | TSSNLSR (SEQ ID NO:24) |
| RSDHLSR (SEQ ID NO:27) | DRSVLAR (SEQ ID NO:28) | N/A |
| DNSNRIK (SEQ ID NO:29) | RSDHLSE (SEQ ID NO:30) | HSRTRTK (SEQ ID NO:31) |
| DRSALAR (SEQ ID NO:34) | RSDHLSE (SEQ ID NO:30) | RKDARIT (SEQ ID NO:35) |
| RSDHLSE (SEQ ID NO:30) | DKSNRKK (SEQ ID NO:38) | N/A |
| QSGHLSR (SEQ ID NO:22) | RSDHLSQ (SEQ ID NO:41) | DSSHRTR (SEQ ID NO:42) |
| QNATRTK (SEQ ID NO:45) | RSDTLSE (SEQ ID NO:46) | RSPGRMG (SEQ ID NO:47) |
| QSGHLSR (SEQ ID NO:22) | HRWHLQT (SEQ ID NO:50) | AQCCLFH (SEQ ID NO:51) |
| DKSTRTK (SEQ ID NO:55) | PCRYRLD (SEQ ID NO:56) | RSANLTR (SEQ ID NO:57) |
| RSDDLTR (SEQ ID NO:37) | RSDTLSN (SEQ ID NO:60) | TNSDRTK (SEQ ID NO:61) |
| RSDDLTR (SEQ ID NO:37) | RSDTLSE (SEQ ID NO:46) | KPYNLQQ (SEQ ID NO:64). |

2. The liver cell of claim 1, wherein the sequence of the endogenous PCSK9 gene is altered by cleaving the gene using a pair of zinc finger nucleases (ZFNs), wherein at least one of the zinc finger nucleases of the pair comprises the zinc finger protein of claim 1 and a cleavage domain.

3. The liver cell of claim 2, wherein the pair of ZFNs binds to paired target sites within SEQ ID NO:1 and SEQ ID NO:2; SEQ ID NO:3 and SEQ ID NO:4 SEQ ID NO:5 and SEQ ID NO:6; SEQ ID NO:7 and SEQ ID NO:8; SEQ ID NO:9 and SEQ ID NO:10; or SEQ ID NO:11 and SEQ ID NO:12.

4. The liver cell of claim 2, further comprising an exogenous sequence integrated into the cleaved endogenous PCSK9 gene.

5. The liver cell of claim 4, wherein the exogenous sequence comprises a transgene; introduces a mutation into the gene, or corrects a mutation in the endogenous gene.

6. The liver cell of claim 1, wherein the liver cell further comprises an artificial transcription factor comprising the zinc finger protein of claim 1 and a transcriptional regulatory domain, wherein the artificial transcription factor alters expression of the endogenous gene.

7. The liver cell of claim 6, wherein the artificial transcription factor activates or represses expression of the endogenous gene.

8. A pharmaceutical composition comprising the liver cell of claim 1.

9. A method of producing the liver cell of claim 1, the method comprising administering an artificial transcription factor or artificial nuclease comprising the zinc finger protein of claim 1 to the liver cell.

10. A fusion molecule comprising a zinc finger protein that binds to a target site in an endogenous PCSK9 gene and a functional domain, wherein the zinc finger protein comprises 5 or 6 zinc finger domains, each zinc finger domain comprising a recognition helix region sequence ordered F1 to F5 or F1 to F6, wherein the zinc finger protein comprises recognition helix regions ordered as shown in a single row of the following Table:

| F1 | F2 | F3 |
|---|---|---|
| QSSHLTR (SEQ ID NO:13) | QSGNLAR (SEQ ID NO:14) | QS SDLSR (SEQ ID NO:15) |
| RSDVLSE (SEQ ID NO:19) | TRNGLKY (SEQ ID NO:20) | TSGHLSR (SEQ ID NO:21) |
| QSGALAR (SEQ ID NO:25) | RSDVLSE (SEQ ID NO:19) | RSAHLSR (SEQ ID NO:26) |
| RSDHLSR (SEQ ID NO:27) | QSGHLSR (SEQ ID NO:22) | HKQHRDA (SEQ ID NO:18) |
| RSDHLSR (SEQ ID NO:27) | QQWDRKQ (SEQ ID NO:32) | TPSYLPT (SEQ ID NO:33) |
| QSGNLAR (SEQ ID NO:14) | TSGNLTR (SEQ ID NO:36) | RSDDLTR (SEQ ID NO:37) |
| QSGDLTR (SEQ ID NO:39) | RSDNLTR (SEQ ID NO:40) | QSGALAR (SEQ ID NO:25) |
| RSAHLSR (SEQ ID NO:26) | DSSDRKK (SEQ ID NO:43) | QHQVLVR (SEQ ID NO:44) |
| DGYYLPT (SEQ ID NO:48) | DRSALAR (SEQ ID NO:34) | ERQTLIK (SEQ ID NO:49) |
| RSDNLAR (SEQ ID NO:52) | DRSVLHR (SEQ ID NO:53) | RSDTLSA (SEQ ID NO:54) |
| RSDVLSE (SEQ ID NO:19) | QKCCLRS (SEQ ID NO:58) | DRSHLTR (SEQ ID NO:59) |
| HRQRLEE (SEQ ID NO:62) | RNASRTR (SEQ ID NO:63) | DRSHLTR (SEQ ID NO:59) |

| F4 | F5 | F6 |
|---|---|---|
| WHSSLHQ (SEQ ID NO:16) | LRHHLTR (SEQ ID NO:17) | HKQHRDA (SEQ ID NO:18) |
| QSGHLSR (SEQ ID NO:22) | NNRDLIN (SEQ ID NO:23) | TS SNLSR (SEQ ID NO:24) |
| RSDHLSR (SEQ ID NO:27) | DRSVLAR (SEQ ID NO:28) | N/A |
| DNSNRIK (SEQ ID NO:29) | RSDHLSE (SEQ ID NO:30) | HSRTRTK (SEQ ID NO:31) |
| DRSALAR (SEQ ID NO:34) | RSDHLSE (SEQ ID NO:30) | RKDARIT (SEQ ID NO:35) |
| RSDHLSE (SEQ ID NO:30) | DKSNRKK (SEQ ID NO:38) | N/A |
| QSGHLSR (SEQ ID NO:22) | RSDHLSQ (SEQ ID NO:41) | DSSHRTR (SEQ ID NO:42) |
| QNATRTK (SEQ ID NO:45) | RSDTLSE (SEQ ID NO:46) | RSPGRMG (SEQ ID NO:47) |
| QSGHLSR (SEQ ID NO:22) | HRWHLQT (SEQ ID NO:50) | AQCCLFH (SEQ ID NO:51) |
| DKSTRTK (SEQ ID NO:55) | PCRYRLD (SEQ ID NO:56) | RSANLTR (SEQ ID NO:57) |
| RSDDLTR (SEQ ID NO:37) | RSDTLSN (SEQ ID NO:60) | TNSDRTK (SEQ ID NO:61) |
| RSDDLTR (SEQ ID NO:37) | RSDTLSE (SEQ ID NO:46) | KPYNLQQ (SEQ ID NO:64). |

11. The fusion molecule of claim 10, wherein the functional domain comprises a transcriptional regulatory domain or a cleavage domain.

12. A polynucleotide encoding the fusion molecule of claim 10.

13. The polynucleotide of claim 12, wherein the polynucleotide is mRNA form.

14. A viral or non-viral expression vector comprising one or more polynucleotides of claim 12.

15. A pharmaceutical composition comprising the polynucleotide of claim 12.

16. A method of altering expression of a PCSK9 gene in a liver cell, the method comprising introducing the polynucleotide of claim 12 into the cell under conditions such that the expression of the PCSK9 gene is altered.

17. The method of claim 16, wherein the fusion molecule comprises an artificial zinc finger nuclease that alters expression of the PCSK9 gene by introducing one or more insertions and/or deletions into the gene.

18. A method of treating Familial Hypercholesterolemia/Static resistant hypercholesterolemia, the method comprising administering a pharmaceutical composition of claim 15 to a subject in need thereof.

19. A kit comprising a fusion molecule of claim 10.

* * * * *